(12) United States Patent
Basu et al.

(10) Patent No.: US 12,409,191 B2
(45) Date of Patent: *Sep. 9, 2025

(54) RENAL CELL POPULATIONS AND USES THEREOF

(71) Applicant: ProKidney, Cayman Islands (KY)

(72) Inventors: Joydeep Basu, Winston-Salem, NC (US); Kelly Guthrie, Winston-Salem, NC (US); Dominic Justewicz, Winston-Salem, NC (US); Teresa Burnette, Winston-Salem, NC (US); Andrew Bruce, Winston-Salem, NC (US); Russell W. Kelley, Winston-Salem, NC (US); John W. Ludlow, Winston-Salem, NC (US)

(73) Assignee: PROKIDNEY, Grand Cayman (KY)

( * ) Notice: Subject to any disclaimer, the term of this patent is extended or adjusted under 35 U.S.C. 154(b) by 308 days.

This patent is subject to a terminal disclaimer.

(21) Appl. No.: 17/825,652

(22) Filed: May 26, 2022

(65) Prior Publication Data

US 2022/0347221 A1 Nov. 3, 2022

Related U.S. Application Data

(63) Continuation of application No. 16/459,141, filed on Jul. 1, 2019, now Pat. No. 11,369,639, which is a continuation of application No. 15/623,197, filed on Jun. 14, 2017, now Pat. No. 10,363,274, which is a continuation of application No. 14/438,607, filed as application No. PCT/US2013/066707 on Oct. 24, 2013, now abandoned.

(60) Provisional application No. 61/876,616, filed on Sep. 11, 2013, provisional application No. 61/718,150, filed on Oct. 24, 2012.

(51) Int. Cl.
| | | |
|---|---|---|
| A61K 35/22 | (2015.01) | |
| C12N 5/00 | (2006.01) | |
| C12N 5/071 | (2010.01) | |
| G01N 33/569 | (2006.01) | |

(52) U.S. Cl.
CPC ............ *A61K 35/22* (2013.01); *C12N 5/0081* (2013.01); *C12N 5/0686* (2013.01); *G01N 33/56966* (2013.01); *C12N 2500/02* (2013.01); *C12N 2501/58* (2013.01); *C12N 2501/599* (2013.01); *G01N 2333/4742* (2013.01); *G01N 2333/705* (2013.01); *G01N 2333/9108* (2013.01)

(58) Field of Classification Search
None
See application file for complete search history.

(56) References Cited

U.S. PATENT DOCUMENTS

| | | | |
|---|---|---|---|
| 4,016,043 | A | 4/1977 | Schuurs et al. |
| 4,018,653 | A | 4/1977 | Mennen |
| 4,275,149 | A | 6/1981 | Litman et al. |
| 4,318,980 | A | 3/1982 | Boguslaski et al. |
| 4,424,279 | A | 1/1984 | Bohn et al. |
| 4,737,456 | A | 4/1988 | Weng et al. |
| 6,224,893 | B1 | 5/2001 | Langer et al. |
| 6,283,761 | B1 | 9/2001 | Joao |
| 6,306,406 | B1 | 10/2001 | Deluca |
| 6,346,274 | B1 | 2/2002 | Koll et al. |
| 6,576,019 | B1 | 6/2003 | Atala |
| 6,991,652 | B2 | 1/2006 | Burg |
| 7,189,413 | B2 | 3/2007 | Calias et al. |
| 7,563,822 | B2 | 7/2009 | Koizumi et al. |
| 7,788,087 | B2 | 8/2010 | Corston-Oliver et al. |
| 7,918,897 | B2 | 4/2011 | Bertram et al. |
| 8,318,484 | B2 | 11/2012 | Presnell et al. |
| 8,337,485 | B2 | 12/2012 | Ludlow et al. |
| 9,192,629 | B2 | 11/2015 | Presnell et al. |
| 9,534,203 | B2 | 1/2017 | Atala et al. |
| 9,724,367 | B2 | 8/2017 | Basu et al. |
| 10,363,274 | B2 | 7/2019 | Basu et al. |
| 11,369,639 | B2 | 6/2022 | Basu et al. |
| 2002/0051808 | A1 | 5/2002 | DeLuca |
| 2002/0182254 | A1 | 12/2002 | Calias et al. |
| 2004/0096916 | A1 | 5/2004 | Kellner et al. |
| 2004/0139072 | A1 | 7/2004 | Broder et al. |
| 2005/0048070 | A1 | 3/2005 | Ditzel et al. |
| 2005/0108384 | A1 | 5/2005 | Lambert et al. |
| 2005/0241012 | A1 | 10/2005 | Nigam et al. |
| 2006/0085248 | A1 | 4/2006 | Arnett et al. |
| 2007/0276507 | A1 | 11/2007 | Bertram et al. |
| 2008/0220443 | A1 | 9/2008 | Jin |
| 2009/0304639 | A1 | 12/2009 | Yokoo et al. |
| 2010/0070485 | A1 | 3/2010 | Parsons et al. |
| 2010/0131075 | A1 | 5/2010 | Ludlow et al. |
| 2011/0053157 | A1 | 3/2011 | Skog et al. |
| 2011/0117162 | A1 | 5/2011 | Presnell et al. |
| 2011/0123455 | A1 | 5/2011 | Presnell et al. |

(Continued)

FOREIGN PATENT DOCUMENTS

| | | |
|---|---|---|
| CA | 2780320 A1 | 5/2011 |
| CN | 102271692 A | 12/2011 |

(Continued)

OTHER PUBLICATIONS

Fassett (2011) "Biomarkers in Chronic Kidney Disease: A Review", Kidney International, 80(8):806-821.

Eremina et al. (Mar. 13, 2008) "VEGF Inhibition and Renal Thrombotic Microangiopathy", The New England Journal of Medicine, 358(11):1129-1136.

Aboushwareb, Tamer, et al., "Erythropoietin producing cells for potential cell therapy." *World journal of urology* 26.4 (2008): 295-300.

(Continued)

*Primary Examiner* — Daniel C Gamett
(74) *Attorney, Agent, or Firm* — Mueting Raasch Group

(57) ABSTRACT

The present invention concerns enriched heterogeneous mammalian renal cell populations characterized by biomarkers, and methods of making and using the same.

19 Claims, 10 Drawing Sheets

(56) References Cited

U.S. PATENT DOCUMENTS

| | | |
|---|---|---|
| 2011/0177959 A1 | 7/2011 | Spain et al. |
| 2011/0256111 A1 | 10/2011 | Camussi et al. |
| 2012/0301899 A1 | 11/2012 | Choo et al. |
| 2013/0189223 A1 | 7/2013 | Ricardo et al. |
| 2014/0271578 A1 | 9/2014 | Hare et al. |
| 2014/0308695 A1 | 10/2014 | Bruce et al. |
| 2015/0030657 A1 | 1/2015 | Ludlow et al. |
| 2015/0246073 A1 | 9/2015 | Basu et al. |
| 2016/0101133 A1 | 4/2016 | Basu et al. |
| 2016/0206659 A1 | 7/2016 | Presnell et al. |
| 2016/0244751 A1 | 8/2016 | Llagan |
| 2017/0281684 A1 | 10/2017 | Basu et al. |
| 2017/0368102 A1 | 12/2017 | Basu et al. |
| 2018/0055885 A1 | 3/2018 | Jain et al. |

FOREIGN PATENT DOCUMENTS

| | | |
|---|---|---|
| JP | 2005-531321 A | 10/2005 |
| KR | 1020110100213 A | 9/2011 |
| RU | 2 373 942 C2 | 11/2009 |
| WO | 03013588 A1 | 2/2003 |
| WO | WO-2001005544 A2 | 1/2004 |
| WO | WO-2010/056328 A1 | 5/2010 |
| WO | WO-2011/140137 A2 | 11/2011 |
| WO | WO-2011/143499 A1 | 11/2011 |
| WO | WO-2011156642 A1 | 12/2011 |
| WO | WO-2012/064369 A1 | 5/2012 |
| WO | WO-2014066698 A1 | 5/2014 |
| WO | WO-2014066699 A1 | 5/2014 |
| WO | 2014182885 A2 | 11/2014 |
| WO | 2018237170 A1 | 12/2018 |
| WO | 2022104120 A1 | 5/2022 |

OTHER PUBLICATIONS

Adhirajan, N., et al., "Gelatin microspheres cross-linked with EDC as a drug delivery system for doxycyline: development and characterization." *Journal of microencapsulation* 24.7 (2007): 659-671.

Baer, Patrick C., et al., "Differentiation status of human renal proximal and distal tubular epithelial cells in vitro: Differential expression of characteristic markers." *Cells Tissues Organs* 184.1 (2006): 16-22.

Basu, Joydeep, et al., "Functional evaluation of primary renal cell/biomaterial Neo-Kidney Augment prototypes for renal tissue engineering." *Cell transplantation* 20.11-12 (2011): 1771-1790.

Basu, Joydeep, et al., "Organ specific regenerative markers in peri-organ adipose: kidney." *Lipids in health and disease* 10.1 (2011): 171.

Bedford, Jennifer J., et al., "Aquaporin expression in normal human kidney and in renal disease." *Journal of the American Society of Nephrology* 14.10 (2003): 2581-2587.

Bruno, Stefania, et al., "Isolation and characterization of resident mesenchymal stem cells in human glomeruli." *Stem cells and development* 18.6 (2009): 867-880.

Chang, Ju-Ying, et al., "In vivo evaluation of a biodegradable EDC/NHS-cross-linked gelatin peripheral nerve guide conduit material." *Macromolecular bioscience* 7.4 (2007): 500-507.

Christensen, Erik Ilsø, et al., "Megalin and cubilin: synergistic endocytic receptors in renal proximal tubule." *American Journal of Physiology-Renal Physiology* 280.4 (2001): F562-F573.

Chung, Soon Dong, et al., "Characterization of primary rabbit kidney cultures that express proximal tubule functions in a hormonally defined medium." *The Journal of Cell Biology* 95.1 (1982): 118-126.

Cornwell, Kevin G., et al., "Extracellular matrix biomaterials for soft tissue repair." *Clinics in podiatric medicine and surgery* 26.4 (2009): 507-523.

Damink, LHH Olde, et al., "Cross-linking of dermal sheep collagen using a water-soluble carbodiimide." *Biomaterials* 17.8 (1996): 765-773.

Cenni, Elisabetta, et al., "Biocompatibility and performance in vitro of a hemostatic gelatin sponge." *Journal of Biomaterials Science, Polymer Edition* 11.7 (2000): 685-699.

Engvall, Eva, et al., "Binding of soluble form of fibroblast surface protein, fibronectin, to collagen." *International Journal of Cancer* 20.1 (1977): 1-5.

Gagnieu, Christian Henry, et al., "In vivo biodegradability and biocompatibility of porcine type I atelocollagen newly crosslinked by oxidized glycogen." *Bio-medical materials and engineering* 17.1 (2007): 9-18.

Horiuchi, Seikoh, et al., "γ-Glutamyl Transpeptidase: Sidedness of its Active Site on Renal Brush-Border Membrane." *The FEBS Journal* 87.3 (1978): 429-437.

Kalmovarin, Nuanthip, et al., "Extrahepatic expression of plasma protein genes during inflammation." *Inflammation* 15.5 (1991): 369-379.

Kelley, Rusty, et al., "Tubular cell-enriched subpopulation of primary renal cells improves survival and augments kidney function in rodent model of chronic kidney disease." *American Journal of Physiology-Renal Physiology* 299.5 (2010): F1026-F1039.

Kim, Na Ryoung, et al., "Distinct differentiation properties of human dental pulp cells on collagen, gelatin, and chitosan scaffolds." *Oral Surgery, Oral Medicine, Oral Pathology, Oral Radiology and Endodontics* 108.5 (2009): e94-e100.

Kimura, Yu, et al., "Adipose tissue formation in collagen scaffolds with different biodegradabilities." *Journal of Biomaterials Science, Polymer Edition* 21.4 (2010): 463-476.

Kitamura, Shinji, et al., "Establishment and characterization of renal progenitor like cells from S3 segment of nephron in rat adult kidney." *The FASEB Journal* 19 (2005): 1789-1797.

Kommareddy, Sushma, et al., "Poly (ethylene glycol)-modified thiolated gelatin nanoparticles for glutathione-responsive intracellular DNA delivery." *Nanomedicine: nanotechnology, biology and medicine* 3.1 (2007): 32-42.

Lai, Jui-Yang. "Biocompatibility of chemically cross-linked gelatin hydrogels for ophthalmic use." *Journal of Materials Science: Materials in Medicine* 21.6 (2010): 1899-1911.

Lazzeri, Elena, et al., "Regenerative potential of embryonic renal multipotent progenitors in acute renal failure." *Journal of the American Society of Nephrology* 18.12 (2007): 3128-3138.

Lee, Chi H., et al., "Biomedical applications of collagen." *International journal of pharmaceutics* 221.1-2 (2001): 1-22.

Lindgren, David, et al., "Isolation and characterization of progenitor-like cells from human renal proximal tubules." *The American journal of pathology* 178.2 (2011): 828-837.

Ma, Lie, et al., "Biodegradability and cell-mediated contraction of porous collagen scaffolds: The effect of lysine as a novel crosslinking bridge." *Journal of Biomedical Materials Research Part A* 71.2 (2004): 334-342.

Malyszko, Jolanta, et al., "Adiponectin is related to CD146, a novel marker of endothelial cell activation/injury in chronic renal failure and peritoneally dialyzed patients." *The Journal of Clinical Endocrinology & Metabolism* 89.9 (2004): 4620-4627.

Michael, Lydia, et al., "The lectin Dolichos biflorus agglutinin is a sensitive indicator of branching morphogenetic activity in the developing mouse metanephric collecting duct system." *Journal of anatomy* 210.1 (2007): 89-97.

Muntner, Paul, et al., "Acute kidney injury in sepsis: questions answered, but others remain." *Kidney international* 77.6 (2010): 485-487.

Nachlas, Marvin M., et al., "Improvement in the histochemical localization of leucine aminopeptidase with a new substrate, L-leucyl-4-methoxy-2-naphthylamide." *The Journal of Cell Biology* 7.2 (1960): 261-264.

Oosterwijk, E., et al., "Expression of intermediate-sized filaments in developing and adult human kidney and in renal cell carcinoma." *Journal of Histochemistry & Cytochemistry* 38.3 (1990): 385-392.

Pieper, J. S., et al., "Development of tailor-made collagen-glycosaminoglycan matrices: EDC/NHS crosslinking, and ultrastructural aspects." *Biomaterials* 21.6 (2000): 581-593.

Presnell, Sharon C., et al., "Isolation, characterization, and expansion methods for defined primary renal cell populations from rodent,

(56) References Cited

OTHER PUBLICATIONS canine, and human normal and diseased kidneys." *Tissue Engineering Part C: Methods* 17.3 (2010): 261-273.

Pretlow, Theresa., et al., "Enzymatic histochemistry of mouse kidney in plastic." *Journal of Histochemistry & Cytochemistry* 35.4 (1987): 483-487.

Prozialeck, Walter C., et al., "Differential expression of E-cadherin, N-cadherin and beta-catenin in proximal and distal segments of the rat nephron." *BMC physiology* 4.1 (2004): 10.

Rohanizadeh, Ramin, et al., "Gelatin sponges (Gelfoam®) as a scaffold for osteoblasts." *Journal of Materials Science: Materials in Medicine* 19.3 (2008): 1173-1182.

Sagrinati, Costanza, et al., "Isolation and characterization of multipotent progenitor cells from the Bowman's capsule of adult human kidneys." *Journal of the American Society of Nephrology* 17.9 (2006): 2443-2456.

Sehgal, P.K., et al., "Collagen-coated microparticles in drug delivery." *Expert opinion on drug delivery* 6.7 (2009): 687-695.

Shen, Steven S., et al., "Kidney-specific cadherin, a specific marker for the distal portion of the nephron and related renal neoplasms." *Modern pathology* 18.7 (2005): 933.

Sutter, Marc, et al., "Recombinant gelatin hydrogels for the sustained release of proteins." *Journal of Controlled Release* 119.3 (2007): 301-312.

Takata, Kuniaki, et al., "Localization and trafficking of aquaporin 2 in the kidney." *Histochemistry and cell biology* 130.2 (2008): 197-209.

Takemoto, Satoru, et al., "Preparation of collagen/gelatin sponge scaffold for sustained release of bFGF." *Tissue Engineering Part A* 14.10 (2008): 1629-1638.

Tamma, Grazia, et al., "Hypotonicity induces aquaporin-2 internalization and cytosol-to-membrane translocation of ICln in renal cells." *Endocrinology* 148.3 (2007): 1118-1130.

Tate, Suresh S., et al., "Stimulation of the hydrolytic activity and decrease of the transpeptidase activity of γ-glutamyl transpeptidase by maleate; identity of a rat kidney maleate-stimulated glutaminase and γ-glutamyl transpeptidase." *Proceedings of the National Academy of Sciences* 71.9 (1974): 3329-3333.

Toubas, Julie, et al., "Alteration of connexin expression is an early signal for chronic kidney disease." *American Journal of Physiology-Renal Physiology* 301.1 (2011): F24-F32.

Ueland, Joseph, et al., "A novel role for the chemokine receptor Cxcr4 in kidney morphogenesis: an in vitro study." *Developmental Dynamics* 238.5 (2009): 1083-1091.

Vaidya, Vishal S., et al., "Kidney injury molecule-1 outperforms traditional biomarkers of kidney injury in preclinical biomarker qualification studies." *Nature biotechnology* 28.5 (2010): 478.

Vandelli, M. A., et al., "Gelatin microspheres crosslinked with D, L-glyceraldehyde as a potential drug delivery system: preparation, characterisation, in vitro and in vivo studies." *International journal of pharmaceutics* 215.1-2 (2001): 175-184.

Vandelli, M.A., et al., "Microwave-treated gelatin microspheres as drug delivery system." *Journal of Controlled Release* 96.1 (2004): 67-84.

Waksman, Byron H., et al., "The antigenicity of collagen." *The Journal of Immunology* 63.4 (1949): 427-433.

Welbourne, Tomas C., et al., "Glutamate transport and renal function." *American Journal of Physiology-Renal Physiology* 277.4 (1999): F501-F505.

Yamaleyeva, Liliya M., et al., "Cell Therapy with Human Renal Cell Cultures Containing Erythropoietin-Positive Cells Improves Chronic Kidney Injury." *Stem cells translational medicine* 1.5 (2012): 373-383.

Young, Simon, et al., "Gelatin as a delivery vehicle for the controlled release of bioactive molecules." *Journal of controlled release* 109.1-3 (2005): 256-274.

Zhou, Hua, et al., "Urinary exosomal transcription factors, a new class of biomarkers for renal disease." *Kidney international* 74.5 (2008): 613-621.

Anjaparidze, et al., "Tissue Culture in Virological Studies", Medgiz, 1962, pp. 72-90. (with English translation of Russian Office Action citing Anjaparidze (summary of reasons reference was cited at first full paragraph on p. 2 of 3 of the translated Office Action)).

Brunszkill, et al., "Atlas of Gene Expression in the Developing Kidney at Microanatomic Resolution", Developmental Cell, vol. 15, Issue 5, Nov. 2008, pp. 781-791.

Vechkanov et al. (2012) "Tutorial : Basics of Cell Engineering", Foundations of Cellular Engineering, a Textbook, 133 pages. (only Russian copy; English translation of Russian Office Action citing reference attached).

DesRochers, et al., "Bioengineered 3D Human Kidney Tissue, A Platform for the Determination of Nephrotoxicity", PLoS One, 8(3):e59219, 2013, (12 pages).

PrestoBlueTM Cell Viability Reagent, Invitrogen catalog, Aug. 2011 (Year: 2011).

Ishibashi et al. (Aug. 2012) "Effectiveness of gelatin solidification for unfrozen preservation and transportation of astrocytes", Advances in Biological Chemistry, 2(2):238-242.

RENAL CELL POPULATIONS AND USES THEREOF

CROSS-REFERENCE TO RELATED APPLICATIONS

The present application claims priority to U.S. Provisional Patent Application Ser. No. 61/718,150, entitled "Isolated Regenerative Renal Cells and Uses Thereof", filed 24 Oct. 2012, and 61/876,616, entitled "Renal Cell Populations and Uses Thereof" filed 11 Sep. 2013.

TECHNICAL FIELD

The present disclosure generally relates to an enriched heterogeneous mammalian kidney-derived cell population, methods of identifying the cell population, methods for their use in the preparation of a regenerative medicine therapy, and methods for treating kidney disease by administration of the enriched heterogeneous kidney-derived cell population to a mammalian subject are provided herein.

BACKGROUND OF THE INVENTION

Collagen and gelatin-based biomaterials have been successfully employed for a variety of tissue engineering applications (Rohanizadeh et al. J Mater Sci Mater Med 2008; 19: 1173-1182; Takemoto et al. Tissue Eng Part A 2008; 14: 1629-1638; Young et al. J Control Release 2005; 109: 256-274). Both of these macromolecules are characterized by excellent biocompatibility and low antigenicity (Cenni et al. J Biomater Sci Polym Ed 2000; 11: 685-699; Lee et al. Int J Pharm 2001; 221: 1-22; Waksman et al. J Immunol 1949; 63: 427-433); however, since gelatin is obtained by the hydrolysis of collagen, it has certain advantages over the latter: (a) 6 it is readily available and easy to use; (b) offers options relative to molecular weight and bloom (i.e. control over physical properties); and (c) is more flexible towards chemical modification and more straightforward to manufacture. Moreover, from a biological standpoint, gelatin maintains cytocompatibility and cell adherence properties similar to collagen Engvall et al. Int J Cancer 1977; 20: 1-5; Kim et al. Oral Surg Oral Med Oral Pathol Oral Radiol Endod 2009; 108: e94-100).

Various methods have been reported for the crosslinking of these macromolecules for the purpose of delaying their biodegradation to prolong their in vivo residence (in tissue engineering applications) or tailoring their drug releasing capacity (when used as drug carriers). Numerous methods have been published for chemical or photochemical crosslinking of collagen or gelatin (Adhirajan et al. J Microencapsul 2007; 24: 647-659; Chang et al. Macromol Biosci 2007; 7: 500-507; Gagnieu et al. Biomed Mater Eng 2007; 17: 9-18; Kimura et al. J Biomater Sci Polym Ed 2010; 21: 463-476; Ma et al. J Biomed Mater Res A 2004; 71: 334-342; Vandelli et al. Int J Pharm 2001; 215: 175-184; Vandelli et al. J Control Release 2004; 96: 67-84). The majority of these procedures are targeted to reduce the susceptibility of these biomaterials to enzymatic degradation and to extend their in vivo residence time (Chang et al. supra 2007; Ma et al. supra 2004). Other crosslinking methods are typically employed to yield gelatin or collagen-based biomaterials suitable as slow release drug, protein or nucleic acid carriers (Kimura supra 2010; Vandelli supra 2004; Kommareddy et al. Nanomedicine 2007; 3: 32-42; Sehgal et al. Expert Opin Drug Deliv 2009; 6: 687-695; Sutter et al. J Control Release 2007; 119: 301-312). A widely used crosslinking agent class for collagen and gelatin as well as other tissue engineering-compatible systems is the carbodiimides (Adhirajan supra 2007; Olde Damink et al. Biomaterials 1996; 17: 765-773; Pieper et al. Biomaterials 2000; 21: 581-593; Cornwell et al. Clin Podiatr Med Surg 2009; 26: 507-523). These molecules are known as zero-length crosslinkers and act by mediating the formation of amide bonds between carboxyl and primary amine functionalities present on the species to be crosslinked. In addition, carbodiimides are less cytotoxic compared to other common crosslinking agent (e.g. glutaraldehyde) (Lai et al. J Mater Sci Mater Med 2010; 21: 1899-1911). Glutaraldehylde is used as a crosslinker in Cultispher™ beads. Burg U.S. Pat. No. 6,991,652 describes tissue engineering composites containing three-dimensional support constructs for cells that may be delivered to a subject.

Regenerative medicine technologies provide next-generation therapeutic options for chronic kidney disease (CKD). Presnell et al. WO/2010/056328 and Ilagan et al. PCT/US2011/036347 describe isolated bioactive renal cells, including tubular and erythropoietin (EPO)-producing kidney cell populations, and methods of isolating and culturing the same, as well as methods of treating a subject in need with the cell populations.

There is a need for therapeutic formulations that are suitable for delivery of active agents, such as for example, bioactive cells in tissue engineering and regenerative medicine applications, to subjects in need.

The kidney is a complex organ that performs many functions to keep the blood clean and chemically balanced. In addition to removing wastes, the kidneys release three important hormones:
  erythropoietin, or EPO, which stimulates the bone marrow to make red blood cells
  renin, which regulates blood pressure; and
  calcitriol, the active form of vitamin D, which helps maintain calcium for bones and for normal chemical balance in the body.

To perform these functions the kidney comprises numerous different cell types. However, not all renal cells are required for a regenerative response and identifying the combination of cells useful in eliciting a regenerative response has been the subject of investigation. Thus, there remains a need for methods that identify a heterogeneous renal cell population, i.e. bioactive cells, that finds use in the therapeutic formulations disclosed herein.

SUMMARY OF THE INVENTION

Disclosed herein is a heterogeneous mammalian renal cell population from mammalian kidney tissue. Methods for the isolation and purification of the mammalian kidney-derived cell population are provided. A unique population of mammalian kidney-derived cells is characterized by phenotypic characteristics, for example, biomarker phenotype. Biomarker expression phenotype is retained after multiple passages of the mammalian kidney-derived cell population in culture and is suitable for use in the preparation of a regenerative therapy.

Described herein are a select population of human renal cell population characterized by specific biomarkers and their use.

The select population of human renal cells allows the use a smaller numbers of cells that provide a regenerative stimulus. This smaller number is advantageous because it lowers the possibility of adverse immunological events as well as provide a regenerative stimulus. The selected renal cell population does not require a large proportion of stem cells to be effective as a regenerative stimulus. The selected renal cell population may be recovered from a diseased kidney.

In one aspect, there is provided methods for identifying and/or characterizing a heterogeneous renal cell population. In one embodiment, the heterogeneous renal cell population is characterized by its phenotypic expression of biomarkers. In certain embodiments, the renal cells are identified with one or more reagents that allow detection of the biomarkers on/in the heterogeneous renal cell population. Detection of the biomarkers can be carried out by any suitable method, for example, those based on immunofluorescent microscopy, flow cytometry, fiber-optic scanning cytometry, or laser scanning cytometry. In one embodiment, a method of identifying a heterogeneous renal cell population suitable for implantation and/or eliciting a regenerative response, said method comprising the steps:

Isolating cells from a mammalian kidney sample;

Exposing said isolated cells to one or more labeled detection moiety, wherein each labeled detection moiety is directed to a different biomarker and is labeled with a different label;

Determining the percentage of cells that express each of said biomarker.

In one embodiment, the cell population is an SRC cell population that expresses two or more biomarkers listed in Tables 12.2 and 12.3. In one embodiment, the biomarkers have levels of expression as provided in Table 12.4. In an embodiment the SRC cell population have levels of expression for GGT-1 and CK18 greater than 18% and 80%, respectively.

In one aspect, there is provided injectable, therapeutic formulations containing active agents, e.g., bioactive cells. In one embodiment, the injectable formulation comprises bioactive cells and a temperature-sensitive cell-stabilizing biomaterial. In another embodiment, the a temperature-sensitive cell-stabilizing biomaterial maintains (i) a substantially solid state at about 8° C. or below and/or (ii) a substantially liquid state at ambient temperature or above. In one other embodiment, the bioactive cells comprise renal cells, as described herein. In another embodiment, the bioactive cells are substantially uniformly dispersed throughout the volume of the cell-stabilizing biomaterial. In other embodiments, the biomaterial has a solid-to-liquid transitional state between about 8° C. and about ambient temperature or above. In one embodiment, the substantially solid state is a gel state. In another embodiment, the cell-stabilizing biomaterial comprises a hydrogel. In one other embodiment, the hydrogel comprises gelatin. In other embodiments, the gelatin is present in the formulation at about 0.5% to about 1% (w/v). In one embodiment, the gelatin is present in the formulation at about 0.75% (w/v). In another embodiment, the formulation further includes a cell viability agent. In one other embodiment, the cell viability agent comprises an agent selected from the group consisting of an antioxidant, an oxygen carrier, an immunomodulatory factor, a cell recruitment factor, a cell attachment factor, an anti-inflammatory agent, an immunosuppressant, an angiogenic factor, and a wound healing factor. In some embodiments, the cell viability agent is an antioxidant. In one embodiment, the antioxidant is 6-hydroxy-2,5,7,8-tetramethylchroman-2-carboxylic acid. In another embodiment, the 6-hydroxy-2,5,7,8-tetramethylchroman-2-carboxylic acid is present at about 50 µM to about 150 µM. In one other embodiment, the 6-hydroxy-2,5,7,8-tetramethylchroman-2-carboxylic acid is present at about 100 µM. In some embodiments, the cell viability agent is an oxygen carrier. In one embodiment, the oxygen carrier is a perfluorocarbon. In other embodiments, the cell viability agent is an immunomodulatory agent. In one embodiment, the cell viability agent is an immunosuppressant.

In another aspect, there is provided injectable, therapeutic formulations containing bioactive renal cells. In one embodiment, the formulation comprises bioactive renal cells, about 0.75% (w/v) gelatin, and about 100 µM 6-hydroxy-2,5,7,8-tetramethylchroman-2-carboxylic acid, wherein the formulation has (i) a substantially solid state at about 8° C. or below, and (ii) a substantially liquid state at ambient temperature or above. In another embodiment, the bioactive renal cells are substantially uniformly dispersed throughout the volume of the cell-stabilizing biomaterial. In one other embodiment, the biomaterial comprises a solid-to-liquid transitional state between about 8° C. and about ambient temperature. In other embodiments, the substantially solid state is a gel state. In some embodiments, the formulation further includes a cell viability agent. In yet another embodiment, the cell viability agent comprises an agent selected from the group consisting of an an antioxidant, an oxygen carrier, an immunomodulatory factor, a cell recruitment factor, a cell attachment factor, an anti-inflammatory agent, an angiogenic factor, and a wound healing factor. In one embodiment, the cell viability agent is an oxygen carrier. In another embodiment, the oxygen carrier is a perfluorocarbon. In one other embodiment, the cell viability agent is an immunomodulatory agent. In other embodiments, the cell viability agent is an immunosuppressant.

In one other aspect, the present disclosure provides a formulation described herein that further includes biocompatible beads. In one embodiment, the biocompatible beads comprise a biomaterial. In another embodiment, the beads are crosslinked. In one other embodiment, the crosslinked beads have a reduced susceptibility to enzymatic degradation as compared to non-crosslinked biocompatible beads. In other embodiments, the crosslinked beads are carbodiimide-crosslinked beads. In one embodiment, the carbodiimide is selected from the group consisting of 1-Ethyl-3-[3-dimethylaminopropyl] carbodiimide hydrochloride (EDC), DCC-N,N'-dicyclohexylcarbodiimide (DCC), and N,N'-Diisopropylcarbodiimide (DIPC). In another embodiment, the carbodiimide is 1-Ethyl-3-[3-dimethylaminopropyl] carbodiimide hydrochloride (EDC). In one other embodiment, the crosslinked beads comprise a reduced number of free primary amines as compared to non-crosslinked beads. In other embodiments, the number of free primary amines is detectable spectrophotometrically at about 355 nm. In some embodiments, the beads are seeded with the bioactive cells. In one embodiment, the bioactive cells are renal cells. In another embodiment, the formulation further comprises additional biocompatible beads that comprise a temperature-sensitive biomaterial that maintains (i) a substantially solid state at ambient temperature or below, and (ii) a substantially liquid state at about 37° C. or above. In one other embodiment, the biomaterial of the beads comprises a solid-to-liquid transitional state between ambient temperature and about 37° C. In other embodiments, the substantially solid state is a gel state. In one embodiment, the biomaterial of the beads comprises a hydrogel. In another embodiment, the hydrogel comprises gelatin. In one other embodiment, the beads comprise gelatin at about 5% (w/v) to about 10% (w/v). In some embodiments, the additional biocompatible beads are spacer beads. In other embodiments, the spacer beads are not seeded with bioactive cells.

In another aspect, the formulations of the present disclosure contain products secreted by a renal cell population. In one embodiment, the formulations comprise products secreted by a renal cell population and/or bioactive cells. In one other embodiment, the bioactive cells are renal cells. In another embodiment, the products comprise one or more of paracrine factors, endocrine factors, and juxtacrine factors. In one other embodiment, the products comprise vesicles. In other embodiments, the vesicles comprise microvesicles. In one embodiment, the vesicles comprise exosomes. In another embodiment, the vesicles comprise a secreted product selected from the group consisting of paracrine factors, endocrine factors, juxtacrine factors, and RNA.

DETAILED DESCRIPTION OF THE INVENTION

Figure 1:
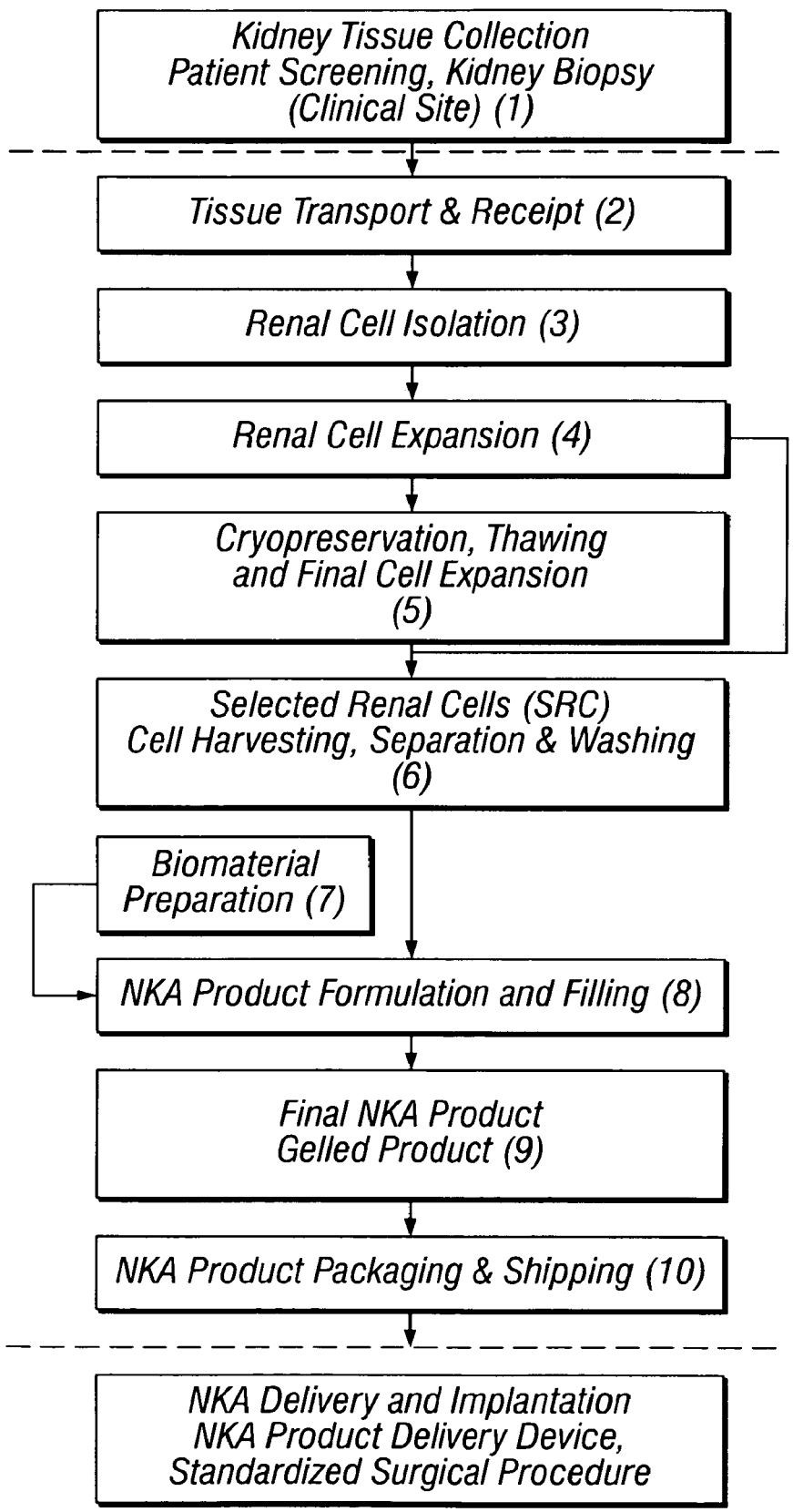
FIG. 1 is a flow diagram of the overall NKA manufacturing process described herein.

Disclosed herein are therapeutic formulations for active agents, such as bioactive cells, as well as methods of preparing the same and methods of treating a subject in need with the formulations. The bioactive cell formulations may be suitable for heterogenous mixtures or fractions of bioactive renal cells (BRCs). The bioactive renal cells may be isolated renal cells including tubular and erythropoietin (EPO)-producing kidney cells. The BRC cell populations may include enriched tubular and EPO-producing cell populations. The BRCs may be derived from or are themselves renal cell fractions from healthy individuals. In addition, there is provided renal cell fractions obtained from an unhealthy individual that may lack certain cellular components when compared to the corresponding renal cell fractions of a healthy individual, yet still retain therapeutic properties. The present disclosure also provides therapeutically-active cell populations lacking cellular components compared to a healthy individual, which cell populations can be, in one embodiment, isolated and expanded from autologous sources in various disease states.

Although bioactive cell formulations are described herein, the present disclosure contemplates formulations containing a variety of other active agents. Other suitable active agents include, without limitation, cellular aggregates, acellular biomaterials, secreted products from bioactive cells, large and small molecule therapeutics, as well as combinations thereof. For example, one type of bioactive cells may be combined with biomaterial-based microcarriers with or without therapeutic molecules or another type of bioactive cells, unattached cells may be combined with acellular particles.

1. Definitions

Unless defined otherwise, technical and scientific terms used herein have the same meaning as commonly understood by one of ordinary skill in the art to which this invention belongs. Principles of Tissue Engineering, 3rd Ed. (Edited by R Lanza, R Langer, & J Vacanti), 2007 provides one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "cell population" as used herein refers to a number of cells obtained by isolation directly from a suitable tissue source, usually from a mammal. The isolated cell population may be subsequently cultured in vitro. Those of ordinary skill in the art will appreciate that various methods for isolating and culturing cell populations for use with the present invention and various numbers of cells in a cell population that are suitable for use in the present invention. A cell population may be an unfractionated, heterogeneous cell population derived from an organ or tissue, e.g., the kidney. For example, a heterogeneous cell population may be isolated from a tissue biopsy or from whole organ tissue. Alternatively, the heterogeneous cell population may be derived from in vitro cultures of mammalian cells, established from tissue biopsies or whole organ tissue. An unfractionated heterogeneous cell population may also be referred to as a non-enriched cell population. In one embodiment, the cell populations contain bioactive cells.

The term "native organ" shall mean the organ of a living subject. The subject may be healthy or un-healthy. An unhealthy subject may have a disease associated with that particular organ.

The term "native kidney" shall mean the kidney of a living subject. The subject may be healthy or un-healthy. An unhealthy subject may have a kidney disease.

The term "regenerative effect" shall mean an effect which provides a benefit to a native organ, such as the kidney. The effect may include, without limitation, a reduction in the degree of injury to a native organ or an improvement in, restoration of, or stabilization of a native organ function. Renal injury may be in the form of fibrosis, inflammation, glomerular hypertrophy, etc. and related to a disease associated with the native organ in the subject.

The term "admixture" as used herein refers to a combination of two or more isolated, enriched cell populations derived from an unfractionated, heterogeneous cell population. According to certain embodiments, the cell populations are renal cell populations.

An "enriched" cell population or preparation refers to a cell population derived from a starting organ cell population (e.g., an unfractionated, heterogeneous cell population) that contains a greater percentage of a specific cell type than the percentage of that cell type in the starting population. For example, a starting kidney cell population can be enriched for a first, a second, a third, a fourth, a fifth, and so on, cell population of interest. As used herein, the terms "cell population", "cell preparation" and "cell prototype" are used interchangeably.

In one aspect, the term "enriched" cell population as used herein refers to a cell population derived from a starting organ cell population (e.g., a cell suspension from a kidney biopsy or cultured mammalian kidney cells) that contains a percentage of cells capable of producing EPO that is greater than the percentage of cells capable of producing EPO in the starting population. For example, the term "B4" is a cell population derived from a starting kidney cell population that contains a greater percentage of EPO-producing cells, glomerular cells, and vascular cells as compared to the starting population. The cell populations may be enriched for one or more cell types and depleted of one or more other cell types. For example, an enriched EPO-producing cell population may be enriched for interstitial fibroblasts and depleted of tubular cells and collecting duct epithelial cells relative to the interstitial fibroblasts and tubular cells in a non-enriched cell population, i.e. the starting cell population from which the enriched cell population is derived. In all embodiments citing EPO-enriched or "B4" populations, the enriched cell populations are heterogeneous populations of cells containing cells that can produce EPO in an oxygen-regulated manner, as demonstrated by oxygen-tunable EPO expression from the endogenous native EPO gene.

In another aspect, an enriched renal cell population, which contains a greater percentage of a specific cell type, e.g., vascular, glomerular, or endocrine cells, than the percentage of that cell type in the starting population, may also lack or be deficient in one or more specific cell types, e.g., vascular, glomerular, or endocrine cells, as compared to a starting kidney cell population derived from a healthy individual or subject. For example, the term "B4'," or B4 prime," in one aspect, is a cell population derived from a starting kidney cell population that lacks or is deficient in one or more cell types, e.g., vascular, glomerular or endocrine, depending on the disease state of the starting specimen, as compared to a healthy individual. In one embodiment, the B4' cell population is derived from a subject having chronic kidney disease. In one embodiment, the B4' cell population is derived from a subject having focal segmental glomerulosclerosis (FSGS). In another embodiment, the B4' cell population is derived from a subject having autoimmune glomerulonephritis. In another aspect, B4' is a cell population derived from a starting cell population including all cell types, e.g., vascular, glomerular, or endocrine cells, which is later depleted of or made deficient in one or more cell types, e.g., vascular, glomerular, or endocrine cells. In yet another aspect, B4' is a cell population derived from a starting cell population including all cell types, e.g., vascular, glomerular, or endocrine cells, in which one or more specific cell types e.g., vascular, glomerular, or endocrine cells, is later enriched. For example, in one embodiment, a B4' cell population may be enriched for vascular cells but depleted of glomerular and/or endocrine cells. In another embodiment, a B4' cell population may be enriched for glomerular cells but depleted of vascular and/or endocrine cells. In another embodiment, a B4' cell population may be enriched for endocrine cells but depleted of vascular and/or glomerular cells. In another embodiment, a B4' cell population may be enriched for vascular and endocrine cells but depleted of glomerular cells. In preferred embodiments, the B4' cell population, alone or admixed with another enriched cell population, e.g., B2 and/or B3, retains therapeutic properties. A B4' cell population, for example, is described herein in the Examples, e.g., Examples 11-13.

In another aspect, an enriched cell population may also refer to a cell population derived from a starting kidney cell population as discussed above that contains a percentage of cells expressing one or more vascular, glomerular and proximal tubular markers with some EPO-producing cells that is greater than the percentage of cells expressing one or more vascular, glomerular and proximal tubular markers with some EPO-producing cells in the starting population. For example, the term "B3" refers to a cell population derived from a starting kidney cell population that contains a greater percentage of proximal tubular cells as well as vascular and glomerular cells as compared to the starting population. In one embodiment, the B3 cell population contains a greater percentage of proximal tubular cells as compared to the starting population but a lesser percentage of proximal tubular cells as compared to the B2 cell population. In another embodiment, the B3 cell population contains a greater percentage of vascular and glomerular cells markers with some EPO-producing cells as compared to the starting population but a lesser percentage of vascular and glomerular cells markers with some EPO-producing cells as compared to the B4 cell population.

In another aspect, an enriched cell population may also refer to a cell population derived from a starting kidney cell population as discussed above that contains a percentage of cells expressing one or more tubular cell markers that is greater than the percentage of cells expressing one or more tubular cell markers in the starting population. For example, the term "B2" refers to a cell population derived from a starting kidney cell population that contains a greater percentage of tubular cells as compared to the starting population. In addition, a cell population enriched for cells that express one or more tubular cell markers (or "B2") may contain some epithelial cells from the collecting duct system. Although the cell population enriched for cells that express one or more tubular cell markers (or "B2") is relatively depleted of EPO-producing cells, glomerular cells, and vascular cells, the enriched population may contain a smaller percentage of these cells (EPO-producing, glomerular, and vascular) in comparison to the starting population. In general, a heterogeneous cell population is depleted of one or more cell types such that the depleted cell population contains a lesser proportion of the cell type(s) relative to the proportion of the cell type(s) contained in the heterogeneous cell population prior to depletion. The cell types that may be depleted are any type of kidney cell. For example, in certain embodiments, the cell types that may be depleted include cells with large granularity of the collecting duct and tubular system having a density of < about 1.045 g/ml, referred to as "B1". In certain other embodiments, the cell types that may be depleted include debris and small cells of low granularity and viability having a density of > about 1.095 g/ml, referred to as "B5". In some embodiments, the cell population enriched for tubular cells is relatively depleted of all of the following: "B1", "B5", oxygen-tunable EPO-expressing cells, glomerular cells, and vascular cells.

The term "hypoxic" culture conditions as used herein refers to culture conditions in which cells are subjected to a reduction in available oxygen levels in the culture system relative to standard culture conditions in which cells are cultured at atmospheric oxygen levels (about 21%). Non-hypoxic conditions are referred to herein as normal or normoxic culture conditions.

The term "oxygen-tunable" as used herein refers to the ability of cells to modulate gene expression (up or down) based on the amount of oxygen available to the cells. "Hypoxia-inducible" refers to the upregulation of gene expression in response to a reduction in oxygen tension (regardless of the pre-induction or starting oxygen tension).

The term "biomaterial" as used herein refers to a natural or synthetic biocompatible material that is suitable for introduction into living tissue. A natural biomaterial is a material that is made by or originates from a living system. Synthetic biomaterials are materials which are not made by or do not originate from a living system. The biomaterials disclosed herein may be a combination of natural and synthetic biocompatible materials. As used herein, biomaterials include, for example, polymeric matrices and scaffolds. Those of ordinary skill in the art will appreciate that the biomaterial(s) may be configured in various forms, for example, as porous foam, gels, liquids, beads, solids, and may comprise one or more natural or synthetic biocompatible materials. In one embodiment, the biomaterial is the liquid form of a solution that is capable of becoming a hydrogel.

The term "modified release" or the equivalent terms "controlled release", "delayed release", or "slow release" refer to formulations that release an active agent, such as bioactive cells, over time or at more than one point in time following administration to an individual. Modified release of an active agent, which can occur over a range of desired times, e.g., minutes, hours, days, weeks, or longer, depending upon the formulation, is in contrast to standard formulations in which substantially the entire dosage unit is available immediately after administration. For tissue engineering and regenerative medicine applications, preferred modified release formulations provide for the release of an active agent at multiple time points following local administration (e.g., administration of an active agent directly to a solid organ). For example, a modified release formulation of bioactive cells would provide an initial release of cells immediately at the time of administration and a later, second release of cells at a later time. The time delay for the second release of an active agent may be minutes, hours, or days after the initial administration. In general, the period of time for delay of release corresponds to the period of time that it takes for a biomaterial carrier of the active agent to lose it structural integrity. The delayed release of an active agent begins as such integrity begins to degrade and is completed by the time integrity fails completely. Those of ordinary skill in the art will appreciate other suitable mechanisms of release.

The term "anemia" as used herein refers to a deficit in red blood cell number and/or hemoglobin levels due to inadequate production of functional EPO protein by the EPO-producing cells of a subject, and/or inadequate release of EPO protein into systemic circulation, and/or the inability of erythroblasts in the bone marrow to respond to EPO protein. A subject with anemia is unable to maintain erythroid homeostasis. In general, anemia can occur with a decline or loss of kidney function (e.g., chronic renal failure), anemia associated with relative EPO deficiency, anemia associated with congestive heart failure, anemia associated with myelosuppressive therapy such as chemotherapy or anti-viral therapy (e.g., AZT), anemia associated with non-myeloid cancers, anemia associated with viral infections such as HIV, and anemia of chronic diseases such as autoimmune diseases (e.g., rheumatoid arthritis), liver disease, and multi-organ system failure.

The term "EPO-deficiency" refers to any condition or disorder that is treatable with an erythropoietin receptor agonist (e.g., recombinant EPO or EPO analogs), including anemia.

The term "organ-related disease" as used herein refers to disorders associated with any stage or degree of acute or chronic organ failure that results in a loss of the organ's ability to perform its function.

The term "kidney disease" as used herein refers to disorders associated with any stage or degree of acute or chronic renal failure that results in a loss of the kidney's ability to perform the function of blood filtration and elimination of excess fluid, electrolytes, and wastes from the blood. Kidney disease also includes endocrine dysfunctions such as anemia (erythropoietin-deficiency), and mineral imbalance (Vitamin D deficiency). Kidney disease may originate in the kidney or may be secondary to a variety of conditions, including (but not limited to) heart failure, hypertension, diabetes, autoimmune disease, or liver disease. Kidney disease may be a condition of chronic renal failure that develops after an acute injury to the kidney. For example, injury to the kidney by ischemia and/or exposure to toxicants may cause acute renal failure; incomplete recovery after acute kidney injury may lead to the development of chronic renal failure.

The term "treatment" refers to both therapeutic treatment and prophylactic or preventative measures for kidney disease, anemia, EPO deficiency, tubular transport deficiency, or glomerular filtration deficiency wherein the object is to reverse, prevent or slow down (lessen) the targeted disorder. Those in need of treatment include those already having a kidney disease, anemia, EPO deficiency, tubular transport deficiency, or glomerular filtration deficiency as well as those prone to having a kidney disease, anemia, EPO deficiency, tubular transport deficiency, or glomerular filtration deficiency or those in whom the kidney disease, anemia, EPO deficiency, tubular transport deficiency, or glomerular filtration deficiency is to be prevented. The term "treatment" as used herein includes the stabilization and/or improvement of kidney function.

The term "in vivo contacting" as used herein refers to direct contact in vivo between products secreted by an enriched population of cells and a native organ. For example, products secreted by an enriched population of renal cells (or an admixture or construct containing renal cells/renal cell fractions) may in vivo contact a native kidney. The direct in vivo contacting may be paracrine, endocrine, or juxtacrine in nature. The products secreted may be a heterogeneous population of different products described herein.

The term "ribonucleic acid" or "RNA" as used herein refers to a chain of nucleotide units where each unit is made up of a nitrogenous base, a ribose sugar, and a phosphate. The RNA may be in single or double stranded form. The RNA may be part of, within, or associated with a vesicle. The vesicle may be an exosome. RNA includes, without limitation, mRNAs, rRNA, small RNAs, snRNAs, snoRNAs, microRNAs (miRNAs), small interfering RNAs (siRNAs), and noncoding RNAs. The RNA is preferably human RNA.

The term "construct" refers to one or more cell populations deposited on or in a surface of a scaffold or matrix made up of one or more synthetic or naturally-occurring biocompatible materials. The one or more cell populations may be coated with, deposited on, embedded in, attached to, seeded, or entrapped in a biomaterial made up of one or more synthetic or naturally-occurring biocompatible biomaterials, polymers, proteins, or peptides. The one or more cell populations may be combined with a biomaterial or scaffold or matrix in vitro or in vivo. In general, the one or more biocompatible materials used to form the scaffold/biomaterial is selected to direct, facilitate, or permit the formation of multicellular, three-dimensional, organization of at least one of the cell populations deposited thereon. The one or more biomaterials used to generate the construct may also be selected to direct, facilitate, or permit dispersion and/or integration of the construct or cellular components of the construct with the endogenous host tissue, or to direct, facilitate, or permit the survival, engraftment, tolerance, or functional performance of the construct or cellular components of the construct.

The term "marker" or "biomarker" refers generally to a DNA, RNA, protein, carbohydrate, or glycolipid-based molecular marker, the expression or presence of which in a cultured cell population can be detected by standard methods (or methods disclosed herein) and is consistent with one or more cells in the cultured cell population being a particular type of cell. Such biomarkers include, but are not limited to, the genes set forth in Tables X and Y. The marker may be a polypeptide expressed by the cell or an identifiable physical location on a chromosome, such as a gene, a restriction endonuclease recognition site or a nucleic acid encoding a polypeptide (e.g., an mRNA) expressed by the native cell. The marker may be an expressed region of a gene referred to as a "gene expression marker", or some segment of DNA with no known coding function. The biomarkers may be cell-derived, e.g., secreted, products.

The terms "biomarker signature," "signature," "biomarker expression signature," or "expression signature" are used interchangeably herein and refer to one or a combination of biomarkers whose expression is an indicator of the cell type(s), e.g., epithelial, tubular, etc. comprising a cell population, e.g., bioactive renal cells. The biomarker signature may serve as an indictor of suitability of the cell population for use in the methods and manufactures provided for herein. In some embodiments, the biomarker signature is a "gene signature." The term "gene signature" is used interchangeably with "gene expression signature" and refers to one or a combination of polynucleotides whose expression is an indicator of cell type, e.g., epithelial, tubular, etc. In some embodiments, the biomarker signature is a "protein signature." The term "protein signature" is used interchangeably with "protein expression signature" and refers to one or a combination of polypeptides whose expression is an indicator of cell type, e.g., epithelial, tubular, etc.

The terms "level of expression" or "expression level" are used interchangeably and generally refer to either the amount of a polynucleotide or an amino acid product or protein in a biological sample, or the percentage of cells expressing the polynucleotide or an amino acid product or protein. "Expressing" or "Expression" and grammatical variants thereof refer to the presence of a polynucleotide or an amino acid product or protein in a detectable amount in a biological sample. For example, a protein that is detectable (above background or control values) may be said to express the protein. Similarly, if a portion of cells in a sample express the protein the sample may be said to express the protein. In the alternative, the sample may be said to have a level of expression relating to the percentage of cells expressing the protein, e.g., if 60% of the cells in a sample express the protein then the level of expression is 60%.

The terms "differentially expressed gene," "differential gene expression" and their synonyms, which are used interchangeably, refer to a gene whose expression is activated to a higher or lower level in a first cell or cell population, relative to its expression in a second cell or cell population. The terms also include genes whose expression is activated to a higher or lower level at different stages over time during passage of the first or second cell in culture. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between the first cell and the second cell. Differential expression includes both quantitative, as well as qualitative, differences in the temporal or cellular expression pattern in a gene or its expression products among, for example, the first cell and the second cell. For the purpose of this disclosure, "differential gene expression" is considered to be present when there is a difference between the expression of a given gene in the first cell and the second cell. The differential expression of a marker may be in cells from a patient before administration of a cell population, admixture, or construct (the first cell) relative to expression in cells from the patient after administration (the second cell).

The terms "inhibit", "down-regulate", "under-express" and "reduce" are used interchangeably and mean that the expression of a gene, or level of RNA molecules or equivalent RNA molecules encoding one or more proteins or protein subunits, or activity of one or more proteins or protein subunits, is reduced relative to one or more controls, such as, for example, one or more positive and/or negative controls. The under-expression may be in cells from a patient before administration of a cell population, admixture, or construct relative to cells from the patient after administration.

The term "up-regulate" or "over-express" is used to mean that the expression of a gene, or level of RNA molecules or equivalent RNA molecules encoding one or more proteins or protein subunits, or activity of one or more proteins or protein subunits, is elevated relative to one or more controls, such as, for example, one or more positive and/or negative controls. The over-expression may be in cells from a patient after administration of a cell population, admixture, or construct relative to cells from the patient before administration.

The term "subject" shall mean any single human subject, including a patient, eligible for treatment, who is experiencing or has experienced one or more signs, symptoms, or other indicators of an organ-related disease, such as kidney disease, anemia, or EPO deficiency. Such subjects include without limitation subjects who are newly diagnosed or previously diagnosed and are now experiencing a recurrence or relapse, or are at risk for a kidney disease, anemia, or EPO deficiency, no matter the cause. The subject may have been previously treated for a kidney disease, anemia, or EPO deficiency, or not so treated.

The term "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "sample" or "patient sample" or "biological sample" shall generally mean any biological sample obtained from a subject or patient, body fluid, body tissue, cell line, tissue culture, or other source. The term includes tissue biopsies such as, for example, kidney biopsies. The term includes cultured cells such as, for example, cultured mammalian kidney cells. Methods for obtaining tissue biopsies and cultured cells from mammals are well known in the art. If the term "sample" is used alone, it shall still mean that the "sample" is a "biological sample" or "patient sample", i.e., the terms are used interchangeably.

The term "test sample" refers to a sample from a subject that has been treated by a method disclosed herein. The test sample may originate from various sources in the mammalian subject including, without limitation, blood, semen, serum, urine, bone marrow, mucosa, tissue, etc.

The term "control" or "control sample" refers a negative or positive control in which a negative or positive result is expected to help correlate a result in the test sample. Controls that are suitable include, without limitation, a sample known to exhibit indicators characteristic of normal erythroid homeostasis, a sample known to exhibit indicators characteristic of anemia, a sample obtained from a subject known not to be anemic, and a sample obtained from a subject known to be anemic. Additional controls suitable for use in the methods provided herein include, without limitation, samples derived from subjects that have been treated with pharmacological agents known to modulate erythropoiesis (e.g., recombinant EPO or EPO analogs). In addition, the control may be a sample obtained from a subject prior to being treated by a method disclosed herein. An additional suitable control may be a test sample obtained from a subject known to have any type or stage of kidney disease, and a sample from a subject known not to have any type or stage of kidney disease. A control may be a normal healthy matched control. Those of skill in the art will appreciate other controls suitable for use herein.

"Regeneration prognosis", "regenerative prognosis", or "prognostic for regeneration" generally refers to a forecast or prediction of the probable regenerative course or outcome of the administration or implantation of a cell population, admixture or construct described herein. For a regeneration prognosis, the forecast or prediction may be informed by one or more of the following: improvement of a functional organ (e.g., the kidney) after implantation or administration, development of a functional kidney after implantation or administration, development of improved kidney function or capacity after implantation or administration, and expression of certain markers by the native kidney following implantation or administration.

"Regenerated organ" refers to a native organ after implantation or administration of a cell population, admixture, or construct as described herein. The regenerated organ is characterized by various indicators including, without limitation, development of function or capacity in the native organ, improvement of function or capacity in the native organ, and the expression of certain markers in the native organ. Those of ordinary skill in the art will appreciate that other indicators may be suitable for characterizing a regenerated organ.

"Regenerated kidney" refers to a native kidney after implantation or administration of a cell population, admixture, or construct as described herein. The regenerated kidney is characterized by various indicators including, without limitation, development of function or capacity in the native kidney, improvement of function or capacity in the native kidney, and the expression of certain markers in the native kidney. Those of ordinary skill in the art will appreciate that other indicators may be suitable for characterizing a regenerated kidney.

The term "cellular aggregate" or "spheroid" refers to an aggregate or assembly of cells cultured to allow 3D growth as opposed to growth as a monolayer. It is noted that the term "spheroid" does not imply that the aggregate is a geometric sphere. The aggregate may be highly organized with a well defined morphology or it may be an unorganized mass; it may include a single cell type or more than one cell type. The cells may be primary isolates, or a permanent cell line, or a combination of the two. Included in this definition are organoids and organotypic cultures.

The term "ambient temperature" refers to the temperature at which the formulations of the present disclosure will be administered to a subject. Generally, the ambient temperature is the temperature of a temperature-controlled environment. Ambient temperature ranges from about 18° C. to about 30° C. In one embodiment, ambient temperature is about 18° C., about 19° C., about 20° C., about 21° C., about 22° C., about 23° C., about 24° C., about 25° C., about 26° C., about 27° C., about 28° C., about 29° C., or about 30° C.

The word "label" when used herein refers to a compound or composition that is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "detection" includes any means of detecting, including direct and indirect detection.

A "kit" is any manufacture (e.g., a package or container) comprising at least one reagent, e.g., a medicament for treatment of an kidney disease, or a probe for specifically detecting a biomarker gene or protein as disclosed herein. The manufacture is preferably promoted, distributed, or sold as a unit for performing the methods disclosed herein.

2. Cell Populations

The formulations of the present disclosure may contain isolated, heterogeneous populations of kidney cells, and admixtures thereof, enriched for specific bioactive components or cell types and/or depleted of specific inactive or undesired components or cell types for use in the treatment of kidney disease, i.e., providing stabilization and/or improvement and/or regeneration of kidney function, were previously described in Presnell et al. U.S. 2011-0117162 and Ilagan et al. PCT/US2011/036347, the entire contents of which are incorporated herein by reference. The formulations may contain isolated renal cell fractions that lack cellular components as compared to a healthy individual yet retain therapeutic properties, i.e., provide stabilization and/or improvement and/or regeneration of kidney function. The cell populations, cell fractions, and/or admixtures of cells described herein may be derived from healthy individuals, individuals with a kidney disease, or subjects as described herein.

The present disclosure provides formulations which are suitable for use with various bioactive cell populations including, without limitation, isolated cell population(s), cell fraction(s), admixture(s), enriched cell population(s), cellular aggregate(s), and any combination thereof. In an embodiment, the bioactive cell populations are bioactive renal cells.

Bioactive Cell Populations

The present disclosure contemplates therapeutic formulations suitable for bioactive cell populations that are to be administered to target organs or tissue in a subject in need. A bioactive cell population generally refers to a cell population potentially having therapeutic properties upon administration to a subject. For example, upon administration to a subject in need, a bioactive renal cell population can provide stabilization and/or improvement and/or regeneration of kidney function in the subject. The therapeutic properties may include a regenerative effect.

Bioactive cell populations include, without limitation, stem cells (e.g., pluripotent, multipotent, oligopotent, or unipotent) such as embryonic stem cells, amniotic stem cells, adult stem cells (e.g., hematopoietic, mammary, intestinal, mesenchymal, placental, lung, bone marrow, blood, umbilical cord, endothelial, dental pulp, adipose, neural, olfactory, neural crest, testicular), induced pluripotent stem cells; genetically modified cells; as well as cell populations or tissue explants derived from any source of the body. The formulations of the present disclosure may also be used with renal adipose-derived cell populations as described in Basu et al. PCT/US11/39859 filed on Jun. 9, 2011; and with the adipose-derived or peripheral blood-derived smooth muscle cells described in Ludlow et al. U.S. 2010-0131075 and Ludlow et al. PCT/US11/35058 filed on May 3, 2011; or bladder-derived urothelial or smooth muscle cells as described in Atala U.S. Pat. No. 6,576,019, each of which is incorporate herein by reference in its entirety. The bioactive cell populations may be isolated, enriched, purified, homogeneous, or heterogeneous in nature. Those of ordinary skill in the art will appreciate other bioactive cell populations that are suitable for use in the formulations of the present disclosure.

In one embodiment, the source of cells is the same as the intended target organ or tissue. For example, renal cells may be sourced from the kidney to be used in a formulation to be administered to the kidney. In another embodiment, the source of cells is not the same as the intended target organ or tissue. For example, erythropoietin-expressing cells may be sourced from renal adipose to be used in a formulation to be administered to the kidney.

In one aspect, the present disclosure provides formulations containing certain subfractions of a heterogeneous population of renal cells, enriched for bioactive components and depleted of inactive or undesired components provide superior therapeutic and regenerative outcomes than the starting population. For example, bioactive renal cells described herein, e.g., B2, B4, and B3, which are depleted of inactive or undesired components, e.g., B1 and B5, alone or admixed, can be part of a formulation to be used for the stabilization and/or improvement and/or regeneration of kidney function.

In another aspect, the formulations contain a specific subfraction, B4, depleted of or deficient in one or more cell types, e.g., vascular, endocrine, or endothelial, i.e., B4', that retain therapeutic properties, e.g., stabilization and/or improvement and/or regeneration of kidney function, alone or when admixed with other bioactive subfractions, e.g., B2 and/or B3. In a preferred embodiment, the bioactive cell population is B2. In certain embodiments, the B2 cell population is admixed with B4 or B4'. In other embodiments, the B2 cell population is admixed with B3. In other embodiments, the B2 cell population is admixed with both B3 and B4, or specific cellular components of B3 and/or B4.

The B2 cell population is characterized by expression of a tubular cell marker selected from the group consisting of one or more of the following: megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8), and collecting duct marker Aquaporin-4 (Aqp4). B2 is larger and more granulated than B3 and/or B4 and thus having a buoyant density between about 1.045 g/ml and about 1.063 g/ml (rodent), between about 1.045 g/ml and 1.052 g/ml (human), and between about 1.045 g/ml and about 1.058 g/ml (canine).

The B3 cell population is characterized by the expression of vascular, glomerular and proximal tubular markers with some EPO-producing cells, being of an intermediate size and granularity in comparison to B2 and B4, and thus having a buoyant density between about 1.063 g/ml and about 1.073 g/ml (rodent), between about 1.052 g/ml and about 1.063 g/ml (human), and between about 1.058 g/ml and about 1.063 g/ml (canine). B3 is characterized by expression of markers selected from the group consisting of one or more of the following: aquaporin 7 (Aqp7), FXYD domain-containing ion transport regulator 2 (Fxyd2), solute carrier family 17 (sodium phosphate), member 3 (Slc17a3), solute carrier family 3, member 1 (Slc3a1), claudin 2 (Cldn2), napsin A aspartic peptidase (Napsa), solute carrier family 2 (facilitated glucose transporter), member 2 (Slc2a2), alanyl (membrane) aminopeptidase (Anpep), transmembrane protein 27 (Tmem27), acyl-CoA synthetase medium-chain family member 2 (Acsm2), glutathione peroxidase 3 (Gpx3), fructose-1,6-biphosphatase 1 (Fbp1), and alanine-glyoxylate aminotransferase 2 (Agxt2). B3 is also characterized by the vascular expression marker Platelet endothelial cell adhesion molecule (Pecam) and the glomerular expression marker podocin (Podn).

The B4 cell population is characterized by the expression of a vascular marker set containing one or more of the following: PECAM, VEGF, KDR, HIF1a, CD31, CD146; a glomerular marker set containing one or more of the following: Podocin (Podn), and Nephrin (Neph); and an oxygen-tunable EPO enriched population compared to unfractionated (UNFX), B2 and B3. B4 is also characterized by the expression of one or more of the following markers: chemokine (C-X-C motif) receptor 4 (Cxcr4), endothelin receptor type B (Ednrb), collagen, type V, alpha 2 (Col5a2), Cadherin 5 (CdhS), plasminogen activator, tissue (Plat), angiopoietin 2 (Angpt2), kinase insert domain protein receptor (Kdr), secreted protein, acidic, cysteine-rich (osteonectin) (Sparc), serglycin (Srgn), TIMP metallopeptidase inhibitor 3 (Timp3), Wilms tumor 1 (Wt1), wingless-type MMTV integration site family, member 4 (Wnt4), regulator of G-protein signaling 4 (Rgs4), Platelet endothelial cell adhesion molecule (Pecam), and Erythropoietin (Epo). B4 is also characterized by smaller, less granulated cells compared to either B2 or B3, with a buoyant density between about 1.073 g/ml and about 1.091 g/ml (rodent), between about 1.063 g/ml and about 1.091 g/mL (human and canine).

The B4' cell population is defined as having a buoyant density of between 1.063 g/mL and 1.091 g/mL and expressing one or more of the following markers: PECAM, vEGF, KDR, HIF1a, podocin, nephrin, EPO, CK7, CK8/18/19. In one embodiment, the B4' cell population is characterized by the expression of a vascular marker set containing one or more of the following: PECAM, vEGF, KDR, HIF1a, CD31, CD146. In another embodiment, the B4' cell population is characterized by the expression of an endocrine marker EPO. In one embodiment, the B4' cell population is characterized by the expression of a glomerular marker set containing one or more of the following: Podocin (Podn), and Nephrin (Neph). In certain embodiments, the B4' cell population is characterized by the expression of a vascular marker set containing one or more of the following: PECAM, vEGF, KDR, HIF1a and by the expression of an endocrine marker EPO. In another embodiment, B4' is also characterized by smaller, less granulated cells compared to either B2 or B3, with a buoyant density between about 1.073 g/ml and about 1.091 g/ml (rodent), between about 1.063 g/ml and about 1.091 g/mL (human and canine).

In one aspect, the present disclosure provides formulations containing an isolated, enriched B4' population of human renal cells comprising at least one of erythropoietin (EPO)-producing cells, vascular cells, and glomerular cells having a density between 1.063 g/mL and 1.091 g/mL. In one embodiment, the B4' cell population is characterized by expression of a vascular marker. In certain embodiments, the B4' cell population is not characterized by expression of a glomerular marker. In some embodiments, the B4' cell population is capable of oxygen-tunable erythropoietin (EPO) expression.

In one embodiment, formulation contains the B4' cell population but does not include a B2 cell population comprising tubular cells having a density between 1.045 g/mL and 1.052 g/mL. In another embodiment, the B4' cell population formulation does not include a B1 cell population comprising large granular cells of the collecting duct and tubular system having a density of <1.045 g/ml. In yet another embodiment, the B4' cell population formulation does not include a B5 cell population comprising debris and small cells of low granularity and viability with a density >1.091 g/ml.

In one embodiment, the B4' cell population-containing formulation does not include a B2 cell population comprising tubular cells having a density between 1.045 g/mL and 1.052 g/mL; a B1 cell population comprising large granular cells of the collecting duct and tubular system having a density of <1.045 g/ml; and a B5 cell population comprising debris and small cells of low granularity and viability with a density >1.091 g/ml. In some embodiments, the B4' cell population may be derived from a subject having kidney disease.

In one aspect, the present disclosure provides formulations containing admixtures of human renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between about 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiment, the B4' cell population is characterized by expression of a vascular marker. In one embodiment, the B4' cell population is not characterized by expression of a glomerular marker. In certain embodiments, B2 further comprises collecting duct epithelial cells. In one embodiment, the formulation contains an admixture of cells that is capable of receptor-mediated albumin uptake. In another embodiment, the admixture of cells is capable of oxygen-tunable erythropoietin (EPO) expression. In one embodiment, the admixture contains HAS-2-expressing cells capable of producing and/or stimulating the production of high-molecular weight species of hyaluronic acid (HA) both in vitro and in vivo. In all embodiments, the first and second cell populations may be derived from kidney tissue or cultured kidney cells (Basu et al. Lipids in Health and Disease, 2011, 10:171).

In one embodiment, the formulation contains an admixture that is capable of providing a regenerative stimulus upon in vivo delivery. In other embodiments, the admixture is capable of reducing the decline of, stabilizing, or improving glomerular filtration, tubular resorption, urine production, and/or endocrine function upon in vivo delivery. In one embodiment, the B4' cell population is derived from a subject having kidney disease.

In one aspect, the present disclosure provides formulations containing an isolated, enriched B4' population of human renal cells comprising at least one of erythropoietin (EPO)-producing cells, vascular cells, and glomerular cells having a density between 1.063 g/mL and 1.091 g/mL. In one embodiment, the B4' cell population is characterized by expression of a vascular marker. In certain embodiments, the B4' cell population is not characterized by expression of a glomerular marker. The glomerular marker that is not expressed may be podocin. In some embodiments, the B4' cell population is capable of oxygen-tunable erythropoietin (EPO) expression.

In one embodiment, the B4' cell population-containing formulation does not include a B2 cell population comprising tubular cells having a density between 1.045 g/mL and 1.052 g/mL. In another embodiment, the B4' cell population formulation does not include a B1 cell population comprising large granular cells of the collecting duct and tubular system having a density of <1.045 g/ml. In yet another embodiment, the B4' cell population formulation does not include a B5 cell population comprising debris and small cells of low granularity and viability with a density >1.091 g/ml.

In one embodiment, the B4' cell population-containing formulation does not include a B2 cell population comprising tubular cells having a density between 1.045 g/mL and 1.052 g/mL; a B1 cell population comprising large granular cells of the collecting duct and tubular system having a density of <1.045 g/ml; and a B5 cell population comprising debris and small cells of low granularity and viability with a density >1.091 g/ml. In some embodiments, the B4' cell population may be derived from a subject having kidney disease.

In one aspect, the present disclosure provides formulations containing an admixture of human renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between about 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiment, the B4' cell population is characterized by expression of a vascular marker. In one embodiment, the B4' cell population is not characterized by expression of a glomerular marker. In certain embodiments, B2 further comprises collecting duct epithelial cells. In one embodiment, the admixture of cells is capable of receptor-mediated albumin uptake. In another embodiment, the admixture of cells is capable of oxygen-tunable erythropoietin (EPO) expression. In one embodiment, the admixture contains HAS-2-expressing cells capable of producing and/or stimulating the production of high-molecular weight species of hyaluronic acid (HA) both in vitro and in vivo. In all embodiments, the first and second cell populations may be derived from kidney tissue or cultured kidney cells.

In another aspect, the present disclosure provides formulations containing a heterogeneous renal cell population comprising a combination of cell fractions or enriched cell populations (e.g., B1, B2, B3, B4 (or B4'), and B5). In one embodiment, the combination has a buoyant density between about 1.045 g/ml and about 1.091 g/ml. In one other embodiment, the combination has a buoyant density between less than about 1.045 g/ml and about 1.099 g/ml or about 1.100 g/ml. In another embodiment, the combination has a buoyant density as determined by separation on a density gradient, e.g., by centrifugation. In yet another embodiment, the combination of cell fractions contains B2, B3, and B4 (or B4') depleted of B1 and/or B5. In some embodiments, the combination of cell fractions contains B2, B3, B4 (or B4'), and B5 but is depleted of B1. Once depleted of B1 and/or B5, the combination may be subsequently cultured in vitro prior to the preparation of a formulation comprising the combination of B2, B3, and B4 (or B4') cell fractions.

The inventors of the present disclosure have surprisingly discovered that in vitro culturing of a B1-depleted combination of B2, B3, B4, and B5 results in depletion of B5. In one embodiment, B5 is depleted after at least one, two, three, four, or five passages. In one other embodiment, the B2, B3, B4, and B5 cell fraction combination that is passaged under the conditions described herein provides a passaged cell population having B5 at a percentage that is less than about 5%, less than about 4%, less than about 3%, less than about 2%, less than about 1%, or less than about 0.5% of the passaged cell population.

In another embodiment, B4' is part of the combination of cell fractions. In one other embodiment, the in vitro culturing depletion of B5 is under hypoxic conditions.

In one embodiment, the formulation contains an admixture that is capable of providing a regenerative stimulus upon in vivo delivery. In other embodiments, the admixture is capable of reducing the decline of, stabilizing, or improving glomerular filtration, tubular resorption, urine production, and/or endocrine function upon in vivo delivery. In one embodiment, the B4' cell population is derived from a subject having kidney disease.

In a preferred embodiment, the formulation contains an admixture that comprises B2 in combination with B3 and/or B4. In another preferred embodiment, the admixture comprises B2 in combination with B3 and/or B4'. In other preferred embodiments, the admixture consists of or consists essentially of (i) B2 in combination with B3 and/or B4; or (ii) B2 in combination with B3 and/or B4'.

The admixtures that contain a B4' cell population may contain B2 and/or B3 cell populations that are also obtained from a non-healthy subject. The non-healthy subject may be the same subject from which the B4' fraction was obtained. In contrast to the B4' cell population, the B2 and B3 cell populations obtained from non-healthy subjects are typically not deficient in one or more specific cell types as compared to a starting kidney cell population derived from a healthy individual.

As described in Presnell et al. WO/2010/056328, it has been found that the B2 and B4 cell preparations are capable of expressing higher molecular weight species of hyaluronic acid (HA) both in vitro and in vivo, through the actions of hyaluronic acid synthase-2 (HAS-2)—a marker that is enriched more specifically in the B2 cell population. Treatment with B2 in a 5/6 Nx model was shown to reduce fibrosis, concomitant with strong expression HAS-2 expression in vivo and the expected production of high-molecular-weight HA within the treated tissue. Notably, the 5/6 Nx model left untreated resulted in fibrosis with limited detection of HAS-2 and little production of high-molecular-weight HA. Without wishing to be bound by theory, it is hypothesized that this anti-inflammatory high-molecular weight species of HA produced predominantly by B2 (and to some degree by B4) acts synergistically with the cell preparations in the reduction of renal fibrosis and in the aid of renal regeneration. Accordingly, the instant disclosure includes formulations containing the bioactive renal cells described herein along with a biomaterial comprising hyaluronic acid. Also contemplated by the instant disclosure is the provision of a biomaterial component of the regenerative stimulus via direct production or stimulation of production by the implanted cells.

In one aspect, the present disclosure provides formulations that contain isolated, heterogeneous populations of EPO-producing kidney cells for use in the treatment of kidney disease, anemia and/or EPO deficiency in a subject in need. In one embodiment, the cell populations are derived from a kidney biopsy. In another embodiment, the cell populations are derived from whole kidney tissue. In one other embodiment, the cell populations are derived from in vitro cultures of mammalian kidney cells, established from kidney biopsies or whole kidney tissue. In all embodiments, these populations are unfractionated cell populations, also referred to herein as non-enriched cell populations.

In another aspect, the present disclosure provides formulations that contain isolated populations of erythropoietin (EPO)-producing kidney cells that are further enriched such that the proportion of EPO-producing cells in the enriched subpopulation is greater relative to the proportion of EPO-producing cells in the starting or initial cell population. In one embodiment, the enriched EPO-producing cell fraction contains a greater proportion of interstitial fibroblasts and a lesser proportion of tubular cells relative to the interstitial fibroblasts and tubular cells contained in the unenriched initial population. In certain embodiments, the enriched EPO-producing cell fraction contains a greater proportion of glomerular cells and vascular cells and a lesser proportion of collecting duct cells relative to the glomerular cells, vascular cells and collecting duct cells contained in the unenriched initial population. In such embodiments, these populations are referred to herein as the "B4" cell population.

In another aspect, the present disclosure provides formulations containing an EPO-producing kidney cell population that is admixed with one or more additional kidney cell populations. In one embodiment, the EPO-producing cell population is a first cell population enriched for EPO-producing cells, e.g., B4. In another embodiment, the EPO-producing cell population is a first cell population that is not enriched for EPO-producing cells, e.g., B2. In another embodiment, the first cell population is admixed with a second kidney cell population. In some embodiments, the second cell population is enriched for tubular cells, which may be demonstrated by the presence of a tubular cell phenotype. In another embodiment, the tubular cell phenotype may be indicated by the presence of one tubular cell marker. In another embodiment, the tubular cell phenotype may be indicated by the presence of one or more tubular cell markers. The tubular cell markers include, without limitation, megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8). In another embodiment, the first cell population is admixed with at least one of several types of kidney cells including, without limitation, interstitium-derived cells, tubular cells, collecting duct-derived cells, glomerulus-derived cells, and/or cells derived from the blood or vasculature.

The formulations of the present disclosure may include EPO-producing kidney cell populations containing B4 or B4' in the form of an admixture with B2 and/or B3, or in the form of an enriched cell population, e.g., B2+B3+B4/B4'.

In one aspect, the formulation contains EPO-producing kidney cell populations that are characterized by EPO expression and bioresponsiveness to oxygen, such that a reduction in the oxygen tension of the culture system results in an induction in the expression of EPO. In one embodiment, the EPO-producing cell populations are enriched for EPO-producing cells. In one embodiment, the EPO expression is induced when the cell population is cultured under conditions where the cells are subjected to a reduction in available oxygen levels in the culture system as compared to a cell population cultured at normal atmospheric (~21%) levels of available oxygen. In one embodiment, EPO-producing cells cultured in lower oxygen conditions express greater levels of EPO relative to EPO-producing cells cultured at normal oxygen conditions. In general, the culturing of cells at reduced levels of available oxygen (also referred to as hypoxic culture conditions) means that the level of reduced oxygen is reduced relative to the culturing of cells at normal atmospheric levels of available oxygen (also referred to as normal or normoxic culture conditions). In one embodiment, hypoxic cell culture conditions include culturing cells at about less than 1% oxygen, about less than 2% oxygen, about less than 3% oxygen, about less than 4% oxygen, or about less than 5% oxygen. In another embodiment, normal or normoxic culture conditions include culturing cells at about 10% oxygen, about 12% oxygen, about 13% oxygen, about 14% oxygen, about 15% oxygen, about 16% oxygen, about 17% oxygen, about 18% oxygen, about 19% oxygen, about 20% oxygen, or about 21% oxygen.

In one other embodiment, induction or increased expression of EPO is obtained and can be observed by culturing cells at about less than 5% available oxygen and comparing EPO expression levels to cells cultured at atmospheric (about 21%) oxygen. In another embodiment, the induction of EPO is obtained in a culture of cells capable of expressing EPO by a method that includes a first culture phase in which the culture of cells is cultivated at atmospheric oxygen (about 21%) for some period of time and a second culture phase in which the available oxygen levels are reduced and the same cells are cultured at about less than 5% available oxygen. In another embodiment, the EPO expression that is responsive to hypoxic conditions is regulated by HIF1α. Those of ordinary skill in the art will appreciate that other oxygen manipulation culture conditions known in the art may be used for the cells described herein.

In one aspect, the formulation contains enriched populations of EPO-producing mammalian cells characterized by bio-responsiveness (e.g., EPO expression) to perfusion conditions. In one embodiment, the perfusion conditions include transient, intermittent, or continuous fluid flow (perfusion). In one embodiment, the EPO expression is mechanically-induced when the media in which the cells are cultured is intermittently or continuously circulated or agitated in such a manner that dynamic forces are transferred to the cells via the flow. In one embodiment, the cells subjected to the transient, intermittent, or continuous fluid flow are cultured in such a manner that they are present as three-dimensional structures in or on a material that provides framework and/or space for such three-dimensional structures to form. In one embodiment, the cells are cultured on porous beads and subjected to intermittent or continuous fluid flow by means of a rocking platform, orbiting platform, or spinner flask. In another embodiment, the cells are cultured on three-dimensional scaffolding and placed into a device whereby the scaffold is stationary and fluid flows directionally through or across the scaffolding. Those of ordinary skill in the art will appreciate that other perfusion culture conditions known in the art may be used for the cells described herein.

Cellular Aggregates

In one other aspect, the formulations of the present disclosure contain cellular aggregates or spheroids. In one embodiment, the cellular aggregate comprises a bioactive cell population described herein. In another embodiment, the cellular aggregate comprises bioactive renal cells such as, for example, renal cell admixtures, enriched renal cell populations, and combinations of renal cell fractions.

In certain embodiments, the bioactive renal cells of the disclosure may be cultured in 3D formats as described further herein. In some embodiments, the term "organoid" refers to an accumulation of cells, with a phenotype and/or function, consistent with a native kidney. In some embodiments, organoids comprise mixed populations of cells, of a variety of lineages, which are typically found in vivo in a given tissue. In some embodiments, the organoids of this disclosure are formed in vitro, via any means, whereby the cells of the disclosure form aggregates, which in turn may form spheroids, organoids, or a combination thereof. Such aggregates, spheroids or organoids, in some embodiments, assume a structure consistent with a particular organ. In some embodiments, such aggregates, spheroids or organoids, express surface markers, which are typically expressed by cells of the particular organ. In some embodiments, such aggregates, spheroids or organoids, produce compounds or materials, which are typically expressed by cells of the particular organ. In certain embodiments, the cells of the disclosure may be cultured on natural substrates, e.g., gelatin. In other embodiments, the cells of the disclosure may be cultured on synthetic substrates, e.g., PGLA.

Inactive Cell Populations

As described herein, certain subfractions of a heterogeneous population of renal cells, enriched for bioactive components and depleted of inactive or undesired components, provide superior therapeutic and regenerative outcomes than the starting population. In preferred embodiments, the formulations provided by the present disclosure contain cellular populations that are depleted of B1 and/or B5 cell populations. For instance, the following may be depleted of B1 and/or B5: admixtures of two or more of B2, B3, and B4 (or B4'); an enriched cell population of B2, B3, and B4 (or B4').

The B1 cell population comprises large, granular cells of the collecting duct and tubular system, with the cells of the population having a buoyant density less than about 1.045 g/m. The B5 cell population is comprised of debris and small cells of low granularity and viability and having a buoyant density greater than about 1.091 g/ml.

Methods of Isolating and Culturing Cell Populations

In one aspect, the formulations of the present disclosure contain cell populations that have been isolated and/or cultured from kidney tissue. Methods are provided herein for separating and isolating the renal cellular components, e.g., enriched cell populations that will be used in the formulations for therapeutic use, including the treatment of kidney disease, anemia, EPO deficiency, tubular transport deficiency, and glomerular filtration deficiency. In one embodiment, the cell populations are isolated from freshly digested, i.e., mechanically or enzymatically digested, kidney tissue or from heterogeneous in vitro cultures of mammalian kidney cells.

The formulations may contain heterogeneous mixtures of renal cells that have been cultured in hypoxic culture conditions prior to separation on a density gradient provides for enhanced distribution and composition of cells in both B4, including B4', and B2 and/or B3 fractions. The enrichment of oxygen-dependent cells in B4 from B2 was observed for renal cells isolated from both diseased and non-diseased kidneys. Without wishing to be bound by theory, this may be due to one or more of the following phenomena: 1) selective survival, death, or proliferation of specific cellular components during the hypoxic culture period; 2) alterations in cell granularity and/or size in response to the hypoxic culture, thereby effecting alterations in buoyant density and subsequent localization during density gradient separation; and 3) alterations in cell gene/protein expression in response to the hypoxic culture period, thereby resulting in differential characteristics of the cells within any given fraction of the gradient. Thus, in one embodiment, the formulations contain cell populations enriched for tubular cells, e.g., B2, are hypoxia-resistant.

Exemplary techniques for separating and isolating the cell populations include separation on a density gradient based on the differential specific gravity of different cell types contained within the population of interest. The specific gravity of any given cell type can be influenced by the degree of granularity within the cells, the intracellular volume of water, and other factors. In one aspect, the present disclosure provides optimal gradient conditions for isolation of the cell preparations, e.g., B2 and B4, including B4', across multiple species including, but not limited to, human, canine, and rodent. In a preferred embodiment, a density gradient is used to obtain a novel enriched population of tubular cells fraction, i.e., B2 cell population, derived from a heterogeneous population of renal cells. In one embodiment, a density gradient is used to obtain a novel enriched population of EPO-producing cells fraction, i.e., B4 cell population, derived from a heterogeneous population of renal cells. In other embodiments, a density gradient is used to obtain enriched subpopulations of tubular cells, glomerular cells, and endothelial cells of the kidney. In one embodiment, both the EPO-producing and the tubular cells are separated from the red blood cells and cellular debris. In one embodiment, the EPO-producing, glomerular, and vascular cells are separated from other cell types and from red blood cells and cellular debris, while a subpopulation of tubular cells and collecting duct cells are concomitantly separated from other cell types and from red blood cells and cellular debris. In one other embodiment, the endocrine, glomerular, and/or vascular cells are separated from other cell types and from red blood cells and cellular debris, while a subpopulation of tubular cells and collecting duct cells are concomitantly separated from other cell types and from red blood cells and cellular debris.

In one aspect, the formulations of the present disclosure contain cell populations generated by using, in part, the OPTIPREP® (Axis-Shield) density gradient medium, comprising 60% nonionic iodinated compound iodixanol in water, based on certain key features described below. One of skill in the art, however, will recognize that any density gradient or other means, e.g., immunological separation using cell surface markers known in the art, comprising necessary features for isolating the cell populations of the instant disclosure may be used. It should also be recognized by one skilled in the art that the same cellular features that contribute to separation of cellular subpopulations via density gradients (size and granularity) can be exploited to separate cellular subpopulations via flow cytometry (forward scatter=a reflection of size via flow cytometry, and side scatter=a reflection of granularity). Importantly, the density gradient medium should have low toxicity towards the specific cells of interest. While the density gradient medium should have low toxicity toward the specific cells of interest, the instant disclosure contemplates the use of gradient mediums which play a role in the selection process of the cells of interest. Without wishing to be bound by theory, it appears that the cell populations disclosed hereinrecovered by the gradient comprising iodixanol are iodixanol-resistant, as there is an appreciable loss of cells between the loading and recovery steps, suggesting that exposure to iodixanol under the conditions of the gradient leads to elimination of certain cells. The cells appearing in the specific bands after the iodixanol gradient are resistant to any untoward effects of iodixanol and/or density gradient exposure. Accordingly, the use of additional contrast media which are mild to moderate nephrotoxins in the isolation and/or selection of the cell populations for the formulations described herein is also contemplated. In addition, the density gradient medium should also not bind to proteins in human plasma or adversely affect key functions of the cells of interest.

In another aspect, the present disclosure provides formulations containing cell populations that have been enriched and/or depleted of kidney cell types using fluorescent activated cell sorting (FACS). In one embodiment, kidney cell types may be enriched and/or depleted using BD FACSAria™ or equivalent.

In another aspect, the formulations contain cell populations that have been enriched and/or depleted of kidney cell types using magnetic cell sorting. In one embodiment, kidney cell types may be enriched and/or depleted using the Miltenyi autoMACS® system or equivalent.

In another aspect, the formulations may include renal cell populations that have been subject to three-dimensional culturing. In one aspect, the methods of culturing the cell populations are via continuous perfusion. In one embodiment, the cell populations cultured via three-dimensional culturing and continuous perfusion demonstrate greater cellularity and interconnectivity when compared to cell populations cultured statically. In another embodiment, the cell populations cultured via three dimensional culturing and continuous perfusion demonstrate greater expression of EPO, as well as enhanced expression of renal tubule-associate genes such as e-cadherin when compared to static cultures of such cell populations. In yet another embodiment, the cell populations cultured via continuous perfusion demonstrate greater levels of glucose and glutamine consumption when compared to cell populations cultured statically.

As described herein, low or hypoxic oxygen conditions may be used in the methods to prepare the cell populations for the formulations provided for herein. However, the methods of preparing cell populations may be used without the step of low oxygen conditioning. In one embodiment, normoxic conditions may be used.

Those of ordinary skill in the art will appreciate that other methods of isolation and culturing known in the art may be used for the cells described herein.

3. Biomaterials

A variety of biomaterials may be combined with an active agent to provide the therapeutic formulations of the present disclosure. The biomaterials may be in any suitable shape (e.g., beads) or form (e.g., liquid, gel, etc.). As described in Bertram et al. U.S. Published Application 20070276507 (incorporated herein by reference in its entirety), polymeric matrices or scaffolds may be shaped into any number of desirable configurations to satisfy any number of overall system, geometry or space restrictions. In one embodiment, the matrices or scaffolds of the present disclosure may be three-dimensional and shaped to conform to the dimensions and shapes of an organ or tissue structure. For example, in the use of the polymeric scaffold for treating kidney disease, anemia, EPO deficiency, tubular transport deficiency, or glomerular filtration deficiency, a three-dimensional (3-D) matrix may be used. A variety of differently shaped 3-D scaffolds may be used. Naturally, the polymeric matrix may be shaped in different sizes and shapes to conform to differently sized patients. The polymeric matrix may also be shaped in other ways to accommodate the special needs of the patient. In another embodiment, the polymeric matrix or scaffold may be a biocompatible, porous polymeric scaffold. The scaffolds may be formed from a variety of synthetic or naturally-occurring materials including, but not limited to, open-cell polylactic acid (OPLA®), cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, collagens, gelatin, alginate, laminins, fibronectin, silk, elastin, alginate, hyaluronic acid, agarose, or copolymers or physical blends thereof. Scaffolding configurations may range from liquid suspensions to soft porous scaffolds to rigid, shape-holding porous scaffolds. In one embodiment, the configuration is the liquid form of a solution that is capable of becoming a hydrogel.

Hydrogels may be formed from a variety of polymeric materials and are useful in a variety of biomedical applications. Hydrogels can be described physically as three-dimensional networks of hydrophilic polymers. Depending on the type of hydrogel, they contain varying percentages of water, but altogether do not dissolve in water. Despite their high water content, hydrogels are capable of additionally binding great volumes of liquid due to the presence of hydrophilic residues. Hydrogels swell extensively without changing their gelatinous structure. The basic physical features of hydrogel can be specifically modified, according to the properties of the polymers used and the additional special equipments of the products.

Preferably, the hydrogel is made of a polymer, a biologically derived material, a synthetically derived material or combinations thereof, that is biologically inert and physiologically compatible with mammalian tissues. The hydrogel material preferably does not induce an inflammatory response. Examples of other materials which can be used to form a hydrogel include (a) modified alginates, (b) polysaccharides (e.g. gellan gum and carrageenans) which gel by exposure to monovalent cations, (c) polysaccharides (e.g., hyaluronic acid) that are very viscous liquids or are thixotropic and form a gel over time by the slow evolution of structure, (d) gelatin or collagen, and (e) polymeric hydrogel precursors (e.g., polyethylene oxide-polypropylene glycol block copolymers and proteins). U.S. Pat. No. 6,224,893 B1 provides a detailed description of the various polymers, and the chemical properties of such polymers, that are suitable for making hydrogels.

Scaffolding or biomaterial characteristics may enable cells to attach and interact with the scaffolding or biomaterial material, and/or may provide porous spaces into which cells can be entrapped. In one embodiment, the porous scaffolds or biomaterials allow for the addition or deposition of one or more populations or admixtures of cells on a biomaterial configured as a porous scaffold (e.g., by attachment of the cells) and/or within the pores of the scaffold (e.g., by entrapment of the cells). In another embodiment, the scaffolds or biomaterials allow or promote for cell:cell and/or cell:biomaterial interactions within the scaffold to form constructs as described herein.

In one embodiment, the biomaterial is comprised of hyaluronic acid (HA) in hydrogel form, containing HA molecules ranging in size from 5.1 kDA to >2×10$^6$ kDa. In another embodiment, the biomaterial is comprised of hyaluronic acid in porous foam form, also containing HA molecules ranging in size from 5.1 kDA to >2×10$^6$ kDa. In yet another embodiment, the biomaterial is comprised of a poly-lactic acid (PLA)-based foam, having an open-cell structure and pore size of about 50 microns to about 300 microns. In yet another embodiment, the specific cell populations, preferentially B2 but also B4, provide directly and/or stimulate synthesis of high molecular weight Hyaluronic Acid through Hyaluronic Acid Synthase-2 (HAS-2), especially after intra-renal implantation.

The biomaterials described herein may also be designed or adapted to respond to certain external conditions, e.g., in vitro or in vivo. In one embodiment, the biomaterials are temperature-sensitive (e.g., either in vitro or in vivo). In another embodiment, the biomaterials are adapted to respond to exposure to enzymatic degradation (e.g., either in vitro or in vivo). The biomaterials' response to external conditions can be fine tuned as described herein. Temperature sensitivity of the formulation described can be varied by adjusting the percentage of a biomaterial in the formulation. For example, the percentage of gelatin in a solution can be adjusted to modulate the temperature sensitivity of the gelatin in the final formulation (e.g., liquid, gel, beads, etc.). Alternatively, biomaterials may be chemically cross-linked to provide greater resistance to enzymatic degradation. For instance, a carbodiimide crosslinker may be used to chemically crosslink gelatin beads thereby providing a reduced susceptibility to endogenous enzymes.

In one aspect, the response by the biomaterial to external conditions concerns the loss of structural integrity of the biomaterial. Although temperature-sensitivity and resistance to enzymatic degradation are provided above, other mechanisms exist by which the loss of material integrity may occur in different biomaterials. These mechanisms may include, but are not limited to thermodynamic (e.g., a phase transition such as melting, diffusion (e.g., diffusion of an ionic cross-linker from a biomaterial into the surrounding tissue)), chemical, enzymatic, pH (e.g., pH-sensitive liposomes), ultrasound, and photolabile (light penetration). The exact mechanism by which the biomaterial loses structural integrity will vary but typically the mechanism is triggered either at the time of implantation or post-implantation.

Those of ordinary skill in the art will appreciate that other types of synthetic or naturally-occurring materials known in the art may be used to form scaffolds as described herein.

In one aspect, the constructs as described herein are made from the above-referenced scaffolds or biomaterials.

4. Constructs

In one aspect, the disclosure provides formulations that contain implantable constructs having one or more of the cell populations described herein for the treatment of kidney disease, anemia, or EPO deficiency in a subject in need. In one embodiment, the construct is made up of a biocompatible material or biomaterial, scaffold or matrix composed of one or more synthetic or naturally-occurring biocompatible materials and one or more cell populations or admixtures of cells described herein deposited on or embedded in a surface of the scaffold by attachment and/or entrapment. In certain embodiments, the construct is made up of a biomaterial and one or more cell populations or admixtures of cells described herein coated with, deposited on, deposited in, attached to, entrapped in, embedded in, seeded, or combined with the biomaterial component(s). Any of the cell populations described herein, including enriched cell populations or admixtures thereof, may be used in combination with a matrix to form a construct.

In one aspect, the formulation contains constructs that are made up of biomaterials designed or adapted to respond to external conditions as described herein. As a result, the nature of the association of the cell population with the biomaterial in a construct will change depending upon the external conditions. For example, a cell population's association with a temperature-sensitive biomaterial varies with temperature. In one embodiment, the construct contains a cell population and biomaterial having a substantially solid state at about 8° C. or lower and a substantially liquid state at about ambient temperature or above, wherein the cell population is suspended in the biomaterial at about 8° C. or lower.

However, the cell population is substantially free to move throughout the volume of the biomaterial at about ambient temperature or above. Having the cell population suspended in the substantially solid phase at a lower temperature provides stability advantages for the cells, such as for anchorage-dependent cells, as compared to cells in a fluid. Moreover, having cells suspended in the substantially solid state provides one or more of the following benefits: i) prevents settling of the cells, ii) allows the cells to remain anchored to the biomaterial in a suspended state; iii) allows the cells to remain more uniformly dispersed throughout the volume of the biomaterial; iv) prevents the formation of cell aggregates; and v) provides better protection for the cells during storage and transportation of the formulation. A formulation that can retain such features leading up to the administration to a subject is advantageous at least because the overall health of the cells in the formulation will be better and a more uniform and consistent dosage of cells will be administered.

In another embodiment, the deposited cell population or cellular component of the construct is a first kidney cell population enriched for oxygen-tunable EPO-producing cells. In another embodiment, the first kidney cell population contains glomerular and vascular cells in addition to the oxygen-tunable EPO-producing cells. In one embodiment, the first kidney cell population is a B4' cell population. In one other embodiment, the deposited cell population or cellular component(s) of the construct includes both the first enriched renal cell population and a second renal cell population. In some embodiments, the second cell population is not enriched for oxygen-tunable EPO producing cells. In another embodiment, the second cell population is enriched for renal tubular cells. In another embodiment, the second cell population is enriched for renal tubular cells and contains collecting duct epithelial cells. In other embodiments, the renal tubular cells are characterized by the expression of one or more tubular cell markers that may include, without limitation, megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8).

In one embodiment, the cell populations deposited on or combined with biomaterials or scaffolds to form constructs are derived from a variety of sources, such as autologous sources. Non-autologous sources are also suitable for use, including without limitation, allogeneic, or syngeneic (autogeneic or isogeneic) sources.

Those of ordinary skill in the art will appreciate there are several suitable methods for depositing or otherwise combining cell populations with biomaterials to form a construct.

In one aspect, the constructs are suitable for use in the methods of use described herein. In one embodiment, the constructs are suitable for administration to a subject in need of treatment for a kidney disease of any etiology, anemia, or EPO deficiency of any etiology. In other embodiments, the constructs are suitable for administration to a subject in need of an improvement in or restoration of erythroid homeostasis. In another embodiment, the constructs are suitable for administration to a subject in need of improved kidney function.

In yet another aspect, the present disclosure provides a construct for implantation into a subject in need of improved kidney function comprising: a) a biomaterial comprising one or more biocompatible synthetic polymers or naturally-occurring proteins or peptides; and b) an admixture of mammalian renal cells derived from a subject having kidney disease comprising a first cell population, B2, comprising an isolated, enriched population of tubular cells having a density between 1.045 g/mL and 1.052 g/mL and a second cell population, B4', comprising erythropoietin (EPO)-producing cells and vascular cells but depleted of glomerular cells having a density between 1.063 g/mL and 1.091 g/mL, coated with, deposited on or in, entrapped in, suspended in, embedded in and/or otherwise combined with the biomaterial. In certain embodiments, the admixture does not include a B1 cell population comprising large granular cells of the collecting duct and tubular system having a density of <1.045 g/ml, or a B5 cell population comprising debris and small cells of low granularity and viability with a density >1.091 g/ml.

In one embodiment, the construct includes a B4' cell population which is characterized by expression of a vascular marker. In some embodiments, the B4' cell population is not characterized by expression of a glomerular marker. In certain embodiments, the admixture is capable of oxygen-tunable erythropoietin (EPO) expression. In all embodiments, the admixture may be derived from mammalian kidney tissue or cultured kidney cells.

In one embodiment, the construct includes a biomaterial configured as a three-dimensional (3-D) porous biomaterial suitable for entrapment and/or attachment of the admixture. In another embodiment, the construct includes a biomaterial configured as a liquid or semi-liquid gel suitable for embedding, attaching, suspending, or coating mammalian cells. In yet another embodiment, the construct includes a biomaterial configured comprised of a predominantly high-molecular weight species of hyaluronic acid (HA) in hydrogel form. In another embodiment, the construct includes a biomaterial comprised of a predominantly high-molecular weight species of hyaluronic acid in porous foam form. In yet another embodiment, the construct includes a biomaterial comprised of a poly-lactic acid-based foam having pores of between about 50 microns to about 300 microns. In still another embodiment, the construct includes one or more cell populations that may be derived from a kidney sample that is autologous to the subject in need of improved kidney function. In certain embodiments, the sample is a kidney biopsy. In some embodiments, the subject has a kidney disease. In yet other embodiments, the cell population is derived from a non-autologous kidney sample. In one embodiment, the construct provides erythroid homeostasis.

5. Phenotypic Characterization of Renal Cells

The cells isolated at any stage of the process may be characterized by their phenotype. In one embodiment, the cells are a heterogeneous renal cell population that has been enriched. In a further embodiment, the enriched heterogeneous renal cell population has been cultured under hypoxic conditions for at least 24 hours. In a yet further embodiment, the enriched heterogeneous renal cell population has been subjected to a density gradient.

The presence (e.g., expression) and/or level/amount of various biomarkers in a sample can be analyzed by a number of methodologies, many of which are known in the art and understood by the skilled artisan, including, but not limited to, immunohistochemical ("IHC"), Western blot analysis, immunoprecipitation, molecular binding assays, ELISA, ELIFA, fluorescence activated cell sorting ("FACS"), MassARRAY, proteomics, biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery may also be used.

In one aspect, a method of detecting the presence of two or more biomarkers in a heterogeneous renal cell sample is provided, the method comprising contacting the sample with an antibody directed to a biomarker under conditions permissive for binding of the antibody to its cognate ligand (i.e., biomarker), and detecting the presence of the bound antibody, e.g., by detecting whether a complex is formed between the antibody and the biomarker. In some embodiments, the detection of the presence of one or more biomarkers is by immunohistochemistry.

In certain embodiments, any of the antibodies provided herein is useful for detecting the presence of a biomarker in a heterogeneous renal cell sample. The term "detecting" as used herein encompasses quantitative or qualitative detection. In certain embodiments, a biological sample comprises a SRC sample.

In certain embodiments, the heterogeneous renal cells are identified with one or more reagents that allow detection of a biomarker selected from AQP1, AQP2, AQP4, Calbindin, Calponin, CD117, CD133, CD146, CD24, CD31 (PECAM-1), CD54 (ICAM-1), CD73, CK18, CK19, CK40 to 67, CK7, CK8, CK8/18, CK8/18/19, Connexin 43, Cubilin, CXCR4 (Fusin), DBA, E-cadherin (CD324), EPO (erythropoietin), GGT1, GLEPP1 (glomerular epithelial protein 1), Haptoglobulin, Itgb1 (Integrin β1), KIM-1/TIM-1 (kidney injury molecule-1/T-cell immunoglobulin and mucin-containing molecule), MAP-2 (microtubule-associated protein 2), Megalin, N-cadherin, Nephrin, NKCC (Na-K-C1-cotransporters), OAT-1 (organic anion transporter 1), Osteopontin, Pan-cadherin, PCLP1 (podocalyxin-like 1 molecule), Podocin, SMA (smooth muscle alpha-actin), Synaptopodin, THP (tamm-horsfall protein), Vimentin, and αGST-1 (alpha glutathione S-transferase). In certain embodiments, a biomarker is detected by monoclonal or polyclonal antibodies.

In one embodiment, an detectable label comprises a radioactive atom to form a radioconjugate. A variety of radioactive isotopes are available for the production of radioconjugates. Examples include $^{211}At$, $^{131}I$, $^{125}I$, $^{90}Y$, $^{186}Re$, $^{188}Re$, $^{153}Sm$, $^{212}Bi$, $^{32}P$, $^{212}Pb$ and radioactive isotopes of Lu. When the radioconjugate is used for detection, it may comprise a radioactive atom for scintigraphic studies, for example $^{99}Tc$-m (metastable nuclear isomer) or $^{123}I$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

In case more than one detectable label (including a dye) is used in one testing, it is preferred that the detectable labels are selected such that each label can be independently detected without substantial interference to any other detectable signals present in the sample. For example, the detectable labels (including a dye) may be different fluorescent molecules showing different colors under the detection condition.

The detection can be carried out by any suitable method, for example, those based on immunofluorescent microscopy, flow cytometry, fiber-optic scanning cytometry, or laser scanning cytometry.

In some embodiments, the expression of a biomarker in a cell is determined by evaluating mRNA in a cell. Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like). In some embodiments, the expression of a biomarker in a test sample is compared to a reference sample. For example, the test sample may be a diseased tissue sample and the reference sample may be from normal tissue.

Samples from mammals can be conveniently assayed for mRNAs using Northern, dot blot or PCR analysis. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods include protocols which examine or detect mRNAs, such as target mRNAs, in a tissue or cell sample by microarray technologies. Using nucleic acid microarrays, test and control mRNA samples from test and control samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with a cell population capable of eliciting a regenerative response may be arrayed on a solid support. Hybridization of a labeled probe with a particular array member indicates that the sample from which the probe was derived expresses that gene.

According to some embodiments, presence and/or level/amount is measured by observing protein expression levels of an aforementioned gene. In certain embodiments, the method comprises contacting the biological sample with antibodies to a biomarker described herein under conditions permissive for binding of the biomarker, and detecting whether a complex is formed between the antibodies and biomarker.

In certain embodiments, the presence and/or level/amount of biomarker proteins in a sample are examined using IHC and staining protocols. IHC staining of cells has been shown to be a reliable method of determining or detecting the presence of proteins in a sample. In one aspect, level of biomarker is determined using a method comprising: (a) performing IHC analysis of a sample (such as a renal cell sample) with an antibody; and b) determining level of a biomarker in the sample. In some embodiments, IHC staining intensity is determined relative to a reference value.

IHC may be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) Radioisotopes, such as $^{35}$S, $^{14}$C, $^{125}$I, $^{3}$H, and $^{131}$I; (b) colloidal gold particles; (c) fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRP) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see U.S. Pat. Nos. 4,275,149 and 4,318,980.

In an exemplary method, the sample may be contacted with an antibody specific for the biomarker under conditions sufficient for an antibody-biomarker complex to form, and then detecting the complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

The presence and/or level/amount of a selected biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

In certain embodiments, the samples are normalized for both differences in the amount of the biomarker assayed and variability in the quality of the samples used, and variability between assay runs. Such normalization may be accomplished by detecting and incorporating the level of certain normalizing biomarkers, including well known housekeeping genes, such as ACTB. Alternatively, normalization can be based on the mean or median signal of all of the assayed genes or a large subset thereof (global normalization approach). On a gene-by-gene basis, measured normalized amount of a subject tumor mRNA or protein is compared to the amount found in a reference set. Normalized expression levels for each mRNA or protein per tested tumor per subject can be expressed as a percentage of the expression level measured in the reference set. The presence and/or expression level/amount measured in a particular subject sample to be analyzed will fall at some percentile within this range, which can be determined by methods well known in the art.

In embodiments, the cytokeratin is selected from CK8, CK18, CK19 and combinations thereof. In certain embodiments, the cytokeratin is CK8, CK18, CK19, CK8/CK18, CK8/CK19, CK18/CK19 or CK8/CK18/CK19, wherein the "/" refers to a combination of the cytokeratins adjacent thereto. In all embodiments, the cytokeratin has a level of expression greater than about 80%, about 85%, about 90%, or about 95%.

In embodiments, the GGT is GGT-1. In all embodiments the GGT has a level of expression greater than about 10%, about 15%, about 18%, about 20%, about 25%, about 30%, about 35%, about 40%, about 45%, about 50%, about 55%, or about 60%.

6. Methods of Use

In another aspect, the formulations of the present disclosure may be administered for the treatment of disease. For example, bioactive cells may be administered to a native organ as part of a formulation described herein. In one embodiment, the bioactive cells may be sourced from the native organ that is the subject of the administration or from a source that is not the target native organ.

In one aspect, the present disclosure provides methods for the treatment of a kidney disease, anemia, or EPO deficiency in a subject in need with the formulations containing kidney cell populations and admixtures of kidney cells as described herein. In one embodiment, the method comprises administering to the subject a formulation containing a composition that includes a first kidney cell population enriched for EPO-producing cells. In another embodiment, the first cell population is enriched for EPO-producing cells, glomerular cells, and vascular cells. In one embodiment, the first kidney cell population is a B4' cell population. In another embodiment, the composition may further include one or more additional kidney cell populations. In one embodiment, the additional cell population is a second cell population not enriched for EPO-producing cells. In another embodiment, the additional cell population is a second cell population not enriched for EPO-producing cells, glomerular cells, or vascular cells. In another embodiment, the composition also includes a kidney cell population or admixture of kidney cells deposited in, deposited on, embedded in, coated with, suspended in, or entrapped in a biomaterial to form an implantable construct, as described herein, for the treatment of a disease or disorder described herein. In one embodiment, the cell populations are used alone or in combination with other cells or biomaterials, e.g., hydrogels, porous scaffolds, or native or synthetic peptides or proteins, to stimulate regeneration in acute or chronic disease states.

In another aspect, the effective treatment of a kidney disease in a subject by the methods disclosed herein can be observed through various indicators of erythropoiesis and/or kidney function. In one embodiment, the indicators of erythroid homeostasis include, without limitation, hematocrit (HCT), hemoglobin (HB), mean corpuscular hemoglobin (MCH), red blood cell count (RBC), reticulocyte number, reticulocyte %, mean corpuscular volume (MCV), and red blood cell distribution width (RDW). In one other embodiment, the indicators of kidney function include, without limitation, serum albumin, albumin to globulin ratio (A/G ratio), serum phosphorous, serum sodium, kidney size (measurable by ultrasound), serum calcium, phosphorous:calcium ratio, serum potassium, proteinuria, urine creatinine, serum creatinine, blood nitrogen urea (BUN), cholesterol levels, triglyceride levels and glomerular filtration rate (GFR). Furthermore, several indicators of general health and well-being include, without limitation, weight gain or loss, survival, blood pressure (mean systemic blood pressure, diastolic blood pressure, or systolic blood pressure), and physical endurance performance.

In another embodiment, an effective treatment with a bioactive renal cell formulation is evidenced by stabilization of one or more indicators of kidney function. The stabilization of kidney function is demonstrated by the observation of a change in an indicator in a subject treated by a method provided for herein as compared to the same indicator in a subject that has not been treated by the method herein. Alternatively, the stabilization of kidney function may be demonstrated by the observation of a change in an indicator in a subject treated by a method herein as compared to the same indicator in the same subject prior to treatment. The change in the first indicator may be an increase or a decrease in value. In one embodiment, the treatment provided by the present disclosure may include stabilization of blood urea nitrogen (BUN) levels in a subject where the BUN levels observed in the subject are lower as compared to a subject with a similar disease state who has not been treated by the methods of the present disclosure. In one other embodiment, the treatment may include stabilization of serum creatinine levels in a subject where the serum creatinine levels observed in the subject are lower as compared to a subject with a similar disease state who has not been treated by the methods of the present disclosure. In another embodiment, the treatment may include stabilization of hematocrit (HCT) levels in a subject where the HCT levels observed in the subject are higher as compared to a subject with a similar disease state who has not been treated by the methods of the present disclosure. In another embodiment, the treatment may include stabilization of red blood cell (RBC) levels in a subject where the RBC levels observed in the subject are higher as compared to a subject with a similar disease state who has not been treated by the methods of the present disclosure. Those of ordinary skill in the art will appreciate that one or more additional indicators described herein or known in the art may be measured to determine the effective treatment of a kidney disease in the subject.

In another aspect, the present disclosure concerns formulations for use in methods of providing erythroid homeostasis in a subject. In one embodiment, the method includes the step of (a) administering to the subject a formulation containing a renal cell population, e.g., B2 or B4', or admixture of renal cells, e.g., B2/B4' and/or B2/B3, or an enriched renal cell population, as described herein; and (b) determining, in a biological sample from the subject, that the level of an erythropoiesis indicator is different relative to the indicator level in a control, wherein the difference in indicator level (i) indicates the subject is responsive to the administering step (a), or (ii) is indicative of erythroid homeostasis in the subject. In another embodiment, the method includes the step of (a) administering to the subject a formulation comprising a renal cell population or admixture of renal cells as described herein; and (b) determining, in a biological sample from the subject, that the level of an erythropoiesis indicator is different relative to the indicator level in a control, wherein the difference in indicator level (i) indicates the subject is responsive to the administering step (s), or (ii) is indicative of erythroid homeostasis in the subject. In another embodiment, the method includes the step of (a) providing a biomaterial or biocompatible polymeric scaffold; (b) depositing a renal cell population or admixture of renal cells of the present disclosure on or within the biomaterial or scaffold in a manner described herein to form an implantable construct; (c) preparing a formulation containing the construct; (d) implanting the construct into the subject; and (e) determining, in a biological sample from the subject, that the level of an erythropoiesis indicator is different relative to the indicator level in a control, wherein the difference in indicator level (i) indicates the subject is responsive to the administering step (a), or (ii) is indicative of erythroid homeostasis in the subject.

In another aspect, the present disclosure concerns formulations for use in methods of providing both stabilization of kidney function and restoration of erythroid homeostasis to a subject in need, said subject having both a deficit in kidney function and an anemia and/or EPO-deficiency. In one embodiment, the method includes the step of administering a formulation containing a renal cell population or admixture of renal cells as described herein that contain at least one of the following cell types: tubular-derived cells, glomerulus-derived cells, interstitium-derived cells, collecting duct-derived cells, stromal tissue-derived cells, or cells derived from the vasculature. In another embodiment, the population or admixture contains both EPO-producing cells and tubular epithelial cells, the tubular cells having been identified by at least one of the following markers: megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8). In this embodiment, treatment of the subject would be demonstrated by an improvement in at least one indicator of kidney function concomitant with improvement in at least one indicator of erythropoiesis, compared to either an untreated subject or to the subject's pre-treatment indicators.

In one aspect, the present disclosure provides formulations for use in methods of (i) treating a kidney disease, anemia, or an EPO-deficiency; (ii) stabilizing kidney function, (iii) restoring erythroid homeostasis, or (iv) any combination of thereof by administering a renal cell population enriched for EPO-producing cells or admixture of renal cells containing a cell population enriched for EPO-producing cells as described herein, wherein the beneficial effects of the administration are greater than the effects of administering a cell population not enriched for EPO-producing cells. In another embodiment, the enriched cell population provides an improved level of serum blood urea nitrogen (BUN). In another embodiment, the enriched cell population provides an improved retention of protein in the serum. In another embodiment, the enriched cell population provides improved levels of serum cholesterol and/or triglycerides. In another embodiment, the enriched cell population provides an improved level of Vitamin D. In one embodiment, the enriched cell population provides an improved phosphorus:calcium ratio as compared to a non-enriched cell population. In another embodiment, the enriched cell population provides an improved level of hemoglobin as compared to a non-enriched cell population. In a further embodiment, the enriched cell population provides an improved level of serum creatinine as compared to a non-enriched cell population. In yet another embodiment, the enriched cell population provides an improved level of hematocrit as compared to a non-enriched cell population. In a further embodiment, the enriched cell population provides an improved level of red blood cell number (RBC #) as compared to a non-enriched cell population. In one embodiment, the improved level of hematocrit is restored to 95% normal healthy level. In a further embodiment, the enriched cell population provides an improved reticulocyte number as compared to a non-enriched cell population. In other embodiments, the enriched cell population provides an improved reticulocyte percentage as compared to a non-enriched cell population. In yet other embodiments, the enriched cell population provides an improved level of red blood cell volume distribution width (RDW) as compared to a non-enriched cell population. In yet another embodiment, the enriched cell population provides an improved level of hemoglobin as compared to a non-enriched cell population. In yet another embodiment, the enriched cell population provides an erythroietic response in the bone marrow, such that the marrow cellularity is near-normal and the myeloid:erythroid ratio is near normal.

In another aspect, the present disclosure provides formulations for use in methods of (i) treating a kidney disease, anemia, or an EPO-deficiency; (ii) stabilizing kidney function, (iii) restoring erythroid homeostasis, or (iv) any combination of thereof by administering an enriched cell population, wherein the beneficial effects of administering a renal cell population or admixture of renal cell populations described herein are characterized by improved erythroid homeostasis when compared to the beneficial effects provided by the administering of recombinant EPO (rEPO). In one embodiment, the population or admixture, when administered to a subject in need provides improved erythroid homeostasis (as determined by hematocrit, hemoglobin, or RBC #) when compared to the administration of recombinant EPO protein. In one embodiment, the population or admixture, when administered provides an improved level of hematocrit, RBC, or hemoglobin as compared to recombinant EPO, being no greater than about 10% lower or higher than hematocrit in a control. In a further embodiment, a single dose or delivery of the population or admixture, when administered provides improvement in erythroid homeostasis (as determined by increase in hematocrit, hemoglobin, or RBC #) in the treated subject for a period of time that significantly exceeds the period of time that a single dose or delivery of the recombinant EPO protein provides improvement in erythroid homeostasis. In another embodiment, the population or admixture, when administered at a dose described herein does not result in hematocrit, hemoglobin, or RBC # greater than about 110% of normal levels in matched healthy controls. In a further embodiment, the population or admixture, when administered at a dose described herein provides superior erythroid homeostasis (as determined by hematocrit, hemoglobin, or RBC #) compared to recombinant EPO protein delivered at a dose described herein. In another embodiment, the recombinant EPO is delivered at a dose of about 100 IU/kg, about 200 IU/kg, about 300 IU/kg, about 400 IU/kg, or about 500 IU/kg. Those of ordinary skill in the art will appreciate that other dosages of recombinant EPO known in the art may be suitable.

Another embodiment of the present disclosure is directed to the use of formulations containing at least one cell population, including enriched cell populations and admixtures thereof, described herein, or an implantable construct described herein, or secreted products as described herein, for the preparation of a medicament for the treatment of a kidney disease, anemia, or EPO deficiency in a subject in need, the providing of erythroid homeostasis in a subject in need, the improvement of kidney function in a subject in need, or providing a regenerative effect to a native kidney.

Another embodiment of the present disclosure is directed to formulations containing specific enriched cell population (s) (described herein) for the treatment of a kidney disease of a specific etiology, based on selection of specific cell subpopulation(s) based on specific verified therapeutic attributes.

In yet another aspect, the present disclosure provides formulations for use in methods of treating a kidney disease in a subject in need, comprising: administering to the subject a formulation comprising an admixture of mammalian renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiments, the method includes determining in a test sample from the subject that the level of a kidney function indicator is different relative to the indicator level in a control, wherein the difference in indicator level is indicative of a reduction in decline, stabilization, or an improvement of one or more kidney functions in the subject. In one embodiment, the B4' cell population used in the method is characterized by expression of a vascular marker. In certain embodiments, the B4' cell population used in the method is not characterized by expression of a glomerular marker. In one embodiment, the admixture of cells used in the method is capable of oxygen-tunable erythropoietin (EPO) expression. In certain embodiments, the kidney disease to be treated by the methods of the disclosure is accompanied by an erythropoietin (EPO) deficiency. In certain embodiments, the EPO deficiency is anemia. In some embodiments, the EPO deficiency or anemia occurs secondary to renal failure in the subject. In some other embodiments, the EPO deficiency or anemia occurs secondary to a disorder selected from the group consisting of chronic renal failure, primary EPO deficiency, chemotherapy or anti-viral therapy, non-myeloid cancer, HIV infection, liver disease, cardiac failure, rheumatoid arthritis, or multi-organ system failure. In certain embodiments, the composition used in the method further comprises a biomaterial comprising one or more biocompatible synthetic polymers and/or naturally-occurring proteins or peptides, wherein the admixture is coated with, deposited on or in, entrapped in, suspended in, embedded in and/or otherwise combined with the biomaterial. In certain embodiments, the admixture used in the formulations of the disclosure is derived from mammalian kidney tissue or cultured mammalian kidney cells. In other embodiments, the admixture is derived from a kidney sample that is autologous to the subject in need. In one embodiment, the sample is a kidney biopsy. In other embodiments, the formulation contains an admixture derived from a non-autologous kidney sample.

In yet another aspect, the disclosure provides a use of a formulation containing the cell preparations and admixtures described herein or an implantable construct of the instant disclosure for the preparation of a medicament useful in the treatment of a kidney disease, anemia or EPO deficiency in a subject in need thereof.

In another aspect, the present disclosure provides formulations for use in methods for the regeneration of a native kidney in a subject in need thereof. In one embodiment, the method includes the step of administering or implanting a cell population, admixture, or construct described herein to the subject. A regenerated native kidney may be characterized by a number of indicators including, without limitation, development of function or capacity in the native kidney, improvement of function or capacity in the native kidney, and the expression of certain markers in the native kidney. In one embodiment, the developed or improved function or capacity may be observed based on the various indicators of erythroid homeostasis and kidney function described above. In another embodiment, the regenerated kidney is characterized by differential expression of one or more stem cell markers. The stem cell marker may be one or more of the following: SRY (sex determining region Y)-box 2 (Sox2); Undifferentiated Embryonic Cell Transcription Factor (UTF1); Nodal Homolog from Mouse (NODAL); Prominin 1 (PROM1) or CD133 (CD133); CD24; and any combination thereof (see Ilagan et al. PCT/US2011/036347 incorporated herein by reference in its entirety). In another embodiment, the expression of the stem cell marker(s) is up-regulated compared to a control.

The cell populations described herein, including enriched cell populations and admixtures thereof, as well as constructs containing the same may be used to provide a regenerative effect to a native kidney. The effect may be provided by the cells themselves and/or by products secreted from the cells. The regenerative effect may be characterized by one or more of the following: a reduction in epithelial-mesenchymal transition (which may be via attenuation of TGF-β signaling); a reduction in renal fibrosis; a reduction in renal inflammation; differential expression of a stem cell marker in the native kidney; migration of implanted cells and/or native cells to a site of renal injury, e.g., tubular injury, engraftment of implanted cells at a site of renal injury, e.g., tubular injury; stabilization of one or more indicators of kidney function (as described herein); restoration of erythroid homeostasis (as described herein); and any combination thereof.

7. Methods of Monitoring Regeneration

In another aspect, the present disclosure provides a prognostic method for monitoring regeneration of a native kidney following administration or implantation of a formulation containing a cell population, admixture, or construct described herein to the subject. In one embodiment, the method includes the step of detecting the level of marker expression in a test sample obtained from the subject and in a control sample, wherein a higher level of expression of the marker in the test sample, as compared to the control sample, is prognostic for regeneration of the native kidney in the subject. In another embodiment, the method includes the detection of expression of one or more stem cell markers in the sample. The stem cell marker may be selected from Sox2; UTF1; NODAL; CD133; CD24; and any combination thereof (see Example 11 of Ilagan et al. PCT/US2011/036347). The detecting step may include determining that expression of the stem cell marker(s) is up-regulated or higher in the test sample relative to a control sample, wherein the higher level of expression is prognostic for regeneration of the subject's native kidney. In one other embodiment, mRNA expression of the stem cell marker(s) is detected. In other embodiments, the detection of mRNA expression may be via a PCR-based method, e.g., qRT-PCR.

In situ hybridization may also be used for the detection of mRNA expression. In another embodiment, polypeptide expression of the stem cell marker may also be detected using an anti-stem cell marker agent. In one other embodiment, the agent is an antibody against the marker. In another embodiment, stem cell marker polypeptide expression is detected using immunohistochemistry or a Western Blot. Those of ordinary skill in the art will appreciate other methods for detecting mRNA and/or polypeptide expression of markers.

In another aspect, the disclosure provides methods for prognostic evaluation of a patient following implantation or administration of a formulation containing a cell population, admixture, or construct described herein. In one embodiment, the method includes the step of detecting the level of marker expression in a test sample obtained from said subject; (b) determining the expression level in the test sample relative to the level of marker expression relative to a control sample (or a control reference value); and (c) predicting regenerative prognosis of the patient based on the determination of marker expression levels, wherein a higher level of expression of marker in the test sample, as compared to the control sample (or a control reference value), is prognostic for regeneration in the subject.

In one other aspect, the present disclosure provides prognostic methods for monitoring regeneration of a native kidney following administration or implantation of a formulation containing a cell population, admixture, or construct described herein to the subject, in which a non-invasive method is used. As an alternative to a tissue biopsy, a regenerative outcome in the subject receiving treatment can be assessed from examination of a bodily fluid, e.g., urine. It has been discovered that microvesicles obtained from subject-derived urine sources contain certain components including, without limitation, specific proteins and miRNAs that are ultimately derived from the renal cell populations impacted by treatment with the cell populations of the present disclosure. These components may include factors involved in stem cell replication and differentiation, apoptosis, inflammation and immuno-modulation. A temporal analysis of microvesicle-associated miRNA/protein expression patterns allows for continuous monitoring of regenerative outcomes within the kidney of subjects receiving the cell populations, admixtures, or constructs of the present disclosure.

These kidney-derived vesicles and/or the luminal contents of kidney derived vesicles shed into the urine of a subject may be analyzed for biomarkers indicative of regenerative outcome.

In one embodiment, the present disclosure provides methods of assessing whether a kidney disease (KD) patient is responsive to treatment with a therapeutic formulation. The method may include the step of determining or detecting the amount of vesicles or their luminal contents in a test sample obtained from a KD patient treated with the therapeutic, as compared to or relative to the amount of vesicles in a control sample, wherein a higher or lower amount of vesicles or their luminal contents in the test sample as compared to the amount of vesicles or their luminal contents in the control sample is indicative of the treated patient's responsiveness to treatment with the therapeutic.

The present disclosure also provides a method of monitoring the efficacy of treatment with a therapeutic in a KD patient. In one embodiment, the method includes the step of determining or detecting the amount of vesicles in a test sample obtained from a KD patient treated with the therapeutic, as compared to or relative to the amount of vesicles or their luminal contents in a control sample, wherein a higher or lower amount of vesicles or their luminal contents in the test sample as compared to the amount of vesicles or their luminal contents in the control sample is indicative of the efficacy of treatment with the therapeutic in the KD patient.

The present disclosure provides a method of identifying a patient subpopulation for which an agent is effective to treat kidney disease (KD). In one embodiment, the method includes the step of determining a correlation between efficacy of the agent and the presence of an amount of vesicles or their luminal contents in samples from the patient subpopulation as compared to the amount of vesicles or their luminal contents in a sample obtained from a control sample, wherein a higher or lower amount of vesicles in the samples from the patient subpopulation as compared to the amount of vesicles or their luminal contents in the control sample is indicative that the agent is effective to treat KD in the patient subpopulation.

The determining or detecting step may include analyzing the amount of miRNA or other secreted products that may exist in the test sample, e.g., urine.

The non-invasive prognostic methods may include the step of obtaining a urine sample from the subject before and/or after administration or implantation of a cell population, admixture, or construct described herein. Vesicles and other secreted products may be isolated from the urine samples using standard techniques including without limitation, centrifugation to remove unwanted debris (Zhou et al. 2008. Kidney Int. 74(5):613-621; Skog et al. U.S. Published Patent Application No. 20110053157, each of which is incorporated herein by reference in its entirety).

The present disclosure relates to non-invasive methods to detect regenerative outcome in a subject following treatment. The methods involve detection of vesicles or their luminal contents in urine from a treated subject. The luminal contents may be one or more miRNAs. The detection of combinations or panels of the individual miRNAs may be suitable for such prognostic methods. Exemplary combinations include two or more of the following: miR-24; miR-195; miR-871; miR-30b-5p; miR-19b; miR-99a; miR-429; let-7f miR-200a; miR-324-5p; miR-10a-5p; and any combination thereof. In one embodiment, the combination of miRNAs may include 2, 3, 4, 5, 6, 7, 8, 9, 10, 11, or more individual miRNAs. Those of ordinary skill in the art will appreciate that other miRNAs and combinations of miRNAs may be suitable for use in such prognostic methods. Sources of additional miRNAs include miRBase at http://mirbase.org, which is hosted and maintained in the Faculty of Life Sciences at the University of Manchester.

Those of skill in the art will appreciate that the prognostic methods for detecting regeneration may be suitable for subjects treated with other therapeutics known in the art, apart from the cell populations and constructs described herein.

In some embodiments, the determining step comprises the use of a software program executed by a suitable processor for the purpose of (i) measuring the differential level of marker expression (or vesicles/vesicle contents) in a test sample and a control; and/or (ii) analyzing the data obtained from measuring differential level of marker expression in a test sample and a control. Suitable software and processors are well known in the art and are commercially available. The program may be embodied in software stored on a tangible medium such as CD-ROM, a floppy disk, a hard drive, a DVD, or a memory associated with the processor, but persons of ordinary skill in the art will readily appreciate that the entire program or parts thereof could alternatively be executed by a device other than a processor, and/or embodied in firmware and/or dedicated hardware in a well known manner.

Following the determining step, the measurement results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. In some embodiments, the assays will be performed or the assay results analyzed in a country or jurisdiction which differs from the country or jurisdiction to which the results or diagnoses are communicated.

In a preferred embodiment, a prognosis, prediction and/or treatment recommendation based on the level of marker expression measured in a test subject having a differential level of marker expression is communicated to the subject as soon as possible after the assay is completed and the prognosis and/or prediction is generated. The results and/or related information may be communicated to the subject by the subject's treating physician. Alternatively, the results may be communicated directly to a test subject by any means of communication, including writing, electronic forms of communication, such as email, or telephone. Communication may be facilitated by use of a computer, such as in case of email communications. In certain embodiments, the communication containing results of a prognostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, prognosis and/or prediction of regeneration, and communicating of assay results or prognoses, may be carried out in diverse (e.g., foreign) jurisdictions.

In another aspect, the prognostic methods described herein provide information to an interested party concerning the regenerative success of the implantation or administration.

In all embodiments, the methods of providing a regenerated kidney to a subject in need of such treatment as described herein may include the post-implantation step of prognostic evaluation of regeneration as described above.

8. Bioactive Cell Formulations

The formulations described herein incorporate biomaterials having properties which create a favorable environment for the active agent, such as bioactive renal cells, to be administered to a subject. In one embodiment, the formulation contains a first biomaterial that provides a favorable environment from the time the active agent is formulated with the biomaterial up until the point of administration to the subject. In one other embodiment, the favorable environment concerns the advantages of having bioactive cells suspended in a substantially solid state versus cells in a fluid (as described herein) prior to administration to a subject. In another embodiment, the first biomaterial is a temperature-sensitive biomaterial. The temperature-sensitive biomaterial may have (i) a substantially solid state at about 8° C. or below, and (ii) a substantially liquid state at ambient temperature or above. In one embodiment, the ambient temperature is about room temperature.

In another aspect, the formulation contains bioactive cells combined with a second biomaterial that provides a favorable environment for the combined cells from the time of formulation up until a point after administration to the subject. In one embodiment, the favorable environment provided by the second biomaterial concerns the advantages of administering cells in a biomaterial that retains structural integrity up until the point of administration to a subject and for a period of time after administration. In one embodiment, the structural integrity of the second biomaterial following implantation is minutes, hours, days, or weeks. In one embodiment, the structural integrity is less than one month, less than one week, less than one day, or less than one hour. The relatively short term structural integrity provides a formulation that can deliver the active agent and biomaterial to a target location in a tissue or organ with controlled handling, placement or dispersion without being a hindrance or barrier to the interaction of the incorporated elements with the tissue or organ into which it was placed.

In another embodiment, the second biomaterial is a temperature-sensitive biomaterial that has a different sensitivity than the first biomaterial. The second biomaterial may have (i) a substantially solid state at about ambient temperature or below, and (ii) a substantially liquid state at about 37° C. or above. In one embodiment, the ambient temperature is about room temperature.

In one embodiment, the second biomaterial is crosslinked beads. The crosslinked beads may have finely tunable in vivo residence times depending on the degree of crosslinking, as described herein. In another embodiment, the crosslinked beads comprise bioactive cells and are resistant to enzymatic degradation as described herein.

The formulations of the present disclosure may include the first biomaterial combined with an active agent, e.g., bioactive cells, with or without a second biomaterial combined with an active agent, e.g., bioactive cells. Where a formulation includes a second biomaterial, it may be a temperature sensitive bead and/or a crosslinked bead. Various representative formulations are provided in the examples below (see also FIGS. 3-7).

The bioactive cell preparations, admixtures, and/or constructs described herein can be administered as bioactive cell formulations. In one aspect, the formulations include the cells and one or more biomaterials that provide stability to the bioactive cell preparations, admixtures, and/or constructs described herein. In one embodiment, the biomaterial is a temperature-sensitive biomaterial that can maintain at least two different phases or states depending on temperature. The biomaterial is capable of maintaining a first state at a first temperature, a second state at a second temperature, and/or a third state at a third temperature. The first, second or third state may be a substantially solid, a substantially liquid, or a substantially semi-solid or semi-liquid state. In one embodiment, the biomaterial has a first state at a first temperature and a second state at a second temperature, wherein the first temperature is lower than the second temperature.

In one other embodiment, the state of the temperature-sensitive biomaterial is a substantially solid state at a temperature of about 8° C. or below. In other embodiments, the substantially solid state is maintained at about 1° C., about 2° C., about 3° C., about 4° C., about 5° C., about 6° C., about 7° C., or about 8° C. In one embodiment, the substantially solid state has the form of a gel. In other embodiments, the state of the temperature-sensitive biomaterial is a substantially liquid state at ambient temperature or above. In one embodiment, the substantially liquid state is maintained at about 31° C., about 32° C., about 33° C., about 34° C., about 35° C., about 36° C., or about 37° C. In one embodiment, the ambient temperature is about room temperature.

In another embodiment, the state of the temperature-sensitive biomaterial is a substantially solid state at a temperature of about ambient temperature or below. In one embodiment, the ambient temperature is about room temperature. In another embodiment, the substantially solid state is maintained at about 17° C., about 16° C., about 15° C., about 14° C., about 13° C., about 12° C., about 11° C., about 10° C., about 9° C., about 8° C., about 7° C., about 6° C., about 5° C., about 4° C., about 3° C., about 2° C., or about 1° C. In one embodiment, the substantially solid state has the form of a bead. In another embodiment, the state of the temperature-sensitive biomaterial is a substantially liquid state at a temperature of about 37° C. or above. In one other embodiment, the substantially solid state is maintained at about 37° C., about 38° C., about 39° C., or about 40° C.

The temperature-sensitive biomaterials may be provided in the form of a solution, in the form of beads, or in other suitable forms described herein and/or known to those of ordinary skill in the art. The cell populations and preparations described herein may be coated with, deposited on, embedded in, attached to, seeded, suspended in, or entrapped in a temperature-sensitive biomaterial. Alternatively, the temperature-sensitive biomaterial may be provided without any cells, such as, for example in the form of spacer beads.

In other embodiments, the temperature-sensitive biomaterial has a transitional state between a first state and a second state. In one embodiment, the transitional state is a solid-to-liquid transitional state between a temperature of about 8° C. and about ambient temperature. In one embodiment, the ambient temperature is about room temperature. In one other embodiment, the solid-to-liquid transitional state occurs at one or more temperatures of about 8° C., about 9° C., about 10° C., about 11° C., about 12° C., about 13° C., about 14° C., about 15° C., about 16° C., about 17° C., and about 18° C.

The temperature-sensitive biomaterials have a certain viscosity at a given temperature measured in centipoise (cP). In one embodiment, the biomaterial has a viscosity at 25° C. of about 1 cP to about 5 cP, about 1.1 cP to about 4.5 cP, about 1.2 cP to about 4 cP, about 1.3 cP to about 3.5 cP, about 1.4 cP to about 3.5 cP, about 1.5 cP to about 3 cP, about 1.55 cP to about 2.5 cP, or about 1.6 cP to about 2 cP. In another embodiment, the 0.75% (w/v) solution has a viscosity at 37° C. of about 1.0 cP to about 1.15 cP. The viscosity at 37° C. may be about 1.0 cP, about 1.01 cP, about 1.02 cP, about 1.03 cP, about 1.04 cP, about 1.05 cP, about 1.06 cP, about 1.07 cP, about 1.08 cP, about 1.09 cP, about 1.10 cP, about 1.11 cP, about 1.12 cP, about 1.13 cP, about 1.14 cP, or about 1.15 cP. In one other embodiment, the biomaterial is a gelatin solution. The gelatin is present at about 0.5%, about 0.55%, about 0.6%, about 0.65%, about 0.7%, about 0.75%, about 0.8%, about 0.85%, about 0.9%, about 0.95% or about 1%, (w/v) in the solution. In one example, the biomaterial is a 0.75% (w/v) gelatin solution in PBS. In one embodiment, the 0.75% (w/v) solution has a viscosity at 25° C. of about 1.6 cP to about 2 cP. In one embodiment, the 0.75% (w/v) solution has a viscosity at 37° C. of about 1.07 cP to about 1.08 cP. The gelatin solution may be provided in PBS, DMEM, or another suitable solvent.

In one aspect, the bioactive cell formulation also includes a cell viability agent. In one embodiment, the cell viability agent is selected from the group consisting of an antioxidant, an oxygen carrier, an immunomodulatory factor, a cell recruitment factor, a cell attachment factor, an anti-inflammatory agent, an angiogenic factor, a wound healing factor, and products secreted from bioactive cells.

Antioxidants are characterized by the ability to inhibit oxidation of other molecules. Antioxidants include, without limitation, one or more of 6-hydroxy-2,5,7,8-tetramethyl-chroman-2-carboxylic acid (Trolox®), carotenoids, flavonoids, isoflavones, ubiquinone, glutathione, lipoic acid, superoxide dismutase, ascorbic acid, vitamin E, vitamin A, mixed carotenoids (e.g., beta carotene, alpha carotene, gamma carotene, lutein, lycopene, phytopene, phytofluene, and astaxanthin), selenium, Coenzyme Q10, indole-3-carbinol, proanthocyanidins, resveratrol, quercetin, catechins, salicylic acid, curcumin, bilirubin, oxalic acid, phytic acid, lipoic acid, vanilic acid, polyphenols, ferulic acid, theaflavins, and derivatives thereof. Those of ordinary skill in the art will appreciate other suitable antioxidants for use in the present disclosure.

Oxygen carriers are agents characterized by the ability to carry and release oxygen. They include, without limitation, perfluorocarbons and pharmaceuticals containing perfluorocarbons. Suitable perfluorocarbon-based oxygen carriers include, without limitation, perfluorooctyl bromide (C8F17Br); perfluorodichorotane (C8F16Cl2); perfluorodecyl bromide; perfluobron; perfluorodecalin; perfluorotripopylamine; perfluoromethylcyclopiperidine; Fluosol® (perfluorodecalin & perfluorotripopylamine); Perftoran® (perfluorodecalin & perfluoromethylcyclopiperidine); Oxygent® (perfluorodecyl bromide & perfluobron); Ocycyte™ (perfluoro (tert-butylcyclohexane)). Those of ordinary skill in the art will appreciate other suitable perfluorocarbon-based oxygen carriers for use in the present disclosure.

Immunomodulatory factors include, without limitation, osteopontin, FAS Ligand factors, interleukins, transforming growth factor beta, platelet derived growth factor, clusterin, transferrin, regulated upon action, normal T-cell expressed, secreted protein (RANTES), plasminogen activator inhibitor-1 (Pai-1), tumor necrosis factor alpha (TNF-alpha), interleukin 6 (IL-6), alpha-1 microglobulin, and beta-2-microglobulin. Those of ordinary skill in the art will appreciate other suitable immunomodulatory factors for use in the present disclosure.

Anti-inflammatory agents or immunosuppressant agents (described below) may also be part of the formulation. Those of ordinary skill in the art will appreciate other suitable antioxidants for use in the present formulations and/or treatments.

Cell recruitment factors include, without limitation, monocyte chemotatic protein 1 (MCP-1), and CXCL-1. Those of ordinary skill in the art will appreciate other suitable cell recruitment factors for use in the present formulations and/or treatments.

Cell attachment factors include, without limitation, fibronectin, procollagen, collagen, ICAM-1, connective tissue growth factor, laminins, proteoglycans, specific cell adhesion peptides such as RGD and YSIGR. Those of ordinary skill in the art will appreciate other suitable cell attachment factors for use in the present formulations and/or treatments.

Angiogenic factors include, without limitation, matrix metalloprotease 1 (MMP1), matrix metalloprotease 2 (MMP2), vascular endothelial growth factor F (VEGF), matrix metalloprotease 9 (MMP-9), tissue inhibitor or matalloproteases-1 (TIMP-1) vascular endothelial growth factor F (VEGF), angiopoietin-2 (ANG-2). Those of ordinary skill in the art will appreciate other suitable angiogenic factors for use in the present formulations and/or treatments.

Wound healing factors include, without limitation, keratinocyte growth factor 1 (KGF-1), tissue plasminogen activator (tPA), calbindin, clusterin, cystatin C, trefoil factor 3. Those of ordinary skill in the art will appreciate other suitable wound healing factors for use in the present formulations and/or treatments.

Secreted products from bioactive cells described herein may also be added to the bioactive cell formulation as a cell viability agent.

In one other aspect, the formulation includes a temperature-sensitive biomaterial described herein and a population of biocompatible beads containing a biomaterial. In one embodiment, the beads are crosslinked. Crosslinking may be achieved using any suitable crosslinking agent known to those of ordinary skill in the art, such as, for example, carbodiimides; aldehydes (e.g. furfural, acrolein, formaldehyde, glutaraldehyde, glyceryl aldehyde), succinimide-based crosslinkers {Bis(sulfosuccinimidyl) suberate (BS3), Disuccinimidyl glutarate (DSG), Disuccinimidyl suberate (DSS), Dithiobis(succinimidyl propionate), Ethylene glycolbis(sulfosuccinimidylsuccinate), Ethylene glycolbis(succinimidylsuccinate) (EGS), Bis(Sulfosuccinimidyl) glutarate (BS2G), Disuccinimidyl tartrate (DST)}; epoxides (Ethylene glycol diglycidyl ether, 1,4 Butanediol diglycidyl ether); saccharides (glucose and aldose sugars); sulfonic acids and p-toluene sulfonic acid; carbonyldiimidazole; genipin; imines; ketones; diphenylphosphorylazide (DDPA); terephthaloyl chloride; cerium (III) nitrate hexahydrate; microbial transglutaminase; and hydrogen peroxide. Those of ordinary skill in the art will appreciate other suitable crosslinking agents and crosslinking methods for use in the present methods, formulations and/or treatments.

In one embodiment, the beads are carbodiimide-crosslinked beads. The carbodiimide-crosslinked beads may be crosslinked with a carbodiimide selected from the group consisting of 1-Ethyl-3-[3-dimethylaminopropyl] carbodiimide hydrochloride (EDC), DCC-N,N'-dicyclohexylcarbodiimide (DCC), and N,N'-Diisopropylcarbodiimide (DIPC). Beads treated with lower concentration of EDC were expected to have a higher number of free primary amines, while samples treated with high concentrations of crosslinker would have most of the primary amines engaged in amide bonds. The intensity of the orange color developed by the covalent bonding between the primary amine and picrylsulfonic acid, detectable spectrophotometrically at 335 nm, is proportional to the number of primary amines present in the sample. When normalized per milligram of protein present in the sample, an inverse correlation between the number of free amines present and the initial concentration of EDC used for crosslinking can be observed. This result is indicative of differential bead crosslinking, dictated by the amount of carbodiimide used in the reaction. In general, crosslinked beads exhibit a reduced number of free primary amines as compared to non-crosslinked beads. The number of free primary amines may be detected spectrophotometrically at about 335 nm.

The crosslinked beads have a reduced susceptibility to enzymatic degradation as compared to non-crosslinked biocompatible beads, thereby providing beads with finely tunable in vivo residence times. For example, the cross-linked beads are resistant to endogenous enzymes, such as collagenases. The provision of crosslinked beads is part of a delivery system focused on the development and production of biomaterials that facilitate one or more of: (a) delivery of attached cells to the desired sites and creation of space for regeneration and ingrowth of native tissue and vascular supply; (b) ability to persist at the site long enough to allow cells to establish, function, remodel their microenvironment and secrete their own extracellular matrix (ECM); (c) promotion of integration of the transplanted cells with the surrounding tissue; (d) ability to implant cells in a substantially solid form; (e) short term structural integrity that does not provide a significant barrier to tissue ingrowth or integration of delivered cells/materials with the host tissue; (f) localized in vivo delivery in a substantially solid form thereby preventing dispersion of cells within the tissue during implantation; (g) improved stability and viability of anchorage dependent cells compared to cells suspended in a fluid; and (h) biphasic release profile when cells are delivered i) in a substantially solid form (e.g., attached to beads), and ii) in a substantially liquid form (e.g., suspended in a fluid).

In one embodiment, the present disclosure provides crosslinked beads containing gelatin. Non-crosslinked gelatin beads are not suitable for a bioactive cell formulation because they rapidly lose integrity and cells dissipate from the injection site. In contrast, highly crosslinked gelatin beads may persist too long at the injection site and may hinder the de-novo ECM secretion, cell integration and tissue regeneration. The present disclosure allows for the in vivo residence time of the crosslinked beads to be finely tuned. In order to tailor the biodegradability of biomaterials, different crosslinker concentrations of carbodiimide are used while the overall reaction conditions were kept constant for all samples. For example, the enzymatic susceptibility of carbodiimide-crosslinked beads can be finely tuned by varying the concentration of crosslinking agent from about zero to about 1M. In some embodiments, the concentration is about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 55 mM, about 60 mM, about 65 mM, about 70 mM, about 75 mM, about 80 mM, about 85 mM, about 90 mM, about 95 mM, or about 100 mM. The crosslinker concentration may also be about 0.15 M, about 0.2 M, about 0.25 M, about 0.3 M, about 0.35 M, about 0.4 M, about 0.45 M, about 0.5 M, about 0.55 M, about 0.6 M, about 0.65 M, about 0.7 M, about 0.75 M, about 0.8 M, about 0.85 M, about 0.9 M, about 0.95 M, or about 1 M. In another embodiment, the crosslinking agent is 1-Ethyl-3-[3-dimethylaminopropyl] carbodiimide hydrochloride (EDC). In one embodiment, the EDC-crosslinked beads are gelatin beads.

Cross-linked beads may have certain characteristics that favor the seeding, attachment, or encapsulation. For example, the beads may have a porous surface and/or may be substantially hollow. The presence of pores provides an increased cell attachment surface allowing for a greater number of cells to attach as compared to a non-porous or smooth surface. In addition, the pore structure can support host tissue integration with the porous beads supporting the formation of de novo tissue. The beads have a size distribution that can be fitted to a Weibull plot corresponding to the general particle distribution pattern. In one embodiment, the cross-linked beads have an average diameter of less than about 120 μm, about 115 μm, about 110 μm, about 109 μm, about 108 μm, about 107 μm, about 106 μm, about 105 nm, about 104 μm, about 103 μm, about 102 μm, about 101 μm, about 100 μm, about 99 μm, about 98 μm, about 97 μm, about 96 μm, about 95 μm, about 94 μm, about 93 μm, about 92 μm, about 91 μm, or about 90 μm. The characteristics of the cross-linked beads vary depending upon the casting process. For instance, a process in which a stream of air is used to aerosolize a liquid gelatin solution and spray it into liquid nitrogen with a thin layer chromatography reagent sprayer (ACE Glassware) is used to provide beads having the afore-mentioned characteristics. Those of skill in the art will appreciate that modulating the parameters of the casting process provides the opportunity to tailor different characteristics of the beads, e.g., different size distributions.

The cytocompatibility of the cross-linked beads is assessed in vitro prior to formulation using cell culture techniques in which beads are cultured with cells that correspond to the final bioactive cell formulation. For instance, the beads are cultured with primary renal cells prior to preparation of a bioactive renal cell formulation and live/dead cell assays are used to confirm cytocompatibility. In certain formulations, the biocompatible cross-linked beads are combined with a temperature-sensitive biomaterial in solution at about 5% (w/w) to about 15% (w/w) of the volume of the solution. The cross-linked beads may be present at about 5% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), about 10% (w/w), about 10.5% (w/w), about 11% (w/w), about 11.5% (w/w), about 12% (w/w), about 12.5% (w/w), about 13% (w/w), about 13.5% (w/w), about 14% (w/w), about 14.5% (w/w), or about 15% (w/w) of the volume of the solution.

In another aspect, the present disclosure provides formulations that contain biomaterials which degrade over a period time on the order of minutes, hours, or days. This is in contrast to a large body or work focusing on the implantation of solid materials that then slowly degrade over days, weeks, or months.

In another aspect, the present disclosure provides formulations having biocompatible cross-linked beads seeded with bioactive cells together with a delivery matrix. In one embodiment, the delivery matrix has one or more of the following characteristics: biocompatibility, biodegradeable/bioresorbable, a substantially solid state prior to and during implantation into a subject, loss of structural integrity (substantially solid state) after implantation, and cytocompatible environment to support cellular viability. The delivery matrix's ability to keep implanted particles (e.g., crosslinked beads) spaced out during implantation enhances native tissue ingrowth. If the delivery matrix is absent, then compaction of cellularized beads during implantation can lead to inadequate room for sufficient tissue ingrowth. The delivery matrix facilitates implantation of solid formulations. In addition, the short duration of the structural integrity means that soon after implantation, the matrix does not provide a significant barrier to tissue ingrowth or integration of the delivered cells/materials with host tissue. The delivery matrix provides for localization of the formulation described herein since inserted of a solid unit helps prevent the delivered materials from dispersing within the tissue during implantation. For cell-based formulations, a solid delivery matrix improves stability and viability of anchorage dependent cells compared to cells suspended in a fluid.

In one embodiment, the delivery matrix is a population of biocompatible beads that is not seeded with cells. In another embodiment, the unseeded beads are dispersed throughout and in between the individual cell-seeded beads. The unseeded beads act as "spacer beads" between the cell-seeded beads prior to and immediately after transplantation. The spacer beads contain a temperature-sensitive biomaterial having a substantially solid state at a first temperature and a substantially liquid state at a second temperature, wherein the first temperature is lower than the second temperature. For example, the spacer beads contain a biomaterial having a substantially solid state at about ambient temperature or below and a substantially liquid state at about 37° C., such as that described herein. In one embodiment, the ambient temperature is about room temperature. In another embodiment, the biomaterial is a gelatin solution. The gelatin solution is present at about 4%, about 4.5%, about 5%, about 5.5%, about 6%, about 6.5%, about 7%, about 7.5%, about 8%, about 8.5%, about 9%, about 9.5%, about 10%, about 10.5%, or about 11%, (w/v). The gelatin solution may be provided in PBS, cell culture media (e.g., DMEM), or another suitable solvent.

In one aspect, the present disclosure provides formulations that contain biomaterials which are implanted in a substantially solid form (e.g., spacer beads) and then liquefy/melt or otherwise lose structural integrity following implantation into the body. This is in contrast to the significant body of work focusing on the use of materials that can be injected as a liquid, which then solidify in the body.

The temperature-sensitivity of spacer beads can be assessed in vitro prior to formulation. Spacer beads can be labeled and mixed with unlabeled non-temperature-sensitive beads. The mixture is then incubated at 37° C. to observe changes in physical transition. The loss of shape of the labeled temperature-sensitive beads at the higher temperature is observed over time. For example, temperature-sensitive gelatin beads may be made with Alcian blue dye to serve as a marker of physical transition. The blue gelatin beads are mixed with Cultispher S beads (white), loaded into a catheter, then extruded and incubated in 1×PBS, pH 7.4, at 37° C. The loss of shape of the blue gelatin beads is followed microscopically at different time points. Changes in the physical state of the blue gelatin beads are visible after 30 min becoming more pronounced with prolonged incubation times. The beads do not completely dissipate because of the viscosity of the material.

The bioactive cell formulations described herein may be used to prepare renal cell-based formulations for injection into the kidney. However, those of ordinary skill in the art will appreciate that the formulations will be suitable for many other types of bioactive cell populations. For example, the present disclosure contemplates formulations for bioactive cells for injection into any solid organ or tissue.

In one aspect, the bioactive cell formulations described herein will contain a set number of cells. In one embodiment, the total number of cells for the formulation is about $10^4$, about $10^5$, about $10^6$, about $10^7$, about $10^8$, or about $10^9$. In one embodiment, the dosage of cells for a formulation described herein may be calculated based on the estimated mass or functional mass of the target organ or tissue. In certain embodiments, the bioactive cell formulations contain a dosage corresponding to a number of cells based upon the weight of the host organ that will be the subject of treatment by the formulation. For example, a bioactive renal cell formulation is based upon an average weight of about 150 grams for a human kidney. In one embodiment, the number of cells per gram (g) of kidney is about 600 cells/g to about $7.0\times10^7$ cells/g. In some embodiments, the number of cells per gram of kidney is about 600 cells/g, about 1000 cells/g, about 1500 cells/g, about 2000 cells/g, about 2500 cells/g, about 3000 cells/g, about 3500 cells/g, about 4000 cells/g, about 4500 cells/g, about 5000 cells/g, about 5500 cells/g, about 6000 cells/g, about 6500 cells/g, about 7000 cells/g, about 7500 cells/g, about 8000 cells/g, about 8500 cells/g, about 9000 cells/g, about 9500 cells/g, or about 10,000 cells/g.

In other embodiments, the number of cells per gram of kidney is about $1.5\times10^4$ cells/g, about $2.0\times10^4$ cells/g, about $2.5\times10^4$ cells/g, about $3.0\times10^4$ cells/g, about $3.5\times10^4$ cells/g, about $4.0\times10^4$ cells/g, about $4.5\times10^4$ cells/g, about $5.0\times10^4$ cells/g, about $5.5\times10^4$ cells/g, about $6.0\times10^4$ cells/g, about $6.5\times10^4$ cells/g, about $7.0\times10^4$ cells/g, about $7.5\times10^4$ cells/g, about $8.0\times10^4$ cells/g, about $9.5\times10^4$ cells/g.

In other embodiments, the number of cells per gram of kidney is about $1.0\times10^5$ cells/g, about $1.5\times10^5$ cells/g, about $2.0\times10^5$ cells/g, about $2.5\times10^5$ cells/g, about $3.0\times10^5$ cells/g, about $3.5\times10^5$ cells/g, about $4.0\times10^5$ cells/g, about $4.5\times10^5$ cells/g, about $5.0\times10^5$ cells/g, about $5.5\times10^5$ cells/g, about $6.0\times10^5$ cells/g, about $6.5\times10^5$ cells/g, about $7.0\times10^5$ cells/g, about $7.5\times10^5$ cells/g, about $8.0\times10^5$ cells/g, about $8.5\times10^5$ cells/g, about $9.0\times10^5$ cells/g, or about $9.5\times10^5$ cells/g.

In other embodiments, the number of cells per gram of kidney is about $1.0\times10^6$ cells/g, about $1.5\times10^6$ cells/g, about $2.0\times10^6$ cells/g, about $2.5\times10^6$ cells/g, about $3.0\times10^6$ cells/g, about $3.5\times10^6$ cells/g, about $4.0\times10^6$ cells/g, about $4.5\times10^6$ cells/g, about $5.0\times10^6$ cells/g, about $5.5\times10^6$ cells/g, about $6.0\times10^6$ cells/g, about $6.5\times10^6$ cells/g, about $7.0\times10^6$ cells/g, about $7.5\times10^6$ cells/g, about $8.0\times10^6$ cells/g, about $8.5\times10^6$ cells/g, about $9.0\times10^6$ cells/g, about $9.5\times10^6$ cells/g, $1.0\times10^7$ cells/g, or about $1.5\times10^7$ cells/g.

A total number of cells may be selected for the formulation and the volume of the formulation may be adjusted to reach the proper dosage.

In some embodiments, the formulation may contain a dosage of cells to a subject that is a single dosage or a single dosage plus additional dosages. In other embodiments, the dosages may be provided by way of a construct as described herein. The therapeutically effective amount of the renal cell populations or admixtures of renal cell populations described herein can range from the maximum number of cells that is safely received by the subject to the minimum number of cells necessary for treatment of kidney disease, e.g., stabilization, reduced rate-of-decline, or improvement of one or more kidney functions.

The therapeutically effective amount of the renal cell populations or admixtures thereof described herein can be suspended in a pharmaceutically acceptable carrier or excipient. Such a carrier includes, but is not limited to basal culture medium plus 1% serum albumin, saline, buffered saline, dextrose, water, collagen, alginate, hyaluronic acid, fibrin glue, polyethyleneglycol, polyvinylalcohol, carboxymethylcellulose and combinations thereof. The formulation should suit the mode of administration.

Accordingly, the disclosure provides a use of a formulation containing renal cell populations or admixtures thereof, for example, the B2 cell population alone or admixed with the B3 and/or B4 or B4' cell population, for the manufacture of a medicament to treat kidney disease in a subject. In some embodiments, the medicament further comprises recombinant polypeptides, such as growth factors, chemokines or cytokines. In further embodiments, the medicaments comprise a human kidney-derived cell population. The cells used to manufacture the medicaments can be isolated, derived, or enriched using any of the variations provided for the methods described herein.

The renal cell preparation(s), or admixtures thereof, or compositions are formulated in accordance with routine procedures as a pharmaceutical composition adapted for administration to human beings. Typically, compositions for intravenous administration, intra-arterial administration or administration within the kidney capsule, for example, are solutions in sterile isotonic aqueous buffer. Where necessary, the composition can also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. When the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Pharmaceutically acceptable carriers are determined in part by the particular composition being administered, as well as by the particular method used to administer the composition. Accordingly, there are a wide variety of suitable formulations of pharmaceutical compositions (see, e.g., Alfonso R Gennaro (ed), Remington: The Science and Practice of Pharmacy, formerly Remington's Pharmaceutical Sciences 20th ed., Lippincott, Williams & Wilkins, 2003, incorporated herein by reference in its entirety). The pharmaceutical compositions are generally formulated as sterile, substantially isotonic and in full compliance with all Good Manufacturing Practice (GMP) regulations of the U.S. Food and Drug Administration.

One aspect further provides a pharmaceutical formulation, comprising a renal cell preparation, for example, the B2 cell preparation alone or incombination with the B3 and/or B4 or B4' cell preparation, and a pharmaceutically acceptable carrier. In some embodiments, the formulation comprises from $10^4$ to $10^9$ mammalian kidney-derived cells.

Modified Release Formulations

In one aspect, the formulations of the present disclosure are provided as modified release formulations. In general, the modified release is characterized by an initial release of a first active agent upon administration following by at least one additional, subsequent release of a second active agent. The first and second active agents may be the same or they may be different. In one embodiment, the formulations provide modified release through multiple components in the same formulation. In another embodiment, the modified release formulation contains an active agent as part of a first component that allows the active agent to move freely throughout the volume of the formulation, thereby permitting immediate release at the target site upon administration. The first component may be a temperature-sensitive biomaterial having a substantially liquid phase and a substantially solid phase, wherein the first component is in a substantially liquid phase at the time of administration. In one embodiment, the active agent in the substantially liquid phase such that it is substantially free to move throughout the volume of the formulation, and therefore is immediately released to the target site upon administration.

In another embodiment, the modified release formulation has an active agent as part of a second component in which the active agent is attached to, deposited on, coated with, embedded in, seeded upon, or entrapped in the second component, which persists before and after administration to the target site. The second component contains structural elements with which the active agent is able to associate with, thereby preventing immediate release of the active agent from the second component at the time of administration. For example, the second component is provided in a substantially solid form, e.g., biocompatible beads, which may be crosslinked to prevent or delay in vivo enzymatic degradation. In one embodiment, the active agent in the substantially solid phase retains its structural integrity within the formulation before and after administration and therefore it does not immediately release the active agent to the target site upon administration. Suitable carriers for modified release formulations have been described herein but those of ordinary skill in the art will appreciate other carriers that are appropriate for use herein.

In one embodiment, the formulation provides an initial rapid delivery/release of delivered elements, including cells, nanoparticles, therapeutic molecules, etc. followed by a later delayed release of elements. The formulations of the present disclosure can be designed for such biphasic release profile where the agent to be delivered is provided in both an unattached form (e.g., cells in a solution) and an attached form (e.g., cells together with beads or another suitable carrier). Upon initial administration, the unencumbered agent is provided immediately to the site of delivery while release of the encumbered agent is delayed until structural integrity of the carrier (e.g., beads) fails at which point the previously attached agent is released. As discussed below, other suitable mechanisms of release will be appreciated by those of ordinary skill in the art.

The time delay for release can be adjusted based upon the nature of the active agent. For example, the time delay for release in a bioactive cell formulation may be on the order of seconds, minutes, hours, or days. In some circumstances, a delay on the order of weeks may be appropriate. For other active agents, such as small or large molecules, the time delay for release in a formulation may be on the order of seconds, minutes, hours, days, weeks, or months. It is also possible for the formulation to contain different biomaterials that provide different time delay release profiles. For example, a first biomaterial with a first active agent may have a first release time and a second biomaterial with a second active agent may have a second release time. The first and second active agent may be the same or different.

As discussed herein, the time period of delayed release may generally correspond to the time period for loss of structural integrity of a biomaterial. However, those of ordinary skill in the art will appreciate other mechanisms of delayed release. For example, an active agent may be continually released over time independent of the degradation time of any particular biomaterial, e.g., diffusion of a drug from a polymeric matrix. In addition, bioactive cells can migrate away from a formulation containing a biomaterial and the bioactive cells to native tissue. In one embodiment, bioactive cells migrate off of a biomaterial, e.g., a bead, to the native tissue.

Biodegradable, biocompatible polymers can be used, such as ethylene vinyl acetate, polyanhydrides, polyglycolic acid, collagen, polyorthoesters, and polylactic acid. Prolonged absorption of injectable formulations can be brought about by including in the formulation an agent that delays absorption, for example, monostearate salts and gelatin. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Additional methods applicable to the controlled or extended release of polypeptide agents are described, for example, in U.S. Pat. Nos. 6,306,406 and 6,346,274, as well as, for example, in U.S. Patent Application Nos. US20020182254 and US20020051808, all of which are incorporated herein by reference.

9. Methods and Routes of Administration

The bioactive cell formulations of the present disclosure can be administered alone or in combination with other bioactive components. The formulations are suitable for injection or implantation of incorporated tissue engineering elements to the interior of solid organs to regenerate tissue. In addition, the formulations are used for the injection or implantation of tissue engineering elements to the wall of hollow organs to regenerate tissue.

In one aspect, the present disclosure provides methods of providing a bioactive cell formulation described herein to a subject in need. In one embodiment, the source of the bioactive cell may be autologous or allogeneic, syngeneic (autogeneic or isogeneic), and any combination thereof. In instances where the source is not autologous, the methods may include the administration of an immunosuppressant agent. Suitable immunosuppressant drugs include, without limitation, azathioprine, cyclophosphamide, mizoribine, ciclosporin, tacrolimus hydrate, chlorambucil, lobenzarit disodium, auranofin, alprostadil, gusperimus hydrochloride, biosynsorb, muromonab, alefacept, pentostatin, daclizumab, sirolimus, mycophenolate mofetil, leflonomide, basiliximab, dornase a, bindarid, cladribine, pimecrolimus, ilodecakin, cedelizumab, efalizumab, everolimus, anisperimus, gavilimomab, faralimomab, clofarabine, rapamycin, siplizumab, saireito, LDP-03, CD4, SR-43551, SK&F-106615, IDEC-114, IDEC-131, FTY-720, TSK-204, LF-080299, A-86281, A-802715, GVH-313, HMR-1279, ZD-7349, IPL-423323, CBP-1011, MT-1345, CNI-1493, CBP-2011, J-695, LJP-920, L-732531, ABX-RB2, AP-1903, IDPS, BMS-205820, BMS-224818, CTLA4-1 g, ER-49890, ER-38925, ISAtx-247, RDP-58, PNU-156804, LJP-1082, TMC-95A, TV-4710, PTR-262-MG, and AGI-1096 (see U.S. Pat. No. 7,563,822). Those of ordinary skill in the art will appreciate other suitable immunosuppressant drugs.

The treatment methods of the subject disclosure involve the delivery of a bioactive cell formulation described herein. In one embodiment, direct administration of cells to the site of intended benefit is preferred. A subject in need may also be treated by in vivo contacting of a native kidney with a bioactive cell formulation described herein together with products secreted from one or more enriched renal cell populations, and/or an admixture or construct containing the same.

The step of contacting a native kidney in vivo with secreted products may be accomplished through the use/administration of a formulation containing a population of secreted products from cell culture media, e.g., conditioned media, or by implantation of an enriched cell population, and admixture, or a construct capable of secreting the products in vivo. The step of in vivo contacting provides a regenerative effect to the native kidney.

A variety of means for administering cells and/or secreted products to subjects will, in view of this specification, be apparent to those of skill in the art. Such methods include injection of the cells into a target site in a subject.

Cells and/or secreted products can be inserted into a delivery device or vehicle, which facilitates introduction by injection or implantation into the subjects. In certain embodiments, the delivery vehicle can include natural materials. In certain other embodiments, the delivery vehicle can include synthetic materials. In one embodiment, the delivery vehicle provides a structure to mimic or appropriately fit into the organ's architecture. In other embodiments, the delivery vehicle is fluid-like in nature. Such delivery devices can include tubes, e.g., catheters, for injecting cells and fluids into the body of a recipient subject. In a preferred embodiment, the tubes additionally have a needle, e.g., a syringe, through which the cells can be introduced into the subject at a desired location. In some embodiments, mammalian kidney-derived cell populations are formulated for administration into a blood vessel via a catheter (where the term "catheter" is intended to include any of the various tube-like systems for delivery of substances to a blood vessel). Alternatively, the cells can be inserted into or onto a biomaterial or scaffold, including but not limited to textiles, such as weaves, knits, braids, meshes, and non-wovens, perforated films, sponges and foams, and beads, such as solid or porous beads, microparticles, nanoparticles, and the like (e.g., Cultispher-S gelatin beads—Sigma). The cells can be prepared for delivery in a variety of different forms. For example, the cells can be suspended in a solution or gel. Cells can be mixed with a pharmaceutically acceptable carrier or diluent in which the cells remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. One of skill in the art will appreciate that the delivery vehicle used in the delivery of the cell populations and admixtures thereof can include combinations of the above-mentioned characteristics.

Modes of administration of the formulations containing isolated renal cell population(s), for example, the B2 cell population alone or admixed with B4' and/or B3, include, but are not limited to, systemic, intra-renal (e.g., parenchymal), intravenous or intra-arterial injection and injection directly into the tissue at the intended site of activity. Additional modes of administration to be used include single or multiple injection(s) via direct laparotomy, via direct laparoscopy, transabdominal, or percutaneous. Still yet additional modes of administration to be used include, for example, retrograde and ureteropelvic infusion. Surgical means of administration include one-step procedures such as, but not limited to, partial nephrectomy and construct implantation, partial nephrectomy, partial pyelectomy, vascularization with omentum±peritoneum, multifocal biopsy needle tracks, cone or pyramidal, to cylinder, and renal pole-like replacement, as well as two-step procedures including, for example, organoid-internal bioreactor for replanting. In one embodiment, the formulations containing admixtures of cells are delivered via the same route at the same time. In another embodiment, each of the cell compositions comprising the controlled admixture are delivered separately to specific locations or via specific methodologies, either simultaneously or in a temporally-controlled manner, by one or more of the methods described herein.

The appropriate cell implantation dosage in humans can be determined from existing information relating to either the activity of the cells, for example EPO production, or extrapolated from dosing studies conducted in preclinical studies. From in vitro culture and in vivo animal experiments, the amount of cells can be quantified and used in calculating an appropriate dosage of implanted material. Additionally, the patient can be monitored to determine if additional implantation can be made or implanted material reduced accordingly.

One or more other components can be added to the cell populations and admixtures thereof, including selected extracellular matrix components, such as one or more types of collagen or hyaluronic acid known in the art, and/or growth factors, platelet-rich plasma and drugs.

Those of ordinary skill in the art will appreciate the various formulations and methods of administration suitable for the secreted products described herein.

10. Articles of Manufacture and Kits

The instant disclosure further includes kits comprising the polymeric matrices and scaffolds as disclosed herein and related materials, and/or cell culture media and instructions for use. The instructions for use may contain, for example, instructions for culture of the cells or administration of the cells and/or cell products. In one embodiment, the present disclosure provides a kit comprising a scaffold as described herein and instructions. In yet another embodiment, the kit includes an agent for detection of marker expression, reagents for use of the agent, and instructions for use. This kit may be used for the purpose of determining the regenerative prognosis of a native kidney in a subject following the implantation or administration of a cell population, an admixture, or a construct described herein. The kit may also be used to determine the biotherapeutic efficacy of a cell population, admixture, or construct described herein.

Another embodiment is an article of manufacture containing bioactive cells useful for treatment of subjects in need. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating a condition and may have a sterile access port (for example the container may be a solution bag or a vial having a stopper pierceable by an injection needle). At least one active agent in the formulation is a bioactive cell population as provided for herein. The label or package insert indicates that the formulation is used for treating the particular condition. The label or package insert will further comprise instructions for administering the formulation to the patient. Articles of manufacture and kits comprising combinatorial therapies described herein are also contemplated. Package insert refers to instructions customarily included in commercial packages of therapeutic products that contain information about the indications, usage, dosage, administration, contraindications and/or warnings concerning the use of such therapeutic products. In one embodiment, the package insert indicates that the formulation is used for treating a disease or disorder, such as, for example, a kidney disease or disorder. It may further include other materials desirable from a commercial and user standpoint, including other buffers, diluents, filters, needles, and syringes. Kits are also provided that are useful for various purposes, e.g., for assessment of regenerative outcome. Kits can be provided which contain detection agents for urine-derived vesicles and/or their contents, e.g., nucleic acids (such as miRNA), vesicles, exosomes, etc., as described herein. Detection agents include, without limitation, nucleic acid primers and probes, as well as antibodies for in vitro detection of the desired target. As with the article of manufacture, the kit comprises a container and a label or package insert on or associated with the container. The container holds a composition comprising at least one detection agent. Additional containers may be included that contain, e.g., diluents and buffers or control detection agents. The label or package insert may provide a description of the composition as well as instructions for the intended in vitro, prognostic, or diagnostic use.

11. Reports

The methods of this disclosure, when practiced for commercial purposes generally produce a report or summary of the regenerative prognosis. The methods of this disclosure will produce a report comprising a prediction of the probable course or outcome of regeneration before and after any administration or implantation of a formulation containing a cell population, an admixture, or a construct described herein. The report may include information on any indicator pertinent to the prognosis. The methods and reports of this disclosure can further include storing the report in a database. Alternatively, the method can further create a record in a database for the subject and populate the record with data. In one embodiment the report is a paper report, in another embodiment the report is an auditory report, in another embodiment the report is an electronic record. It is contemplated that the report is provided to a physician and/or the patient. The receiving of the report can further include establishing a network connection to a server computer that includes the data and report and requesting the data and report from the server computer. The methods provided for herein may also be automated in whole or in part.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a formulation "comprising" a number of components, another embodiment would encompass a formulation "consisting essentially of" the same components, and a third embodiment would encompass a formulation "consisting of" the same components. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patents, patent applications, and literature references cited in the present specification are hereby incorporated by reference in their entirety.

EXAMPLES

Example 1

Preparation of Solutions

This example provides the compositions of the various media formulations and solutions used in the following Examples for the isolation and characterization of the heterogeneous renal cell population, and manufacture of the regenerative therapy product.

TABLE 1.1

Culture Media and Solutions

| Material | Composition |
|---|---|
| Tissue Transport Medium | Viaspan ™ or HypoThermosol-FRS ® or DMEM<br>Kanamycin: 100 µg/mL |
| Renal Cell Growth Medium | DMEM:KSFM (50:50)<br>5% FBS<br>Growth Supplements:<br>HGF: 10 mg/L<br>EGF: 2.5 µg/L<br>Insulin: 10.0 mg/L,<br>Transferrin: 5.5 mg/L<br>Selenium: 670 µg/L<br>Kanamycin: 100 µg/mL |
| Tissue Wash Solution | DMEM<br>Kanamycin: 100 µg/mL |
| Digestion Solution | Collagenase IV: 300 Units<br>Dispase: 5 mg/mL<br>Calcium Chloride: 5 mM |
| Cell Dissociation Solution | TrypLE |
| Density Gradient Solution | 7% OptiPrep<br>OptiMEM |
| Cryopreservation Solution | DMEM or HypoThermosol ® FRS<br>10% DMSO<br>10% FBS |

Dulbecco's Phosphate Buffered Saline (DPBS) was used for all cell washes.

Example 2

Isolation of the Heterogeneous Unfractionated Renal Cell Population

This example illustrates the isolation of an unfractionated (UNFX) heterogeneous renal cell population from human. Initial tissue dissociation was performed to generate heterogeneous cell suspensions from human kidney tissue.

Renal tissue via kidney biopsy provided the source material for a heterogeneous renal cell population. Renal tissue comprising one or more of cortical, corticomedullary junction or medullary tissue may be used. It is preferred that the corticomedullary junction tissue is used. Multiple biopsy cores (minimum 2), avoiding scar tissue, were required from a CKD kidney. Renal tissue was obtained by the clinical investigator from the patient at the clinical site approximately 4 weeks in advance of planned implantation of the final NKA. The tissue was transported in the Tissue Transport Medium of Example 1.

The tissue was then washed with Tissue Wash Solution of Example 1 in order to reduce incoming bioburden before processing the tissue for cell extractions.

Renal tissue was minced, weighed, and dissociated in the Digestion Solution of Example 1. The resulting cell suspension was neutralized in Dulbecco's Modified Eagle Medium (D-MEM)+10% fetal bovine serum (FBS) (Invitrogen, Carlsbad CA), washed, and resuspended in serum-free, supplement-free, Keratinocyte Media (KSFM) (Invitrogen). Cell suspensions were then subjected to a 15% (w/v) iodixanol (OptiPrep™, Sigma) gradient to remove red blood cells and debris prior to initiation of culture onto tissue culture treated polystyrene flasks or dishes at a density of 25,000 cells per $cm^2$ in Renal Cell Growth Medium of Example 1. For example, cells may be plated onto T500 Nunc flask at $25 \times 10^6$ cells/flask in 150 ml of 50:50 media.

Example 3

Cell Expansion of the Isolated Renal Cell Population

Renal cell expansion is dependent on the amount of tissue received and on the success of isolating renal cells from the incoming tissue. Isolated cells can be cryopreserved, if required (see infra). Renal cell growth kinetics may vary from sample to sample due to the inherent variability of cells isolated from individual patients.

A defined cell expansion process was developed that accommodates the range of cell recoveries resulting from the variability of incoming tissue Table 3.1. Expansion of renal cells involves serial passages in closed culture vessels (e.g., T-flasks, Cell Factories, HyperStacks®) in Renal Cell Growth Medium Table 1.1 using defined cell culture procedures.

A BPE-free medium was developed for human clinical trials to eliminate the inherent risks associated with the use of BPE. Cell growth, phenotype (CK18) and cell function (GGT and LAP enzymatic activity) were evaluated in BPE-free medium and compared to BPE containing medium used in the animal studies. Renal cell growth, phenotype and function were equivalent in the two media. (data no shown)

TABLE 3.1

Cell Recovery from Human Kidney Biopsies

| Source | Renal cells (cells/10 mg tissue) | |
|---|---|---|
| | Passage 0 | Passage 1 |
| Human Kidney Tissue Samples (n = 6) | 1.51-5.36 × 106 | 2.40-7.48 × 107 |

Figure 2A:
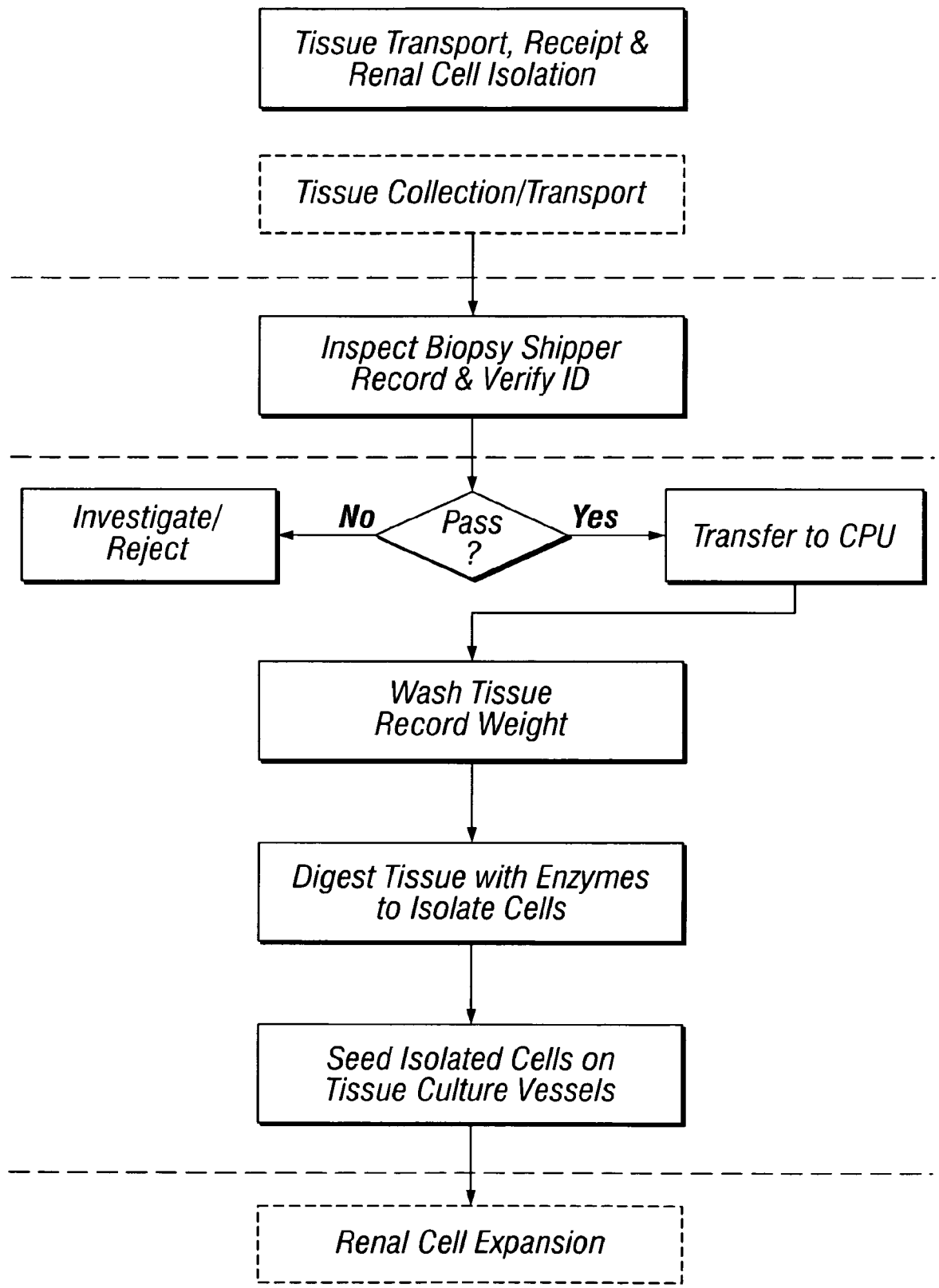
FIG. 2A-D is a flow diagram providing further details of the process depicted in FIG. 1 and described herein.
Figure 2B:
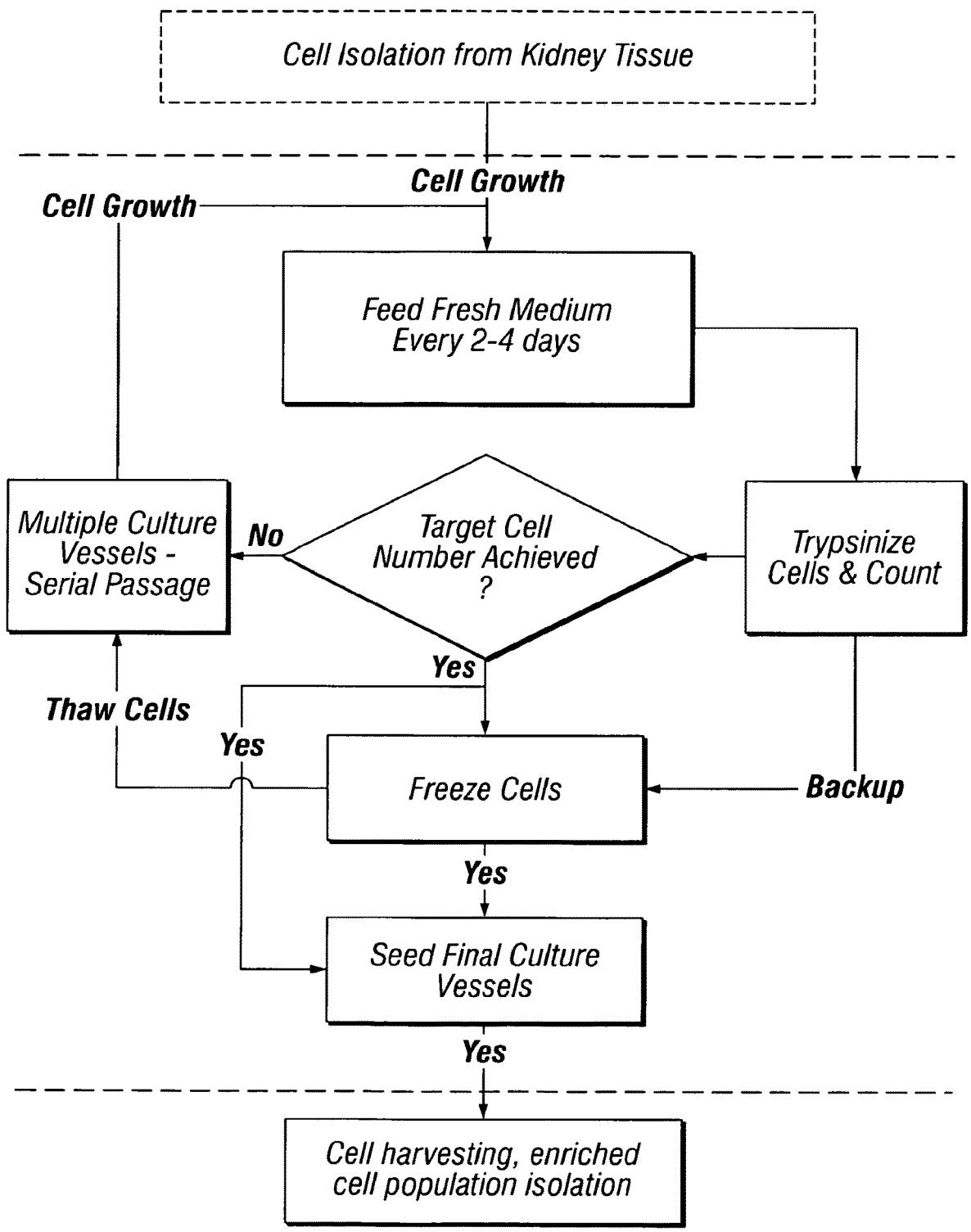

Once cell growth was observed in the initial T-flasks (passage 0) and there were no visual signs of contamination, culture medium was replaced and changed thereafter every 2-4 days FIG. 2B. Cells were assessed to verify renal cell morphology by visual observation of cultures under the microscope. Cultures characteristically demonstrated a tight pavement or cobblestone appearance, due to the cells clustering together. These morphological characteristics vary during expansion and may not be present at every passage. Cell culture confluence was estimated using an Image Library of cells at various levels of confluence in the culture vessels employed throughout cell expansions.

Renal cells were passaged by trypsinization when culture vessels are at least 50% confluent FIG. 2B. Detached cells were collected into vessels containing Renal Cell Growth Medium, counted and cell viability calculated. At each cell passage, cells were seeded at 500-4000 cells/cm2 in a sufficient number of culture vessels in order to expand the cell number to that required for formulation of NKA FIG. 2B. Culture vessels were placed in a 37° C. incubator in a 5% CO2 environment. As described above, cell morphology and confluence was monitored and tissue culture media was replaced every 2-4 days. Table 3.2 lists the viability of human renal cells observed during cell isolation and expansion of six kidney biopsies from human donors.

TABLE 3.2

Cell Viability of Human Renal Cells in Culture

| Passage (n = 6) | Cell Viability (Average %) | Range (%) |
|---|---|---|
| P0 | 88 | 84-93 |
| P1 | 91 | 80-98 |
| P2 | 94 | 92-99 |
| P3 | 98 | 97-99 |

Inherent variability of tissue from different patients resulted in different cell yield in culture. Therefore, it is not practical to strictly define the timing of cell passages or number and type of culture vessels required at each passage to attain target cell numbers. Typically renal cells undergo 2 or 3 passages; however, duration of culture and cell yield can vary depending on the cell growth rate. This is exemplified in FIG. 3 where the culture duration and cell yields (calculation) from 6 patients are shown.

Cells were detached for harvest or passage with 0.25% Trypsin with EDTA (Invitrogen). Viability was assessed via Trypan Blue exclusion and enumeration was performed manually using a hemacytometer or using the automated Cellometer® counting system (Nexcelom Bioscience, Lawrence MA).

Example 4

Cryopreservation of Cultured Cells

Expanded renal cells were routinely cryopreserved to accommodate for inherent variability of cell growth from individual patients and to deliver product on a pre-determined clinical schedule (FIG. 2B). Cryopreserved cells also provide a backup source of cells in the event that another NKA is needed (e.g., delay due to patient sickness, unforeseen process events, etc.). Conditions were established that have been used to cryopreserve cells and recover viable, functional cells upon thawing.

For cryopreservation, cells were suspended to a final concentration of about $50 \times 10^6$ cells/mL in Cryopreservation Solution (see Example 1) and dispensed into vials. One mL vials containing about $50 \times 10^6$ cells/mL were placed in the freezing chamber of a controlled rate freezer and frozen at a pre-programmed rate. After freezing, the cells were transferred to a liquid nitrogen freezer for in-process storage.

Example 5

Preparation of SRC Cell Population

Selected Renal Cells (SRC) can be prepared from the final culture vessels that are grown from cryopreserved cells or directly from expansion cultures depending on scheduling FIG. 2B.

If using cryopreserved cells, the cells were thawed and plated on tissue culture vessels for one final expansion step. When the final culture vessels were approximately 50-100% confluent cells were ready for processing for SRC separation. Media exchanges and final washes of NKA dilute any residual Cryopreservation Solution in the final product.

Once the final cell culture vessels have reached at least 50% confluence the culture vessels were transferred to a hypoxic incubator set for 2% oxygen in a 5% CO2 environment at 37° C. and cultured overnight. See FIG. 2C. Cells may be held in the oxygen-controlled incubator set to 2% oxygen for as long as 48 hours. Exposure to the more physiologically relevant low-oxygen (2%) environment improved cell separation efficiency and enabled greater detection of hypoxia-induced markers such as VEGF.

After the cells have been exposed to the hypoxic conditions for a sufficient time (e.g., overnight to 48 hours), the cells were detached with 0.25% Trypsin with EDTA (Invitrogen). Viability was assessed via Trypan Blue exclusion and enumeration was performed manually using a hemacytometer or using the automated Cellometer® counting system (Nexcelom Bioscience, Lawrence MA). Cells were washed once with DPBS and resuspended to about $850 \times 10^6$ cells/mL in DPBS.

Density gradient centrifugation was used to separate harvested renal cell populations based on cell buoyant density. Renal cell suspensions were separated on single-step 7% iodixanol Density Gradient Solution (OptiPrep; 60% (w/v) in OptiMEM; see Example 1).

The 7% OptiPrep gradient solution was prepared and refractive index indicative of desired density was measured (R.I. 1.3456+/− 0.0004) prior to use. Harvested renal cells were layered on top of the gradient solution. The density gradient was centrifuged at 800 g for 20 min at room temperature (without brake) in either centrifuge tubes or a cell processor (e.g., COBE 2991). The cellular fraction exhibiting buoyant density greater than approximately 1.045 g/mL was collected after centrifugation as a distinct pellet FIG. 4. Cells maintaining a buoyant density of less than 1.045 g/mL were excluded and discarded.

Figure 2C:
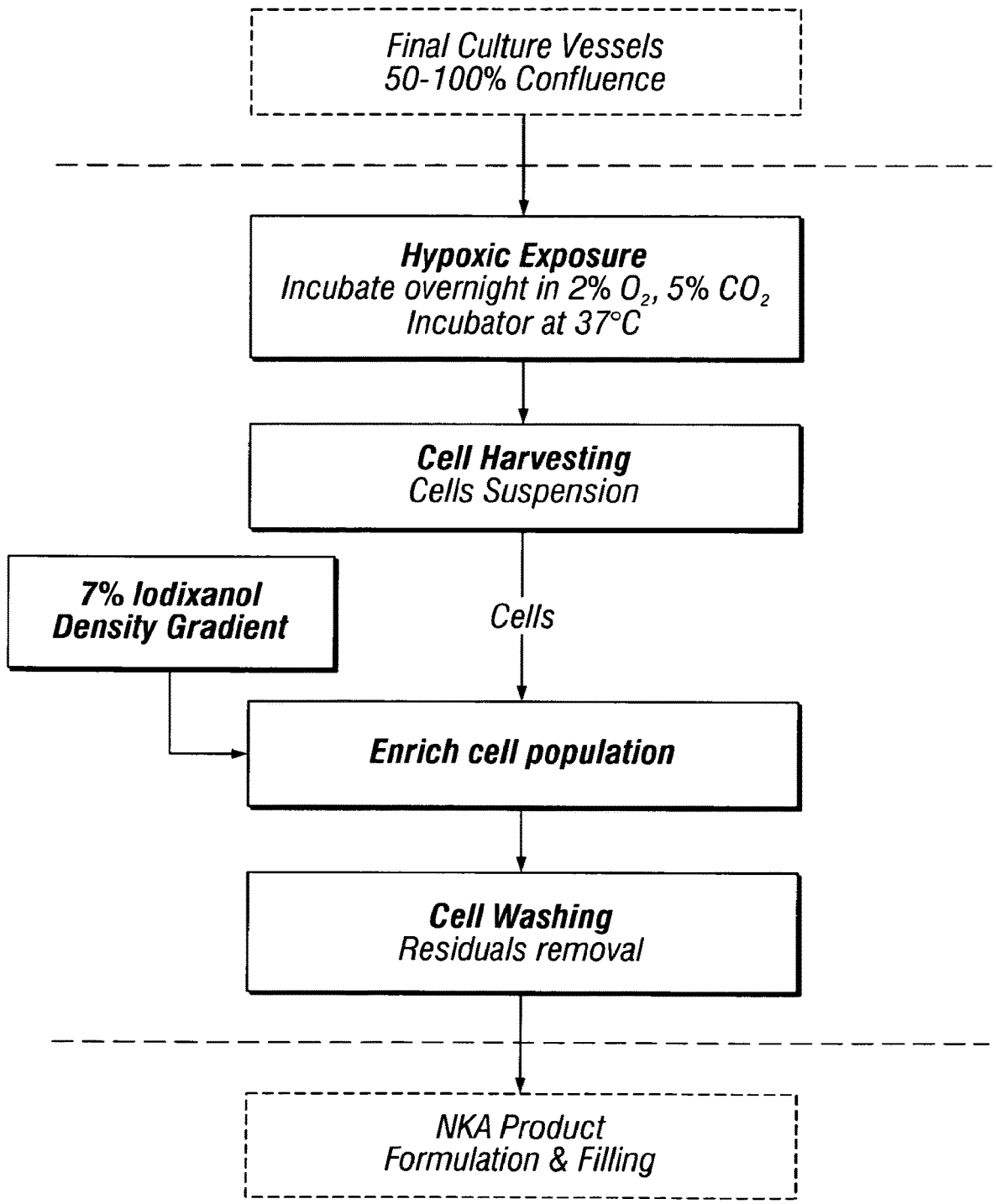

The SRC pellet was re-suspended in DPBS (FIG. 2C). The carry-over of residual OptiPrep, FBS, culture medium and ancillary materials in the final product is minimized by 4 DPBS wash and 1 Gelatin Solution steps.

Example 6

Cells with Therapeutic Potential can be Isolated and Propagated from Normal and Chronically-Diseased Kidney Tissue The objective of the present study was to determine the functional characterization of human NKA cells through high content analysis (HCA). High-content imaging (HCI) provides simultaneous imaging of multiple sub-cellular events using two or more fluorescent probes (multiplexing) across a number of samples. High-content Analysis (HCA) provides simultaneous quantitative measurement of multiple cellular parameters captured in High-Content Images. In brief, unfractionated (UNFX) cultures were generated (Aboushwareb et al., *World J Urol* 26, 295, 2008) and maintained independently from core biopsies taken from five human kidneys with advanced chronic kidney disease (CKD) and three non-CKD human kidneys using standard biopsy procedures. After (2) passages of UNFX ex vivo, cells were harvested and subjected to density gradient methods (as described in Example 2 of Basu et al., WO 2012/064369) to generate subfractions, including subfractions B2, B3, and/or B4.

Figure 4:
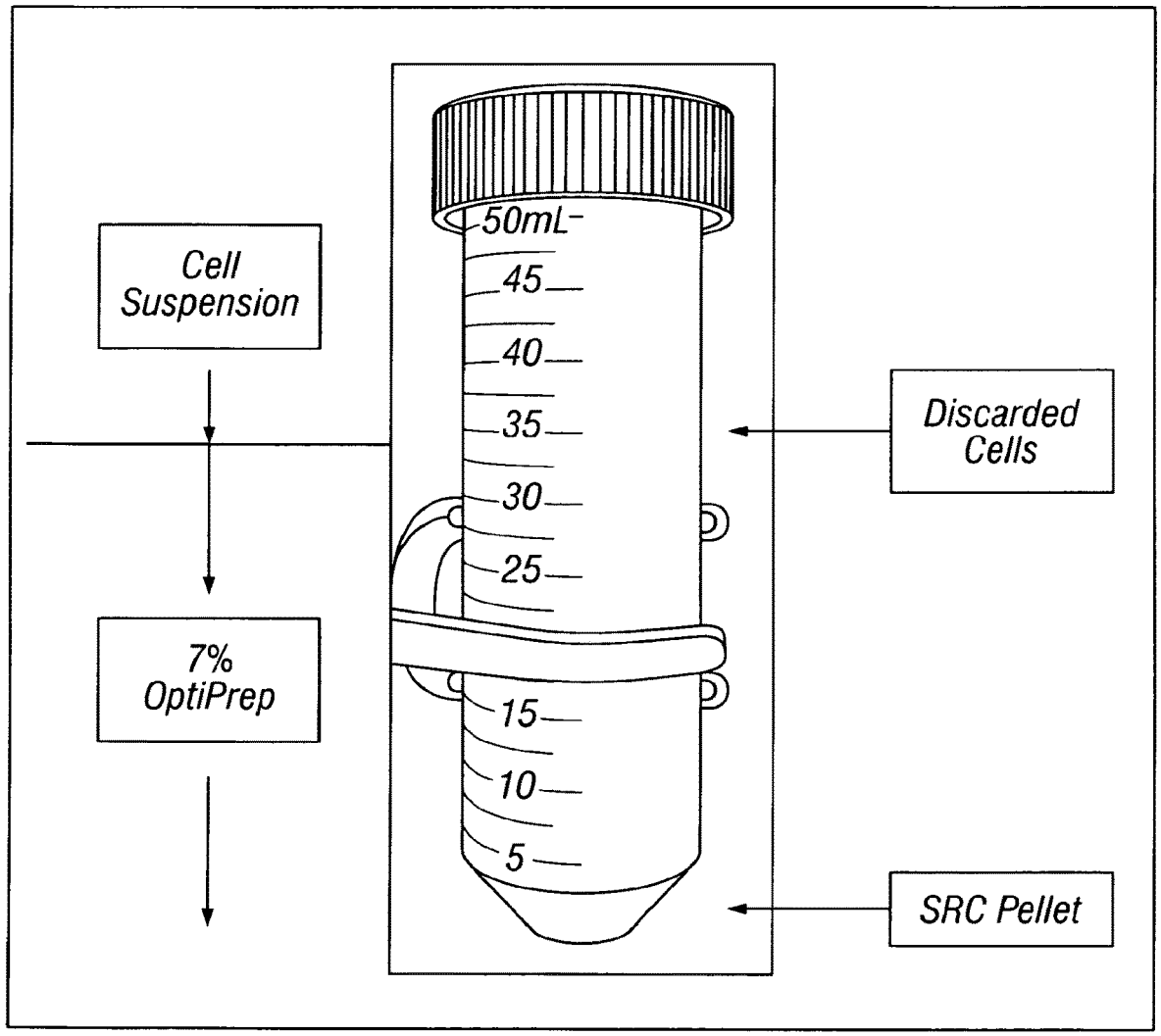
FIG. 4 is a picture of the SRC banding in a 7% OptiPrep® density gradient. Reference is made to Example 5.
Figure 5:
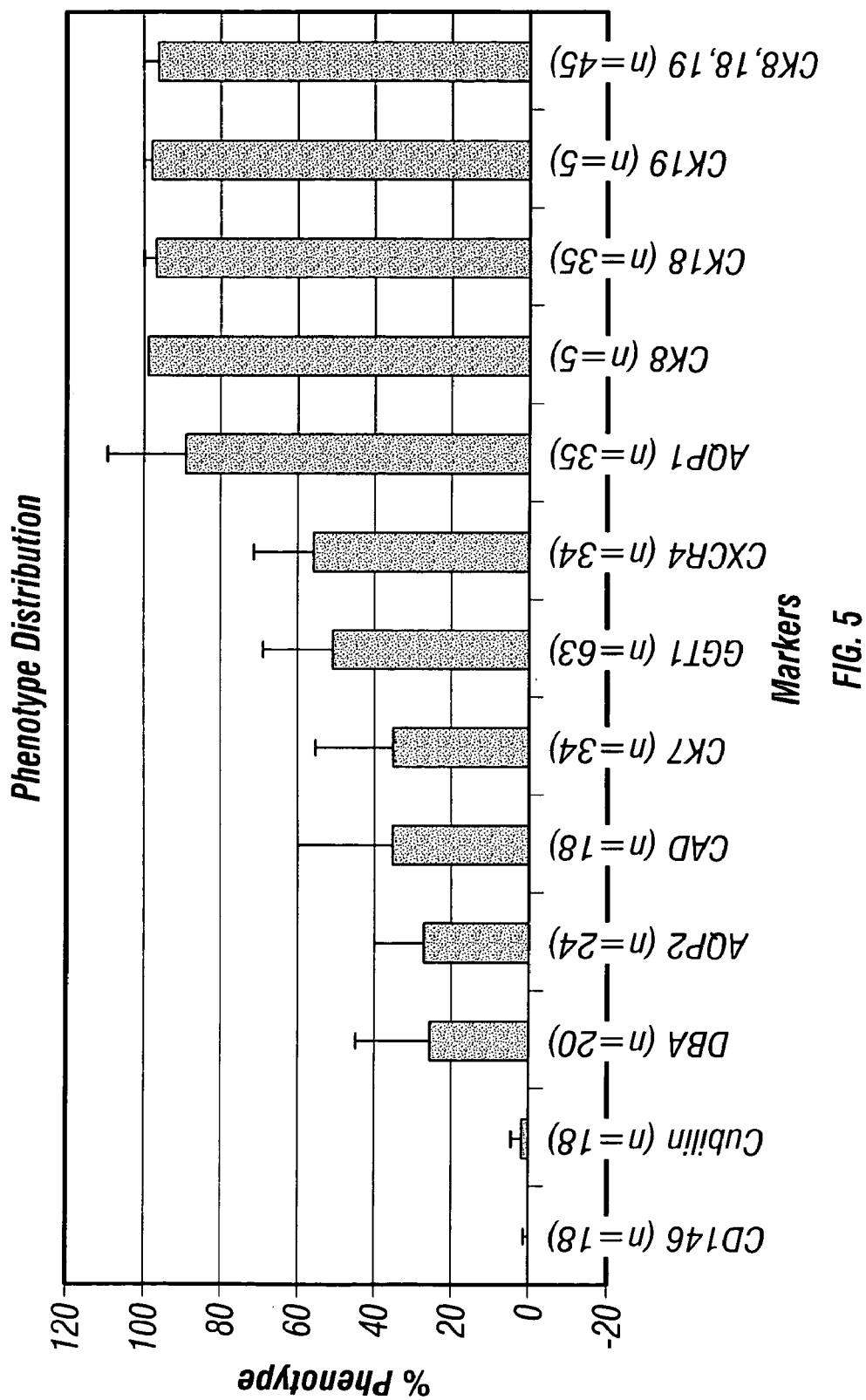
FIG. 5 is a bar graph depicting the expression of renal cell markers in human SRC populations. Reference is made to Example 12.
Figure 6:
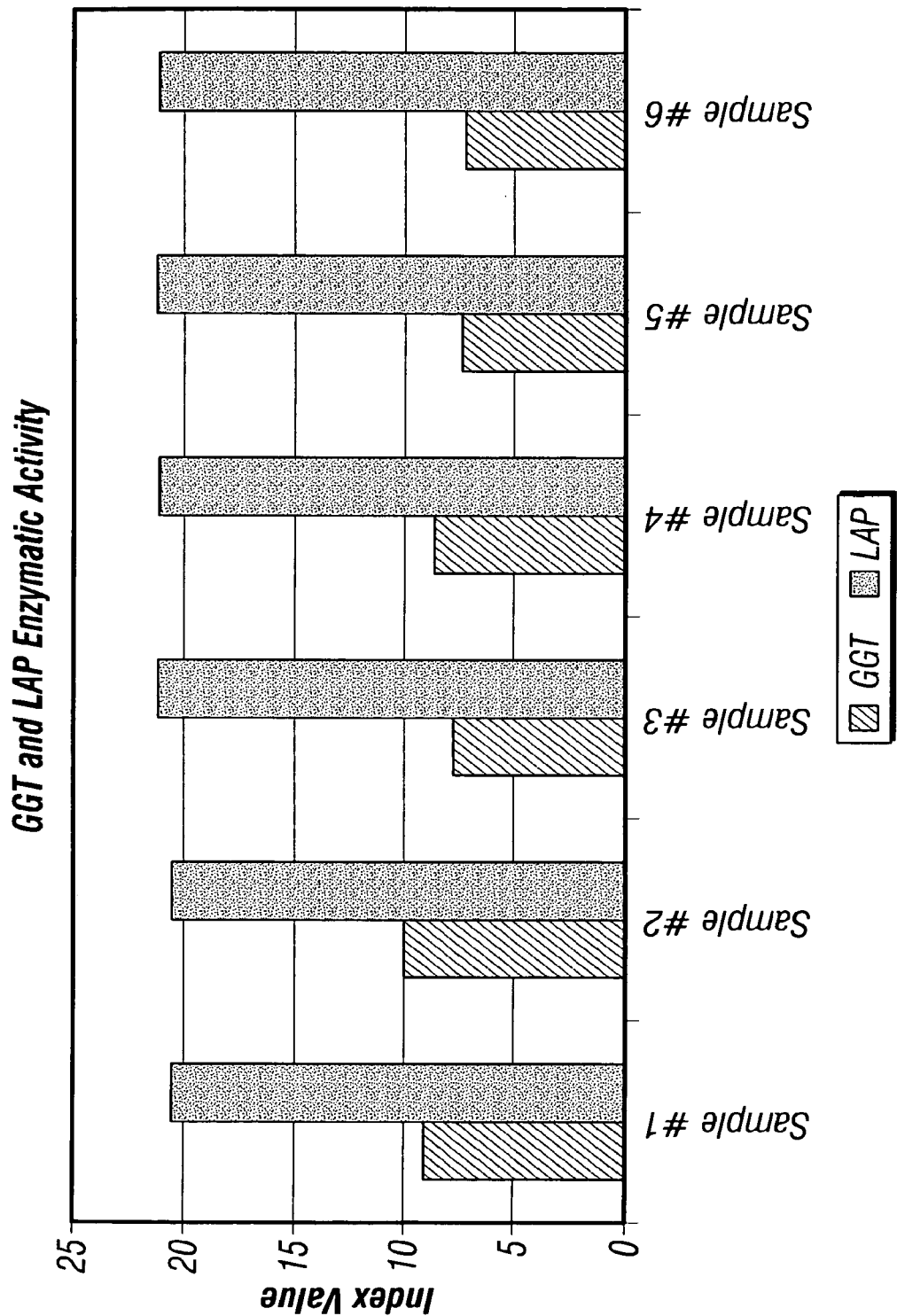
FIG. 6 is a bar graph depicting the enzymatic activity of human SRC. Reference is made to Example 12.
Figure 7A:
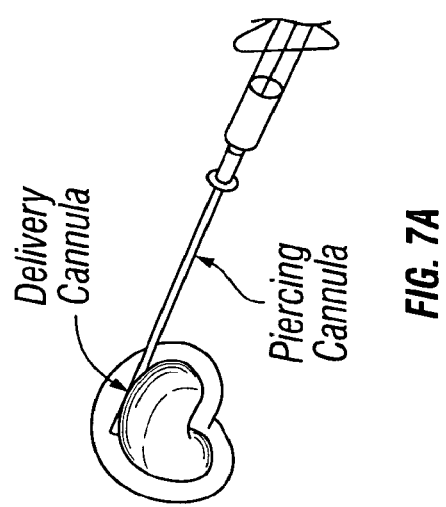
FIG. 7A-D depicts NKA injection in the kidney: (a) needle inserted into the kidney cortex, (b) NKA delivery, (c) multiple delivery points in the kidney, and (d) final implant of the NKA (exemplary).
Figure 7B:
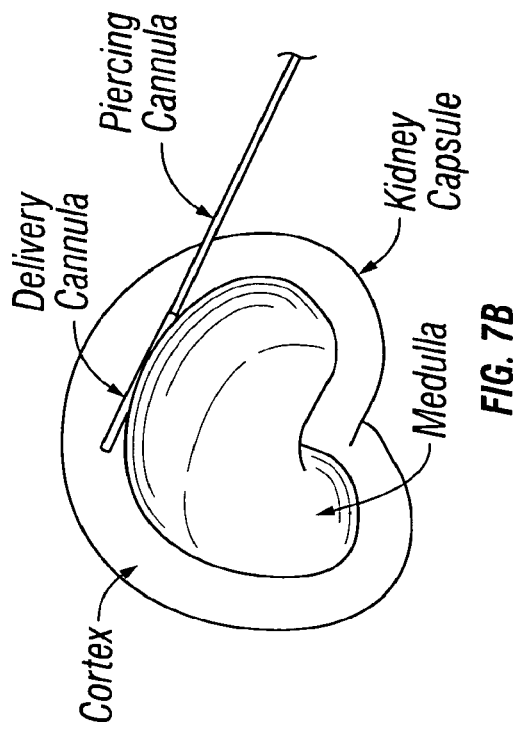
Figure 7C:
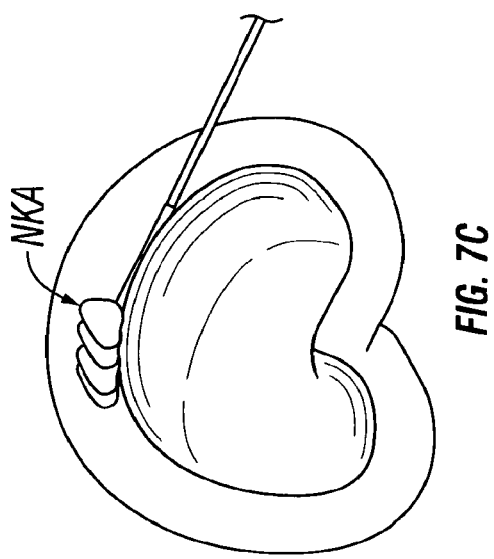
Figure 7D:
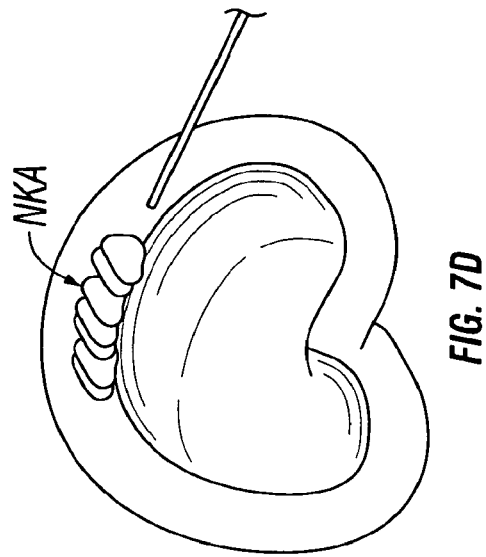

Human kidney tissues were procured from non-CKD and CKD human donors as summarized in Table 10.1 of Ilagan et al. PCT/US2011/036347. FIG. 4 of Ilagan et al. PCT/US2011/036347 shows histopathologic features of the HK17 and HK19 samples. Ex vivo cultures were established from all non-CKD (3/3) and CKD (5/5) kidneys. High content analysis (HCA) of albumin transport in human NKA cells defining regions of interest (ROI) is shown in FIG. 5 (HCA of albumin transport in human NKA cells) of Ilagan et al. PCT/US2011/036347. Quantitative comparison of albumin transport in NKA cells derived from non-CKD and CKD kidney is shown in FIG. 6 of Ilagan et al. PCT/US2011/036347. As shown in FIG. 6 of Ilagan et al. PCT/US2011/036347, albumin transport is not compromised in CKD-derived NKA cultures. Comparative analysis of marker expression between tubular-enriched B2 and tubular cell-depleted B4 subfractions is shown in FIG. 7 (CK8/18/19) of Ilagan et al. PCT/US2011/036347.

Comparative functional analysis of albumin transport between tubular-enriched B2 and tubular cell-depleted B4 subfractions is shown in FIG. 8 of Ilagan et al. PCT/US2011/036347. Subfraction B2 is enriched in proximal tubule cells and thus exhibits increased albumin-transport function.

Albumin uptake: Culture media of cells grown to confluency in 24-well, collagen IV plates (BD Biocoat™) was replaced for 18-24 hours with phenol red-free, serum-free, low-glucose DMEM (pr-/s-/lg DMEM) containing 1× antimycotic/antibiotic and 2 mM glutamine. Immediately prior to assay, cells were washed and incubated for 30 minutes with pr-/s-/lg DMEM+10 mM HEPES, 2 mM glutamine, 1.8 mM CaCl2, and 1 mM MgCl2. Cells were exposed to 25 μg/mL rhodamine-conjugated bovine albumin (Invitrogen) for 30 min, washed with ice cold PBS to stop endocytosis and fixed immediately with 2% paraformaldehyde containing 25 μg/mL Hoechst nuclear dye. For inhibition experiments, 1 μM receptor-associated protein (RAP) (Ray Biotech, Inc., Norcross GA) was added 10 minutes prior to albumin addition. Microscopic imaging and analysis was performed with a BD Pathway™ 855 High-Content BioImager (Becton Dickinson) (see Kelley et al. Am J Physiol Renal Physiol. 2010 November; 299(5):F1026-39. Epub Sep. 8, 2010).

In conclusion, HCA yields cellular level data and can reveal populations dynamics that are undetectable by other assays, i.e., gene or protein expression. A quantifiable ex-vivo HCA assay for measuring albumin transport (HCA-AT) function can be utilized to characterize human renal tubular cells as components of human NKA prototypes. HCA-AT enabled comparative evaluation of cellular function, showing that albumin transport-competent cells were retained in NKA cultures derived from human CKD kidneys. It was also shown that specific subfractions of NKA cultures, B2 and B4, were distinct in phenotype and function, with B2 representing a tubular cell-enriched fraction with enhanced albumin transport activity. The B2 cell subpopulation from human CKD are phenotypically and functionally analogous to rodent B2 cells that demonstrated efficacy in vivo (as shown above).

Example 7

Low-Oxygen Culture Prior to Gradient Affects Band Distribution, Composition, & Gene Expression To determine the effect of oxygen conditions on distribution and composition of prototypes B2 and B4, neokidney cell preparations from different species were exposed to different oxygen conditions prior to the gradient step. A rodent neo-kidney augmentation (NKA) cell preparation (RK069) was established using standard procedures for rat cell isolation and culture initiation, as described in Kelley et al., 2010, supra. All flasks were cultured for 2-3 days in 21% (atmospheric) oxygen conditions. Media was changed and half of the flasks were then relocated to an oxygen-controlled incubator set to 2% oxygen, while the remaining flasks were kept at the 21% oxygen conditions, for an additional 24 hours. Cells were then harvested from each set of conditions using standard enzymatic harvesting procedures described supra. Step gradients were prepared according to standard procedures and the "normoxic" (21% oxygen) and "hypoxic" (2% oxygen) cultures were harvested separately and applied side-by-side to identical step gradients. While 4 bands and a pellet were generated in both conditions, the distribution of the cells throughout the gradient was different in 21% and 2% oxygen-cultured batches (Table 7.1). Specifically, the yield of B2 was increased with hypoxia, with a concomitant decrease in B3. Furthermore, the expression of B4-specific genes (such as erythropoietin) was enhanced in the resulting gradient generated from the hypoxic-cultured cells (FIG. 73 of Presnell et al. WO/2010/056328).

A canine NKA cell preparation (DK008) was established using standard procedures for dog cell isolation and culture (analogous to rodent isolation and culture procedures), as described in Basu et al., WO 2012/064369. All flasks were cultured for 4 days in 21% (atmospheric) oxygen conditions, then a subset of flasks were transferred to hypoxia (2%) for 24 hours while a subset of the flasks were maintained at 21%. Subsequently, each set of flasks was harvested and subjected to identical step gradients. Similar to the rat results, the hypoxic-cultured dog cells distributed throughout the gradient differently than the atmospheric oxygen-cultured dog cells (Table 7.1). Again, the yield of B2 was increased with hypoxic exposure prior to gradient, along with a concomitant decrease in distribution into B3.

TABLE 7.1

|    | Rat (RK069) | | Dog (DK008) | |
|    | 2% O2 | 21% O2 | 2% O2 | 21% O2 |
| --- | --- | --- | --- | --- |
| B1 | 0.77% | 0.24% | 1.20% | 0.70% |
| B2 | 88.50% | 79.90% | 64.80% | 36.70% |
| B3 | 10.50% | 19.80% | 29.10% | 40.20% |
| B4 | 0.23% | 0.17% | 4.40% | 21.90% |

The above data show that pre-gradient exposure to hypoxia enhances composition of B2 as well as the distribution of specific specialized cells (erythropoietin-producing cells, vascular cells, and glomerular cells) into B4. Thus, hypoxic culture, followed by density-gradient separation as described in Basu et al., supra, is an effective way to generate 'B2' and 'B4' cell populations, across species.

Example 8

Characterization of an Unfractionated Mixture of Renal Cells Isolated from an Autoimmune Glomerulonephritis Patient Sample An unfractionated mixture of renal cells was isolated, as described above, from an autoimmune glomerulonephritis patient sample. To determine the unbiased genotypic composition of specific subpopulations of renal cells isolated and expanded from kidney tissue, quantitative real time PCR (qRTPCR) analysis (Brunskill et al., Dev. Cell. 2008 November; 15(5):781-791) was employed to identify differential cell-type-specific and pathway-specific gene expression patterns among the cell subfractions. As shown in Table 6.1 of Ilagan et al. PCT/US2011/036347, HK20 is an autoimmune glomerulonephritis patient sample. As shown in Table 6.2 of Ilagan et al. PCT/US2011/036347, cells generated from HK20 are lacking glomerular cells, as determined by qRTPCR.

Example 9

Genetic Profiling of Therapeutically Relevant Renal Bioactive Cell Populations Isolated from a Case of Focal Segmental Glomerulosclerosis To determine the unbiased genotypic composition of specific subpopulations of renal cells isolated and expanded from kidney tissue, quantitative real time PCR (qRTPCR) analysis (Brunskill et al., supra 2008) was employed to identify differential cell-type-specific and pathway-specific gene expression patterns among the cell subfractions. Human preparation HK023, derived from a case of focal segmental glomerulosclerosis (FSGS) in which a large portion of glomeruli had been destroyed, was evaluated for presence of glomerular cells in the B4 fraction at the time of harvest. In brief, unfractionated (UNFX) cultures were generated (Aboushwareb et al., World J Urol 26, 295, 2008) and maintained independently from each of (4) core biopsies taken from the kidney using standard biopsy procedures. After (2) passages of UNFX ex vivo, cells were harvested and subjected to density gradient methods according to Example 6 of Basu et al., WO2012/064369 to generate subfractions, including subfraction B4, which is known to be enriched for endocrine, vascular, and glomerular cells based on work conducted in rodent, dog, and other human specimens.

The B4 fractions were collected separately from each independent UNFX sample of HK023, appearing as distinct bands of cells with buoyant density between 1.063-1.091 g/mL. RNA was isolated from each sample and examined for expression of Podocin (glomerular cell marker) and PECAM (endothelial cell marker) by quantitative real-time PCR. As expected from a biopsy-generated sample from a case of severe FSGS, the presence of podocin(+) glomerular cells in B4 fractions was inconsistent, with podocin undetectable in 2/4 of the samples. In contrast, PECAM+ vascular cells were consistently present in the B4 fractions of 4/4 of the biopsy-initiated cultures. Thus, the B4 fraction can be isolated at the 1.063-1.091 g/mL density range, even from human kidneys with severe disease states.

TABLE 9.1

Expression of Podocin and PECAM for detection of glomerular and vascular cells in subfraction B4 isolated from a case of FSGS.

| HK023/Biopsy | RQ (Podocin)/B4 | RQ (PECAM)/B4 |
|---|---|---|
| #1/p2 | 0.188 | 0.003 |
| #2/p2 | ND | 0.02 |
| #3/p2 | 40.1 | 0.001 |
| #4/p2 | ND | 0.003 |

Further, as shown in Table 7.2 of Ilagan et al. PCT/US2011/036347, human sample (HK018) displayed undetected Podocin (glomerular marker) by qRTPCR after density gradient centrifugation.

Example 10

Enrichment/Depletion of Viable Kidney Cell Types Using Fluorescent Activated Cell Sorting (FACS)

One or more isolated kidney cells may be enriched, and/or one or more specific kidney cell types may be depleted from isolated primary kidney tissue using fluorescent activated cell sorting (FACS).

REAGENTS: 70% ethanol; Wash buffer (PBS); 50:50 Kidney cell medium (50% DMEM high glucose): 50% Keratinocyte-SFM; Trypan Blue 0.4%; Primary antibodies to target kidney cell population such as CD31 for kidney endothelial cells and Nephrin for kidney glomerular cells. Matched isotype specific fluorescent secondary antibodies; Staining buffer (0.05% BSA in PBS).

PROCEDURE: Following standard procedures for cleaning the biological safety cabinet (BSC), a single cell suspension of kidney cells from either primary isolation or cultured cells may be obtained from a T500 T/C treated flask and resuspend in kidney cell medium and place on ice. Cell count and viability is then determined using trypan blue exclusion method. For kidney cell enrichment/depletion of, for example, glomerular cells or endothelial cells from a heterogeneous population, between 10 and $50 \times 10^6$ live cells with a viability of at least 70% are obtained. The heterogeneous population of kidney cells is then stained with primary antibody specific for target cell type at a starting concentration of 1 µg/0.1 ml of staining buffer/$1 \times 10^6$ cells (titer if necessary). Target antibody can be conjugated such as CD31 PE (specific for kidney endothelial cells) or un-conjugated such as Nephrin (specific for kidney glomerular cells).

Cells are then stained for 30 minutes on ice or at 4° C. protected from light. After 30 minutes of incubation, cells are washed by centrifugation at 300×g for 5 min. The pellet is then resuspended in either PBS or staining buffer depending on whether a conjugated isotype specific secondary antibody is required. If cells are labeled with a fluorochrome conjugated primary antibody, cells are resuspended in 2 mls of PBS per $10^7$ cells and proceed to FACS aria or equivalent cell sorter. If cells are not labeled with a fluorochrome conjugated antibody, then cells are labeled with an isotype specific fluorochrome conjugated secondary antibody at a starting concentration of 1 µg/0.1 ml/$10^6$ cells.

Cells are then stained for 30 min. on ice or at 4° C. protected from light. After 30 minutes of incubation, cells are washed by centrifugation at 300×g for 5 min. After centrifugation, the pellet is resuspended in PBS at a concentration of $5 \times 10^6$/ml of PBS and then 4 mls per 12×75 mm is transferred to a sterile tube.

FACs Aria is prepared for live cell sterile sorting per manufacturer's instructions (BD FACs Aria User Manual). The sample tube is loaded into the FACs Aria and PMT voltages are adjusted after acquisition begins. The gates are drawn to select kidney specific cells types using fluorescent intensity using a specific wavelength. Another gate is drawn to select the negative population. Once the desired gates have been drawn to encapsulate the positive target population and the negative population, the cells are sorted using manufacturer's instructions.

The positive target population is collected in one 15 ml conical tube and the negative population in another 15 ml conical tube filled with 1 ml of kidney cell medium. After collection, a sample from each tube is analyzed by flow cytometry to determine purity. Collected cells are washed by centrifugation at 300×g for 5 min. and the pellet is resuspended in kidney cell medium for further analysis and experimentation.

Example 11

Enrichment/Depletion of Kidney Cell Types Using Magnetic Cell Sorting

One or more isolated kidney cells may be enriched and/or one or more specific kidney cell types may be depleted from isolated primary kidney tissue.

REAGENTS: 70% ethanol, Wash buffer (PBS), 50:50 Kidney cell medium (50% DMEM high glucose): 50% Keratinocyte-SFM, Trypan Blue 0.4%, Running Buffer (PBS, 2 mM EDTA, 0.5% BSA), Rinsing Buffer (PBS, 2 mM EDTA), Cleaning Solution (70% v/v ethanol), Miltenyi FCR Blocking reagent, Miltenyi microbeads specific for either IgG isotype, target antibody such as CD31(PECAM) or Nephrin, or secondary antibody.

PROCEDURE: Following standard procedures for cleaning the biological safety cabinet (BSC), a single cell suspension of kidney cells from either primary isolation or culture is obtained and resuspended in kidney cell medium. Cell count and viability is determined using trypan blue exclusion method. For kidney cell enrichment/depletion of, for example, glomerular cells or endothelial cells from a heterogeneous population, at least $10^6$ up to $4 \times 10^9$ live cells with a viability of at least 70% is obtained.

The best separation for enrichment/depletion approach is determined based on target cell of interest. For enrichment of a target frequency of less than 10%, for example, glomerular cells using Nephrin antibody, the Miltenyi autoMACS, or equivalent, instrument program POSSELDS (double positive selection in sensitive mode) is used. For depletion of a target frequency of greater than 10%, the Miltenyi autoMACS, or equivalent, instrument program DEPLETES (depletion in sensitive mode) is used.

Live cells are labeled with target specific primary antibody, for example, Nephrin rb polyclonal antibody for glomerular cells, by adding 1 µg/$10^6$ cells/0.1 ml of PBS with 0.05% BSA in a 15 ml conical centrifuge tube, followed by incubation for 15 minutes at 4° C.

After labeling, cells are washed to remove unbound primary antibody by adding 1-2 ml of buffer per $10^7$ cells followed by centrifugation at 300×g for 5 min. After washing, isotype specific secondary antibody, such as chicken anti-rabbit PE at 1 µg/$10^6$/0.1 ml of PBS with 0.05% BSA, is added, followed by incubation for 15 minutes at 4° C.

After incubation, cells are washed to remove unbound secondary antibody by adding 1-2 ml of buffer per $10^7$ cells followed by centrifugation at 300×g for 5 min. The supernatant is removed, and the cell pellet is resuspended in 60 μl of buffer per $10^7$ total cells followed by addition of 20 μl of FCR blocking reagent per $10^7$ total cells, which is then mixed well.

Add 20 μl of direct MACS microbeads (such as anti-PE microbeads) and mix and then incubate for 15 min at 4° C.

After incubation, cells are washed by adding 10-20× the labeling volume of buffer and centrifuging the cell suspension at 300×g for 5 min. and resuspending the cell pellet in 500 μl-2 mls of buffer per $10^8$ cells.

Per manufacturer's instructions, the autoMACS system is cleaned and primed in preparation for magnetic cell separation using autoMACS. New sterile collection tubes are placed under the outlet ports. The autoMACS cell separation program is chosen. For selection the POSSELDS program is chosen. For depletion the DEPLETES program is chosen.

The labeled cells are inserted at uptake port, then beginning the program. After cell selection or depletion, samples are collected and placed on ice until use. Purity of the depleted or selected sample is verified by flow cytometry.

Example 12

Phenotypic Characterization of the Enriched Heterogeneous Renal Cell Population

The following example details the use of flow cytometry to characterize the selected heterogeneous human renal cells of Example 5. The heterogeneous renal cell population was composed primarily of renal epithelial cells that are well known for their regenerative potential. Other parenchymal (vascular) and stromal (collecting duct) cells may be sparsely present in the autologous cell population.

Cell phenotype is monitored by expression analysis of renal cell markers using flow cytometry. Phenotypic analysis of cells is based on the use of antigenic markers specific for the cell type being analyzed. Flow cytometric analysis provides a quantitative measure of cells in the sample population which express the antigenic marker being analyzed.

A variety of markers have been reported in the literature as being useful for phenotypic characterization of renal cells: (i) cytokeratins; (ii) transport membrane proteins (aquaporins and cubilin); (iii) cell binding molecules (adherins, cluster of differentiation, and lectins); and (iv) metabolic enzymes (glutathione). Since the majority of cells found in cultures derived from whole kidney digests are epithelial and endothelial cells, the markers examined focus on the expression of proteins specific for these two groups.

Cytokeratins are a family of intermediate filament proteins expressed by many types of epithelial cells to varying degrees. The subset of cytokeratins expressed by an epithelial cell depends upon the type of epithelium. For example, cytokeratins 7, 8, 18 and 19 are all expressed by normal simple epithelia of the kidney and remaining urogenital tract as well as the digestive and respiratory tracts. These cytokeratins in combination are responsible for the structural integrity of epithelial cells. This combination represents both the acidic (type I) and basic (type II) keratin families and is found abundantly expressed in renal cells (Oosterwijk et al., J Histochem Cytochem, 38(3):385-392, 1990). Preferred cytokeratins for use herein are CK8, CK18, CK19 and combinations thereof.

Aquaporins are transport membrane proteins which allow the passage of water into and out of the cell, while preventing the passage of ions and other solutes. There are thirteen aquaporins described in the literature, with six of these being found in the kidney (Nielsen et al., J Histochem Cytochem, 38(3):385-392, 2002). Aquaporin2, by exerting tight control in regulating water flow, is responsible for the plasma membranes of renal collecting duct epithelial cells having a high permeability to water, thus permitting water to flow in the direction of an osmotic gradient (Bedford et al., J Am Soc Nephrol, 14(10):2581-2587, 2003; Takata et al., Histochem Cell Biol, 130(2):197-209, 2008; Tamma et al., Endocrinology, 148(3):1118-1130, 2007). Aquaporin1 is characteristic of the proximal tubules (Baer et al., Cells Tissues Organs: 184(1), 16-22, 2006; Nielsen et al., 2002, supra).

Cubilin is a transport membrane receptor protein. When it co-localizes with the protein megalin, together they promote the internalization of cubilin-bound ligands such as albumin. Cubilin is located within the epithelium of the intestine and the kidney (Christensen. Am J Physiol Renal Physiol, 280 (4):F562-573, 2001).

CXCR4 is a transport membrane protein which serves as a chemokine receptor for SDF1. Upon ligand binding, intracellular calcium levels increase and MAPK1/MAPK3 activation is increased. CXCR4 is constitutively expressed in the kidney and plays an important role in kidney development and tubulogenesis (Ueland et al., Dev Dyn, 238(5): 1083-1091, 2009).

Cadherins are calcium-dependent cell adhesion proteins. They are classified into four groups, with the E-cadherins being found in epithelial tissue, and are involved in regulating mobility and proliferation. E-cadherin is a transmembrane glycoprotein which has been found to be localized in the adherins junctions of epithelial cells which make up the distal tubules in the kidney (Prozialeck et al., BMC Physiol, 4:10, 2004; Shen et al., Mod Pathol, 18(7):933-940, 2005).

DBA (Dolichos biflorus agglutinin) is an α-N-acetylgalactosamine-binding lectin (cell binding protein) carried on the surface of renal collecting duct structures, and is regarded and used as a general marker of developing renal collecting ducts and distal tubules (Michael et al., J Anat 210(1):89-97, 2007; Lazzeri et al., J Am Soc Nephrol 18 (12):3128-3138, 2007).

Cluster of differentiation 31 (CD31; also known as platelet endothelial cell adhesion molecule, PECAM-1) is a cell adhesion protein which is expressed by select populations of immune cells as well as endothelial cells. In endothelial cells, this protein is concentrated at the cell borders (DeLisser, 1997). Cluster of differentiation 146 (CD146) is involved in cell adhesion and cohesion of endothelial cells at intercellular junctions associated with the actin cytoskeleton. Strongly expressed by blood vessel endothelium and smooth muscle, CD146 is currently used as a marker for endothelial cell lineage (Malyszko et al., J Clin Endocrinol Metab, 89(9):4620-4627, 2004), and is the canine equivalent of CD31.

Gamma-glutamyl transpeptidase (GGT) is a metabolic enzyme that catalyzes the transfer of the gamma-glutamyl moiety of glutathione to an acceptor that may be an amino acid, a peptide, or water, to form glutamate. This enzyme also plays a role in the synthesis and degradation of glutathione and the transfer of amino acids across the cell membrane. GGT is present in the cell membranes of many tissues, including the proximal tubule cells of kidneys (Horiuchi et al., Eur J Biochem, 87(3):429-437, 1978; Pretlow et al., J Histochem Cytochem, 35(4):483-487, 1987; Welbourne et al., Am J Physiol, 277(4 Pt 2):F501-505, 1999). Table 12.1 provides a list of the specific types of renal cells expressing these markers as detected by flow cytometry.

TABLE 12.1

Phenotypic Markers for SRC Characterization

| Antigenic Marker | Reactivity |
|---|---|
| CK8/18/19 | Epithelial cells, proximal and distal tubules |
| CK8 | Epithelial cells, proximal tubules |
| CK18 | Epithelial cells, proximal tubules |
| CK19 | Epithelial cells, collecting ducts, distal tubules |
| CK7 | Epithelial cells, collecting ducts, distal tubules |
| CKCR4 | Epithelial cells, proximal and distal tubules |
| E-cadherin | Epithelial cells, distal tubules |
| Cubilin | Epithelial cells, proximal tubules |
| Aquaporin 1 | Epithelial cells, proximal tubules, descending thin limb |
| GGT1 | Fetal and adult kidney cells, proximal tubules |
| Aquaporin2 | Renal collecting duct cells, distal tubules |
| DBA | Renal collecting duct cells, distal tubules |
| CD31 | Endothelial cells of the kidney (rat) |
| CD146 | Endothelial cells of the kidney (canine, human) |

The SRC cells of Example 5 were investigated for phenotype of specific biomarkers.

For immunophenotyping: The specific antibody was added to 100 microliters of cell suspension and the mixture was incubated in the dark for 30-45 minutes at 4° C. After incubation, cells were washed with PBS and centrifuged to remove excess antibody. Cells were resuspended to cells/microliters PBS and analyzed by flow cytometry. Flow cytometry analysis was performed with a FACSAria flow cytometer (Becton Dickinson) and FlowJo software (Treestar, Inc.). Antibodies used to characterize the surface marker phenotype are shown in Tables 12.2 and 12.3. Isotype-specific primary antibody negative controls were used in all experiments. Appropriate isotype-matched controls were used to gate negative populations.

TABLE 12.2

Phenotype Panel for Human SRC in NKA Reported in IND

| Antigenic Marker | Kidney Distribution | Cell Component | Commercial Description |
|---|---|---|---|
| Primary Phenotypic Profile | | | |
| CK18 | Epithelial cells, proximal tubules | Cytoplasmic | C-04 clone, Ms mAb IgG1, Abcam ab668 |
| GGT1 | Proximal tubules | Membrane | Ms mAb IgG2a, Abcam ab55138 |
| AQP2 | Distal tubules, collecting ducts | Membrane | Rb pAb IgG, Abcam ab62628 |
| Expanded Phenotypic Panel | | | |
| CK8, 18, 19 | Proximal and distal tubules | Cytoplasmic | Ms mAb IgG1, Abcam ab41825 |
| CK8 | Proximal tubules | Cytoplasmic | Ms mAb IgG1, Abcam ab9023 |
| CK19 | Distal tubules, collecting ducts | Cytoplasmic | Clone 8A-17, Ms mAb Abcam ab7755 |
| CK7 | Distal tubules, collecting ducts | Cytoplasmic | Ms mAb IgG1, Abcam ab41825 |
| CXCR4 (Fusin) | Proximal and distal tubules | Membrane | Clone 12G5, Ms mAb IgG2a, R&D Systems MAB170 |
| E-cadherin (CD324) | Distal tubules | Membrane | Ms mAb IgG2a, BD 610182 |
| Cubilin | Proximal tubules | Membrane | Gt pAb IgG, Santa Cruz Biotechnology, sc-23644 |
| AQP1 | Proximal tubules, descending thin limb | Membrane | Clone 1/22, Ms mAb IgG2a, Abcam ab9566 |
| DBA | Distal tubules, collecting ducts | Membrane | Agglutinin, Vector Labs B-1035 |
| CD31 (PECAM-1) | Endothelial cells (rat) | Membrane | Ms mAb IgG1, BD 555444 |
| CD146 | Endothelial cells (human, dog) | Membrane | Clone P1H12, Ms mAb IgG1, Abcam ab24577 |

Abbreviations: Gt, goat; Ms, mouse; mAb, monoclonal antibody; pAb, polyclonal antibody; Rb, rabbit.

TABLE 12.3

Additional Phenotypic Markers for Evaluation of Human SRC

| Antigenic Marker | Kidney Distribution | Commercial Description |
|---|---|---|
| AQP4 | Collecting ducts | Clone 8J301, Ms mAb IgG1, US Biological A3000-14B |
| CD24 | Glomerulus and proximal tubules (progenitor/stem cell marker) | Rb pAb IgG, Abcam ab110448 |
| CD54 (ICAM-1) | Glomerulus (endothelial cells, human) | Clone HA58, Ms mAb IgG1, BD 559771 |
| CD73 | Renal Cortex (interstitial fibroblasts) | Gt pAb IgG, Santa Cruz Biotechnology, sc-14684 |
| CD117 | Proximal tubules (stem cell marker) | Clone 104D2, Ms mAb 104D2, BD 340867 |
| CD133 | Glomerulus and proximal tubules (progenitor/stem cell marker) | Rb pAb IgG, Abcam ab19898 |
| CK8, 18 | Proximal and distal tubules | Ms mAb IgG2a, Abcam ab15224 |
| CK40 to 67 | Proximal tubules | Clone AE1/AE3, Ms mAb IgG1, Dako M3515 |
| N-cadherin | Proximal tubules | Ms mAb IgG1, BD 610921 |
| Pan-cadherin | Proximal tubules | Clone CH-19, Ms mAb IgG1, Abcam ab6528 |
| Calbindin | Distal tubules | Ms mAb IgG1, US Biological C0113-15 |
| Calponin | Glomerulus (interstitial fibroblasts) | Ms mAb IgG1, Dako M3556 |
| Connexin 43 | Glomerulus | Clone 4EG.2, Ms mAb IgG1, Abcam ab79010 |
| EPO (erythropoeitin) | Renal Cortex (interstitial fibroblasts) | Ms mAb IgG2a, US Biological E3455-13 |
| GLEPP1 (glomerular epithelial protein 1) | Glomerulus | Gt pAb IgG, Santa Cruz Biotechnology sc-33415 |
| ☐GST-1 (alpha glutathione S-transferase) | Proximal tubules | Rb pAb IgG, Santa Cruz Biotechnology sc-459 |
| Haptoglobulin | Glomerulus | Chicken IgY, US Biological 03-003-02 |
| Itgb1 (Integrin;☐1) | Collecting ducts | Clone JB1B, Ms mAb IgG2a, Abcam ab30388 |
| KIM-1/TIM-1 (kidney injury molecule-1/T-cell immunoglobulin and mucin-containing molecule) | Proximal tubules | Clone 212211, Ms mAb IgG2b, R&D Systems MAB1750 |
| Megalin | Proximal and distal tubules | Rb pAb IgG, Santa Cruz Biotechnology, sc-25470 |
| MAP-2 | Proximal and | Clone M13, Ms mAb IgG1, |

TABLE 12.3-continued

Additional Phenotypic Markers for Evaluation of Human SRC

| Antigenic Marker | Kidney Distribution | Commercial Description |
|---|---|---|
| (microtubule-associated protein 2) | distal tubules | Zymed/Life Technologies 13-1500 |
| Nephrin | Glomerulus | Ms mAb IgG1, US Biological N2028-50D |
| NKCC (Na—K—Cl-cotransporters) | Distal tubules | Rb pAb IgG, Santa Cruz Biotechnology sc-133823 |
| OAT-1 (organic anion transporter 1) | Proximal tubules | Rb pAb IgG, US Biological 041836 |
| Osteopontin | Proximal and distal tubules | Clone 53, Ms mAb IgG2a, Abcam 69498 |
| PCLP1 podocalyxin-like 1 molecule) | Glomerulus | Gt pAb IgG, Santa Cruz Biotechnology sc-10503 |
| Podocin | Glomerulus | Rb pAb IgG, Santa Cruz Biotechnology sc-21009 |
| SMA (smooth muscle alpha-actin) | Glomerulus (interstitial fibroblasts) | Ms mAb IgG2a, Dako M0851 |
| Synaptopodin | Glomerulus | Rb pAb IgG, Santa Cruz Biotechnology sc-50459 |
| THP (tamm-horsfall protein) | Distal tubules | Ms mAb IgG2a, Santa Cruz Biotechnology sc-20631 |
| Vimentin | Proximal tubules (progenitor/stem cell marker) | Rb pAb IgG, Atlas Antibodies HPA001762 |

Cell suspensions were generated from initial tissue dissociation or trypsinization of adherent cultures and analyzed by flow cytometry to identify cellular components. Antibodies employed are listed in Tables 12.2 and 12.3 (above). Isotype-specific primary antibody negative controls were used in all experiments. Labeled cells were analyzed with a FACSAria flow cytometer (Becton Dickinson) and FlowJo software (Treestar, Inc.). Appropriate isotype-matched controls were used to gate negative populations. After an overnight incubation at 4° C., the cells were pelleted, washed twice with Triton Buffer (0.2% Triton X-100 in PBS), resuspended in 1 mL of DBPS containing secondary antibody goat anti-mouse IgG2A conjugated to the fluorochrome Alexa A647 (Invitrogen), and incubated for an additional 30 minutes. Cells were then washed and resuspended in 1 mL of PBS for analysis as per manufacturer instructions using FACSAria and FlowJo software. As a negative control, cells were incubated in parallel with isotype-matched monoclonal antibodies conjugated to the same fluorochrome.

FIG. 5 (Phenotype Distribution) shows quantified expression of these markers in SRC populations plotted as percentage values of each phenotype in the population.

CK8/18/19 are the most consistently expressed renal cell proteins detected across species. GGT1 and Aquaporin-1 (AQP1) are expressed consistently but at varying levels. DBA, Aquaporin2 (AQP2), E-cadherin (CAD), CK7, and CXCR4 are also observed at modest levels though with more variability, and CD31/146 and Cubilin were lowest in expression. Table 12.4 provides the selected markers, range and mean percentage values of phenotypic in SRC and the rationale for their selection.

TABLE 12.4

Marker Selected for Phenotypic Analysis of SRC

| Phenotypic Marker | Expression Range | Average | Rationale | Expression level |
|---|---|---|---|---|
| CK18 | 81.1 to 99.7% (n = 87) | 96.7% | Epithelial marker | High |
| GGT1 | 4.5 to 81.2% (n = 63) | 50.7% | Functional Tubular marker | Moderate |
| AQP2 | 3.0 to 53.7% (n = 24) | 26.8% | Collecting duct marker | Low* |

*Collecting duct epithelial cells are expected to be low in SRC based on their buoyant density SRC Gene Expression The gene expression profile of SRC isolated from human renal cell cultures by quantitative real-time polymerase chain reaction (qPCR), including those of aquaporin2, E-cadherin, cubulin, VEGF and CD31 that were also tested for protein production. Genotypic markers in Table 12.5 are representative of cell populations that might be expected to be found in the renal cell cultures. NCAD, Cubilin and CYP2R1 are markers of tubular epithelial cells, AQP2 and ECAD are markers of collecting duct and distal tubules. Podocin and Nephrin are markers of podocytes. VEGF and CD31 are endothelial markers. VEGF and EPO are oxygen responsive genes with related mRNA present in a variety of different tissue and cell types.

Gene probes used were obtained from TaqMan. Passage 2 human renal cells were harvested at 70-90% confluence. RNA was purified from the cells using Qiagen's RNeasy Plus Mini Kit following the protocol for Purification of Total RNA from Animal Cells. cDNA was generated from a volume of RNA equal to 1.4 μg using Invitrogen's SuperScript® VILO™ cDNA Synthesis Kit following the manufacturer's instructions. Averaged qPCR data for SRC populations (n=3) is shown in Table 12.5.

The results suggest that a population of tubular epithelial cells is present as evidenced by relatively higher level of expression of NCAD, Cubilin and CYP2R1. Distal Collecting Duct Tubule and Distal Tubule markers AQP2 and ECAD are relatively low and CD31, an endothelial marker is even lower (Table 12.5).

TABLE 12.5

Gene Expression Analysis of Human SRC

| Gene Name | Gene Designation | Marker | Human Average RQ | Std Error |
|---|---|---|---|---|
| Aquaporin2 | AQP2 | Distal Tubule, Collecting Duct | 0.201 | 0.201 |
| E-cadherin/ Cadherin 1, Type 1 | ECAD/ CDH1 | Distal Tubule | 0.318 | 0.191 |
| Neuronal Cadherin/ Cadherin 2, Type 1 | NCAD/ CDH2 | Proximal Tubule | 3.027 | 0.208 |
| Cubilin | CUBN | Tubular | 4.319 | 1.036 |
| Nephrin | NPHS1 | Podocyte | 0.768 | 0.422 |
| Podocin | NPHS2 | Podocyte | 0.000 | 0.000 |
| Erythropoietin | EPO | Cortical Fibroblast | 2.795 | 0.426 |
| Vitamin D 24-Hydroxylase | CYP2R1 | Tubular | 1.562 | 0.028 |

TABLE 12.5-continued

Gene Expression Analysis of Human SRC

| Gene Name | Gene Designation | Marker | Human Average RQ | Std Error |
|---|---|---|---|---|
| Vascular Endothelial Growth Factor A | VEGFA | Endothelial | 2.232 | 0.121 |
| Platelet/ Endothelial Cell Adhesion Molecule/CD31 | PECAM1/ CD31 | Endothelial | 0.005 | 0.005 |

Phenotypic and functional markers have been chosen based upon early genotypic evaluation. VEGF gene expression levels were high and aquaporin2 gene expression levels were low which is consistent with the protein analysis data (Table 12.4 and Table 12.6).

SRC Enzymatic Activity

Presence of viable cells and SRC function was demonstrated by metabolism of PrestoBlue and production of VEGF and KIM-1.

SRC actively secrete proteins that can be detected through analysis of conditioned medium. Cell function is assessed by the ability of cells to metabolize PrestoBlue and secrete VEGF (Vascular Endothelial Growth Factor) and KIM-1 (Kidney Injury Molecule-1).

Viable functioning cells can be monitored in NKA by their ability to metabolize PrestoBlue. PrestoBlue Cell Viability Reagent is a modified resazurin-based assay reagent that is a cell permeable, non-fluorescent blue dye. Upon entry into cells which are sufficiently viable to proliferate, the dye is reduced, via natural cell processes involving dehydrogenase enzymes, to a bright red fluorophore that can be measured by fluorescence or absorbance.

Biomolecules VEGF and KIM-1 represent a selection of molecules from those proposed as sensitive and specific analytical nonclinical biomarkers of kidney injury and function (Sistare, 2010; Warnock, 2010). In vivo, both of these markers are indicative of tubular function, injury and/or repair and in vitro are recognized features of tubular epithelial cell cultures. KIM-1 is an extracellular protein anchored in the membrane of renal proximal tubule cells that serves to recognize and phagocytose apoptotic cells which are shed during injury and cell turnover. VEGF, constitutively expressed by kidney cells, is a pivotal angiogenic and pro-survival factor that promotes cell division, migration, endothelial cell survival and vascular sprouting. SRC have been characterized as constitutively expressing VEGF mRNA (Table 12.5) and actively produce the protein (Table 12.6). These proteins may be detected in culture medium exposed to renal cells and SRC. Table 12.6 presents VEGF and KIM-1 quantities present in conditioned medium from renal cells and SRC cultures. Renal cells were cultured to near confluence. Conditioned medium from overnight exposure to the renal cell cultures and SRC was tested for VEGF and KIM-1.

TABLE 12.6

Production of VEGF and KIM-1 by Human Renal Cells and SRC

| Conditioned Medium | VEGF ng/mL | VEGF ng/million cells | KIM-1 ng/mL | KIM-1 ng/million cells |
|---|---|---|---|---|
| Renal Cell Culture (n = 15) | 0.50 to 2.42 | 2.98 to 14.6 | 0.20 to 3.41 | 1.14 to 15.2 |
| SRC (n = 14) | 0.80 to 3.85 | 4.83 to 23.07 | 0.32 to 2.10 | 1.93 to 12.59 |

Cell function of SRC, pre-formulation, was also evaluated by measuring the activity of two specific enzymes; GGT (γ-glutamyl transpeptidase) and LAP (leucine aminopeptidase) (Chung, 1982, J Cell Biol 95(1):118-126), found in kidney proximal tubules. Methods to measure the activity of these enzymes in cells utilize an enzyme-specific substrate in solution that, when added to cells expressing active enzyme, are cleaved, releasing a chromogenic product (Nachlas, 1960 J Biophys Biochem Cytol 7:261-264; Tate, 1974 Proc Natl Acad Sci USA 71(9):3329-3333). The absorbance of the cell-exposed solution is measured and is relative to the amount of cleavage product resulting from active enzyme. The substrate utilized for GGT is L-glutamic acid γ-p-nitroanalide hydrochloride and for LAP is L-leucine p-nitroanalide. FIG. 6 shows LAP and GGT activity in six SRC samples produced from human donors (BP1-BP4).

Summary of SRC Characterization

Cell morphology was monitored during cell expansion by comparison of culture observations with images in an Image Library. Cell growth kinetics were monitored at each cell passage. Cell growth is expected to be variable from patient to patient. SRC counts and viability were monitored by Trypan Blue dye exclusion and/or metabolism of Presto-Blue. SRC are characterized by phenotypic expression of CK18, GGT1. In addition AQP2 expression may be monitored. Metabolism of PrestoBlue and production of VEGF and KIM-1 are used as markers for the presence of viable and functional SRC. SRC function can be further elucidated with gene expression profiling and measurement of enzymatic activity with LAP and GGT.

Example 13

BioMaterial Preparation

The Biomaterial used in NKA (Gelatin Solution) is characterized via two key parameters:
  Concentration—Concentration of Gelatin Solution is measured by absorbance at 280 nm using a spectrophotometer. The gelatin concentration is determined from a calibration curve of absorbance versus concentration.
  Inversion Test—The inversion test provides a visual assessment of the ability of the Gelatin Solution to form and maintain a gel at a temperature of 2-8° C. and for the gel to liquefy at room temperature.

Elucidation of Other Biomaterial Characteristics

Biomaterials used in NKA can be further characterized for the rheological properties and viscosity. Rheology and viscosity testing will be performed for verification purposes only and are intended to be used for expanded characterization of biomaterials obtained from other vendors.

Rheological properties of the Biomaterial can be measured first at 4° C., then at 25° C. through the use of a Couette Cell style rheometer. The sample is equilibrated for at least 30 minutes at each temperature. An acceptable storage modulus (G'>10) at the lower temperature reflects the ability of the solution to form and maintain a gel at NKA shipping and transport temperature of 2-8° C. An acceptable loss modulus (G"<10) at the higher temperature reflects the ability of the gel to liquefy at room temperature as required for delivery and implantation of NKA.

Viscosity of the Biomaterial is measured using a cone and plate viscometer at 37° C. and a shear rate of 200-300 s-1. Solutions with viscosities in range of 1.05-1.35 cP can be efficiently delivered through 18-27 gauge needles.

Figure 2D:
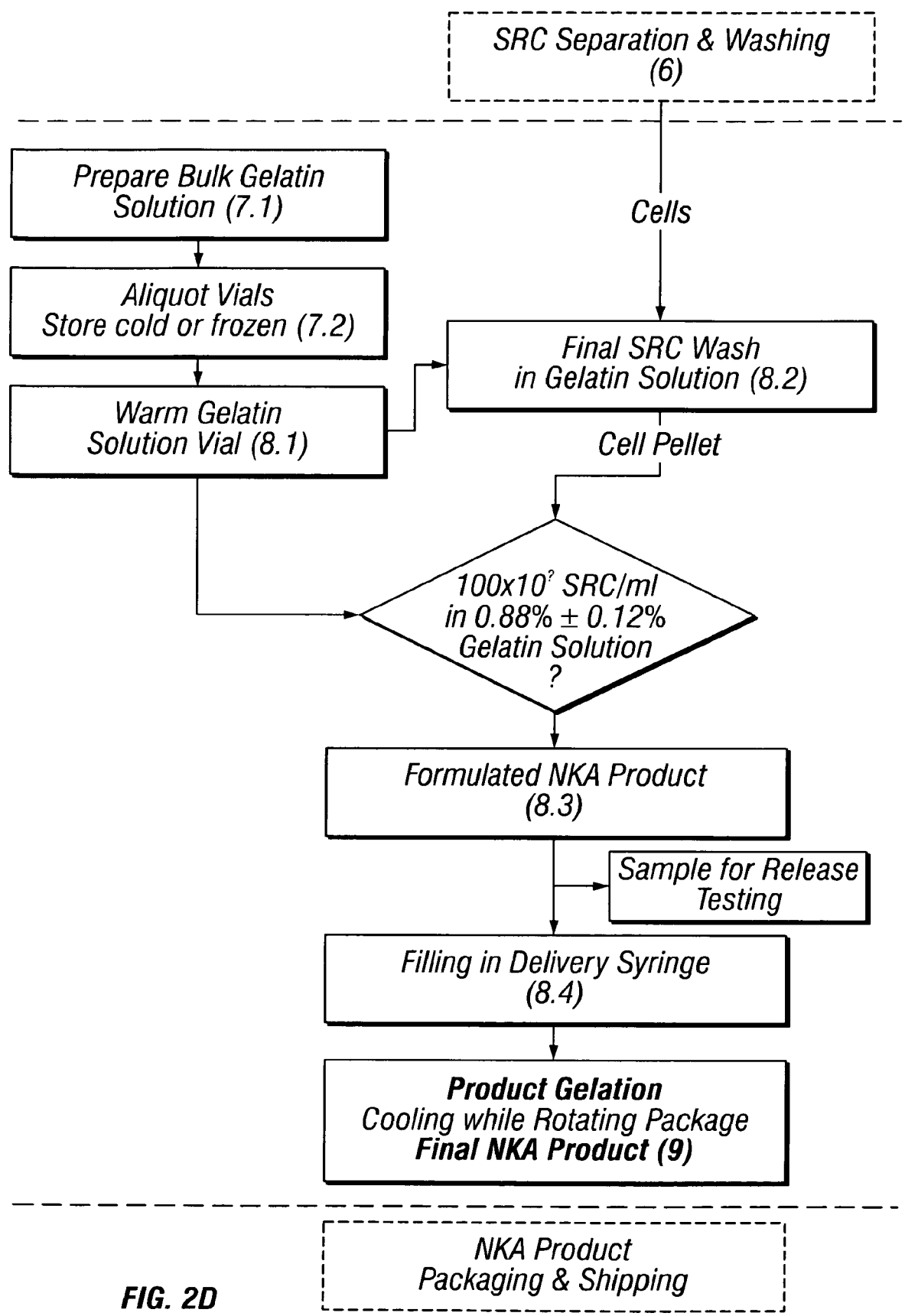
Figure 3:
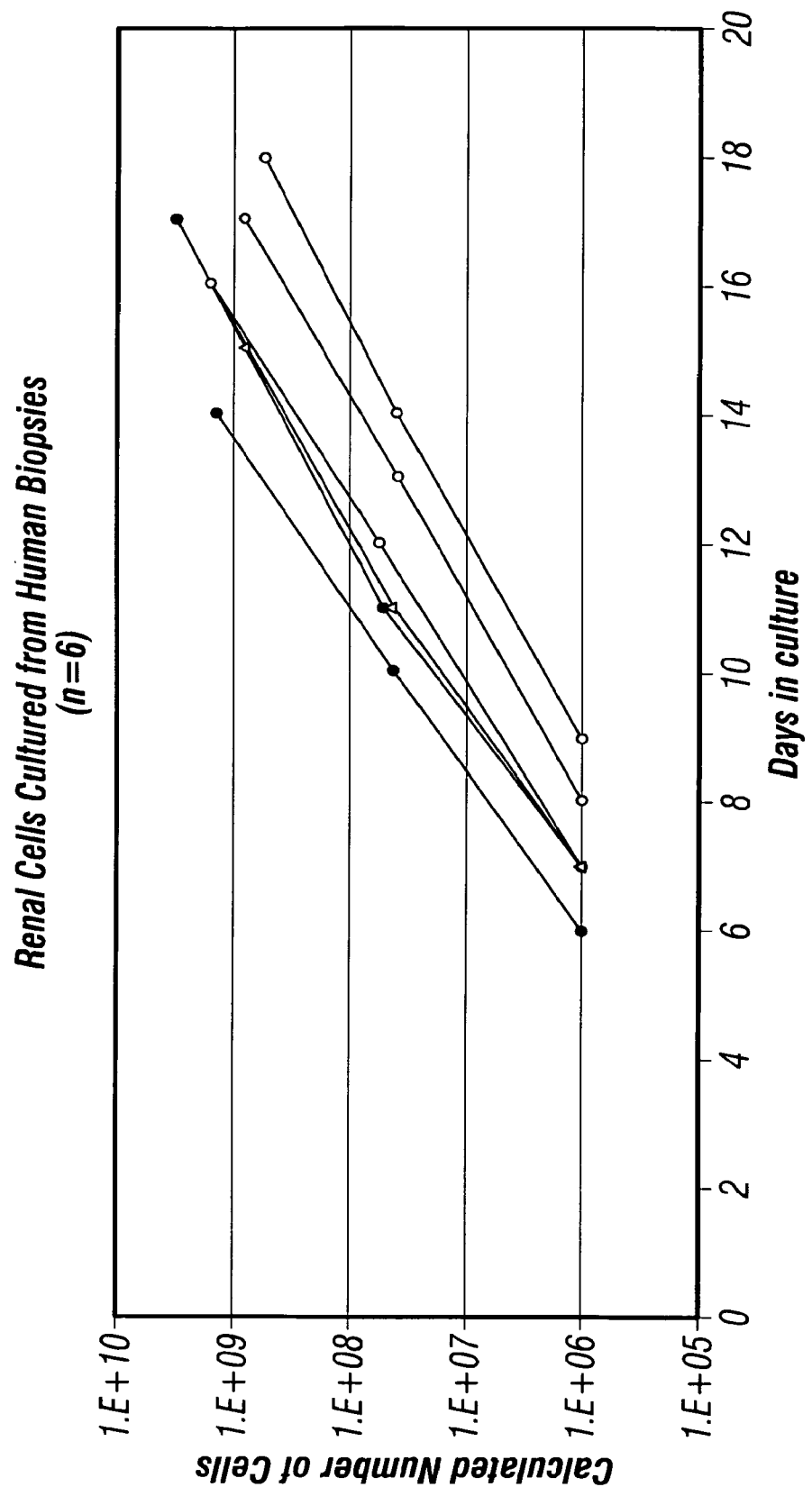
FIG. 3 is a graph that exemplifies the variations in culture duration and cell yields from six patients.

In preparation for NKA formulation, gelatin is dissolved in DPBS to a specified concentration (0.88%±0.12% w/v) to form a Gelatin Solution (FIG. 2D). Gelatin Solution was filter sterilized through a 0.1 µm filter and aliquoted into tubes. Samples were taken for release of the Gelatin Solution prior to freezing or formulation of NKA. The gelled hydrogel is stored refrigerated or frozen as a bulk material ready for formulation (FIG. 2D).

Example 14

NKA Formulation

Washed SRC from Example 5 were counted using Trypan Blue dye exclusion. Gelatin Solution was removed from cold storage and liquefied by warming to 26-30° C. A volume of SRC suspension containing the required number of cells was centrifuged and re-suspended in liquefied Gelatin Solution for a final wash step. This suspension was centrifuged and the SRC pellet is re-suspended in sufficient Gelatin Solution to achieve a resultant SRC concentration of $100 \times 10^6$ cells/mL in the formulated NKA (FIG. 2D).

NKA is presented in a sterile, single-use 10 mL syringe. The final volume was calculated from the concentration of $100 \times 10^6$ SRC/mL of NKA and the target dose of $3.0 \times 10^6$ SRC/g kidney weight (estimated by MRI).

Example 15

NKA Filling and Gelation

NKA product was aseptically filled into the syringe in the NKA package in a BSC for tissue processing and cell culture operations (FIG. 2D). Dynamic air sampling was performed for the duration of the filling process, including viable and non-viable sampling.

Formulated NKA was contained in a 50 mL sterile centrifuge tube. A sterile cannula was attached to a 10 mL transfer syringe. NKA was manually drawn into the transfer syringe from the 50 mL tube via the cannula. The cannula was removed and the transfer syringe was connected to the luer-lock fitting at the end of the NKA package tubing. NKA was transferred to the syringe in the NKA package by depressing the plunger on the transfer syringe. A minimum of 8.5 mL of product was transferred to the syringe in the NKA package. Air entrapped in the syringe was removed by inverting the syringe and slowly depressing the plunger. After filling was complete, the tubing on the NKA package was sealed with an RF Sealer. Remaining product in the transfer syringe was returned to the 50 mL tube. Quality control (release testing) samples were taken from the 50 mL tube. The NKA package was rotated for a minimum of 2 hours to keep the cells in suspension while cooling to 2-8° C. to form the final gelled NKA (FIG. 2D).

Rapid cooling was required for gelation to take place so that cells do not settle in the Gelatin Solution. The temperature of the Gelatin Solution in a syringe was monitored as it was placed into refrigerated conditions. Rapid temperature drop was observed. After 1 hour, the temperature had dropped to within 0.3° C. of the final temperature 4.4° C.

Cooling of the Gelatin Solution starts the gelation process but a finite amount to time was required for the formed gel to stabilize such that the SRC will remain suspended in the gel on storage. Syringes containing formulated NKA were rotated either overnight or for 1.25 hours and then held upright overnight. Subsequently, the contents were removed and cell concentration was measured in four different segments of the product. Analysis indicates that there was no difference among the four segments, thus no measurable cell settling occurs once NKA has rotated at cold temperature for a minimum of 1.25 hours (data not shown).

Example 16

NKA Packaging and Shipping

NKA was packaged along with the appropriate documentation into the NKA Shipper. The Shipper is designed to maintain a temperature range of 2-8° C. during transportation to the clinical site. Cooled (gelled) formulated product has a shelf life of 3 days.

A temperature recorder was included with the NKA package to monitor the temperature during shipment. The Batch Number of NKA was verified against the unique Patient ID recorded in the shipping/receiving log book by the Quality group. NKA Shipper was shipped to the clinical site via courier or similar secure transportation.

Example 17

Implantation of the NKA (SRC Cell Population)

This example demonstrates the regenerative properties of the selected heterogeneous human renal cells.

NKA Delivery System

NKA delivery system was composed of a cannula (needle) compatible with cell delivery and a syringe. Different vendors use the terms cannula or needle to describe cell delivery products. For this description the term cannula and needle are used interchangeably. The proposed clinical trial utilized the same delivery system (cannula and syringe) used in the animal studies adapted to human size and anatomy. A laparoscopic surgical procedure was used.

The main component of NKA delivery system was the cannula. A cannula that was compatible with NKA was used.

NKA Implantation

In preparation for implantation, NKA was allowed to warm to room temperature just before injection into the kidney to liquefy the product.

NKA was targeted for injection into the kidney cortex via a needle or cannula and syringe compatible with cell delivery. The use of a piercing needle (cannula) to penetrate the kidney capsule allowed introduction of the delivery needle/cannula into the kidney cortex. The syringe containing NKA was attached to the delivery needle and NKA was injected into multiple sites into the kidney cortex. The schematic in FIG. 7 illustrates the concept of injecting NKA into a kidney using a needle compatible with cell delivery and distribution into a solid organ.

NKA was delivered directly into the kidney cortex. NKA delivery in patients used a standardized laparoscopic procedure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing a formulation for treatment of kidney disease in a mammal comprising:
   characterizing a heterogeneous renal cell population prepared from a kidney sample of the mammal as suitable for implantation and/or eliciting a regenerative response, the characterizing comprising:
   (i) determining that cells of the population express gamma-glutamyl transpeptidase (GGT)-1;
   (ii) determining that cells of the population express a cytokine cytokeratin (CK); and
   (iii) determining that cells of the population secrete vascular endothelial growth factor (VEGF) and kidney injury molecule (KIM)-1; and
   formulating the heterogeneous renal cell population, characterized as suitable for implantation and/or eliciting the regenerative response, with a (i) biomaterial or (ii) pharmaceutically acceptable carrier or excipient.

2. The method of claim 1, wherein the heterogeneous renal cell population is identified as suitable for implantation and/or eliciting a regenerative response if the percentage of cells that express GGT-1 is determined to be greater than 10%.

3. The method of claim 2, wherein the heterogeneous renal cell population is identified as suitable for implantation and/or eliciting an immune response if the percentage of cells that express GGT-1 is determined to be greater than 20%.

4. The method of claim 3, wherein the heterogeneous renal cell population is identified as suitable for implantation and/or eliciting an immune response if the percentage of cells that express GGT-1 is determined to be greater than 30%.

5. The method of claim 1, wherein the CK is CK18.

6. The method of claim 5, wherein the heterogeneous renal cell population is identified as suitable for implantation and/or eliciting a regenerative response if the percentage of cells that express CK18 is greater than 80%.

7. The method of claim 1, wherein the heterogeneous renal cell population is identified as suitable for implantation and/or eliciting a regenerative response if the percentage of cells that express the CK is greater than 80%.

8. The method of claim 1, wherein the heterogeneous renal cell population is prepared from the kidney sample by a method comprising a step of density gradient centrifugation.

9. The method of claim 8, wherein cells of the heterogeneous renal cell population are iodixanol-resistant.

10. The method of claim 1 further comprising, at the step of characterizing: (iv) determining that cells of the population comprise GGT activity.

11. The method of claim 10 further comprising, at the step of characterizing: (v) determining that cells of the population comprise LAP activity.

12. The method of claim 1 further comprising, at the step of characterizing: (iv) determining that cells of the population comprise leucine aminopeptidase (LAP) activity.

13. The method of claim 1, wherein the kidney sample is a kidney biopsy.

14. The method of claim 1, wherein the formulating comprises suspending the heterogeneous renal cell population in the pharmaceutically acceptable carrier or excipient.

15. The method of claim 14, wherein the pharmaceutically acceptable carrier or excipient comprises one or more of saline, buffered saline, dextrose, water, collagen, alginate, hyaluronic acid, polyethyleneglycol, polyvinylalcohol, and carboxymethylcellulose.

16. The method of claim 1, wherein the formulating comprises combining the heterogeneous renal cell population with the biomaterial.

17. The method of claim 16, wherein the biomaterial is a liquid or hydrogel.

18. The method of claim 17, wherein the hydrogel comprises gelatin or collagen.

19. The method of claim 18, wherein the hydrogel comprises gelatin.

* * * * *